United States Patent
Shafren et al.

(10) Patent No.: US 11,389,495 B2
(45) Date of Patent: *Jul. 19, 2022

(54) COMBINATION METHOD FOR TREATMENT OF CANCER

(71) Applicant: MERCK SHARP & DOHME LLC, Rahway, NJ (US)

(72) Inventors: Darren Shafren, Newcastle (AU); Gough Geoffrey Au, Maryland (AU)

(73) Assignee: MERCK SHARP & DOHME LLC, Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/868,805

(22) Filed: Jan. 11, 2018

(65) Prior Publication Data

US 2019/0134119 A1    May 9, 2019

Related U.S. Application Data

(63) Continuation of application No. 15/121,517, filed as application No. PCT/AU2015/000111 on Feb. 27, 2015, now abandoned.

(30) Foreign Application Priority Data

Feb. 27, 2014 (AU) .................................. 2014900647

(51) Int. Cl.
| | | |
|---|---|---|
| *A61K 35/768* | (2015.01) | |
| *A61K 39/395* | (2006.01) | |
| *A61K 9/00* | (2006.01) | |
| *C12N 7/00* | (2006.01) | |
| *A61K 39/00* | (2006.01) | |

(52) U.S. Cl.
CPC .......... *A61K 35/768* (2013.01); *A61K 9/0019* (2013.01); *A61K 39/3955* (2013.01); *A61K 39/39558* (2013.01); *C12N 7/00* (2013.01); *A61K 2039/505* (2013.01); *A61K 2039/525* (2013.01); *A61K 2039/54* (2013.01); *A61K 2039/572* (2013.01); *C12N 2770/32332* (2013.01); *C12N 2770/32333* (2013.01); *C12N 2770/32371* (2013.01)

(58) Field of Classification Search
CPC ................ A61K 35/768; A61K 9/0019; A61K 39/39558; A61K 39/3955; A61K 2039/505; A61K 2039/525; A61K 2039/54; A61K 2039/572; C12N 7/00; C12N 2770/32333; C12N 2770/32371; C12N 2770/32332; A61P 43/00; A61P 35/02; A61P 35/00
See application file for complete search history.

(56) References Cited

U.S. PATENT DOCUMENTS

| | | |
|---|---|---|
| 5,166,057 A | 11/1992 | Palese et al. |
| 5,223,409 A | 6/1993 | Ladner et al. |
| 5,273,745 A | 12/1993 | Schirrmacher |
| 5,403,484 A | 4/1995 | Ladner et al. |
| 5,571,698 A | 11/1996 | Ladner et al. |
| 5,786,199 A | 7/1998 | Palese |
| 5,854,037 A | 12/1998 | Palese et al. |
| 5,891,680 A | 4/1999 | Lieschke et al. |
| 6,146,642 A | 11/2000 | Garcia-Sastre et al. |
| 6,190,901 B1 | 2/2001 | Sundick et al. |
| 6,287,554 B1 | 9/2001 | Sundick et al. |
| 6,451,323 B1 | 9/2002 | Garcia-Sastre et al. |
| 6,544,785 B1 | 4/2003 | Palese et al. |
| 6,635,416 B2 | 10/2003 | Palese et al. |
| 6,649,372 B1 | 11/2003 | Palese et al. |
| 6,719,979 B2 | 4/2004 | Peeters et al. |
| 6,737,522 B2 | 5/2004 | Sundick et al. |
| 6,852,522 B1 | 2/2005 | Palese et al. |
| 6,896,881 B1 | 5/2005 | Russell et al. |
| 7,052,685 B1 | 5/2006 | Rook |
| 7,056,689 B1 | 6/2006 | Lorence et al. |
| 7,060,430 B2 | 6/2006 | Palese et al. |
| 7,141,550 B2 | 11/2006 | Moelling et al. |
| 7,244,558 B1 | 7/2007 | Samal et al. |
| 7,332,169 B2 | 2/2008 | Peeters et al. |
| 7,361,354 B1 | 4/2008 | Shafren |
| 7,384,774 B2 | 6/2008 | Palese et al. |
| 7,442,379 B2 | 10/2008 | Garcia-Sastre et al. |
| 7,442,527 B2 | 10/2008 | Palese et al. |
| 7,470,426 B1 | 12/2008 | Roberts et al. |
| 7,485,292 B2 | 2/2009 | Shafren |
| 7,494,808 B2 | 2/2009 | Palese et al. |

(Continued)

FOREIGN PATENT DOCUMENTS

| | | |
|---|---|---|
| AU | 2002307971 B2 | 1/2008 |
| CN | 101787373 B | 6/2013 |

(Continued)

OTHER PUBLICATIONS

Shafren et al (Annals of Oncology, Jun. 2011, vol. 22, Supp. Suppl. 5, pp. v59. Abstract No. P-01030).*
Nogawa et al. (The journal of Clinical Investigation, 2005. vol. 115, No. 4, pp. 978-985).*
Agrez, Michael V., Integrin alpha v beta 6 Enhances Coxsackievirus B1 Lytic Infection of Human Colon Cancer Dells, Virology, 1997, 71-77, 239.
Aigner, Maximilian, An effective tumor vaccine optimized for costimulation via bispecific and trispecific fusion proteins, International Journal of Oncology, 2008, 777-789, 32(4).
Alexander, D.J., Newcastle disease virus—an avian paramyxovirus, Newcastle Disease, 1988, 1-22.

(Continued)

*Primary Examiner* — Nancy J Leith
(74) *Attorney, Agent, or Firm* — Li Su; Anna L. Cocuzzo

(57) ABSTRACT

The invention relates to methods of treating tumours comprising delivering an oncolytic virus or oncolytic viral RNA via direct injection or systemic administration or intravesicular administration to the tumour or cancer in combination with the co-administration of an immuno-stimulatory agent via the systemic route to a mammal.

42 Claims, 44 Drawing Sheets

Specification includes a Sequence Listing.

(56) References Cited

U.S. PATENT DOCUMENTS

| | | |
|---|---|---|
| 7,547,442 B2 | 6/2009 | Peeters et al. |
| 7,736,640 B2 | 6/2010 | Lorence et al. |
| 7,740,863 B2 | 6/2010 | Loosmore et al. |
| 7,780,962 B2 | 8/2010 | Roberts et al. |
| 7,833,774 B2 | 11/2010 | Palese et al. |
| 7,858,081 B2 | 12/2010 | Bernard et al. |
| 8,043,612 B2 | 10/2011 | Roberts et al. |
| 8,105,578 B2 | 1/2012 | Roberts et al. |
| 8,114,416 B2 | 2/2012 | Johansson |
| 8,124,084 B2 | 2/2012 | Lefrancois et al. |
| 8,163,879 B2 | 4/2012 | Wong et al. |
| 8,236,298 B2 * | 8/2012 | Au ................. A61K 35/768 424/93.6 |
| 8,475,790 B2 | 7/2013 | Jure-Kunkel |
| 8,490,289 B2 | 7/2013 | Nystrom et al. |
| 8,492,118 B2 | 7/2013 | Wong et al. |
| 8,507,222 B2 | 8/2013 | Wong et al. |
| 8,591,881 B2 | 11/2013 | Palese et al. |
| 8,709,417 B2 | 4/2014 | Allison et al. |
| 8,765,462 B2 | 7/2014 | Medin et al. |
| 8,871,191 B2 | 10/2014 | Pavlakis et al. |
| 8,940,288 B2 | 1/2015 | Lefrancois et al. |
| 9,217,136 B2 | 12/2015 | Palese et al. |
| 9,375,475 B2 | 6/2016 | Allison et al. |
| 9,387,242 B2 | 7/2016 | Palese et al. |
| 9,476,033 B2 | 10/2016 | Samal et al. |
| 10,023,637 B2 | 7/2018 | Allison et al. |
| 10,251,922 B2 | 4/2019 | Palese et al. |
| 2002/0052030 A1 | 5/2002 | Wonderling et al. |
| 2002/0150554 A1 | 10/2002 | Sundick et al. |
| 2003/0044384 A1 | 3/2003 | Roberts et al. |
| 2003/0224017 A1 | 12/2003 | Samal et al. |
| 2004/0234552 A1 | 11/2004 | Peeters et al. |
| 2005/0191617 A1 | 9/2005 | Inoue et al. |
| 2005/0235134 A1 | 10/2005 | O'Sullivan |
| 2005/0238622 A1 | 10/2005 | Axelrod et al. |
| 2006/0216310 A1 | 9/2006 | Lorence et al. |
| 2008/0057037 A1 | 3/2008 | Roberts et al. |
| 2008/0160031 A1 | 7/2008 | Shafren |
| 2008/0206201 A1 | 8/2008 | Beier et al. |
| 2009/0061521 A1 | 3/2009 | Palese et al. |
| 2009/0081161 A1 | 3/2009 | Roberts et al. |
| 2009/0082299 A1 | 3/2009 | Felber et al. |
| 2009/0175826 A1 | 7/2009 | Subbiah et al. |
| 2009/0214590 A1 | 8/2009 | Sundick et al. |
| 2009/0238791 A1 | 9/2009 | Jacques et al. |
| 2009/0280144 A1 | 11/2009 | Garcia-Sastre et al. |
| 2010/0092430 A1 | 4/2010 | Beier et al. |
| 2010/0104578 A1 | 4/2010 | Shafren |
| 2010/0297072 A1 | 11/2010 | Depinho et al. |
| 2011/0020282 A1 | 1/2011 | Beier et al. |
| 2011/0044937 A1 | 2/2011 | Bell et al. |
| 2011/0081311 A1 | 4/2011 | Pavlakis et al. |
| 2011/0158938 A1 | 6/2011 | Bernard et al. |
| 2011/0189189 A1 | 8/2011 | Jure-Kunkel |
| 2012/0034242 A1 | 2/2012 | Jooss et al. |
| 2012/0058141 A1 | 3/2012 | Palese et al. |
| 2012/0058538 A1 | 3/2012 | Palese et al. |
| 2012/0064112 A1 | 3/2012 | Samal et al. |
| 2012/0071859 A1 | 3/2012 | Morgan et al. |
| 2012/0114648 A1 | 5/2012 | Langermann et al. |
| 2012/0122185 A1 | 5/2012 | Palese et al. |
| 2013/0108665 A1 | 5/2013 | Liang |
| 2014/0044678 A1 | 2/2014 | Palese et al. |
| 2014/0134128 A1 | 5/2014 | Wong et al. |
| 2014/0186303 A1 | 7/2014 | Subbiah et al. |
| 2014/0205560 A1 | 7/2014 | Wong et al. |
| 2014/0219955 A1 | 8/2014 | Wong et al. |
| 2014/0242025 A1 | 8/2014 | Wong et al. |
| 2014/0271677 A1 | 9/2014 | Palese et al. |
| 2014/0377221 A1 | 12/2014 | Tufaro |
| 2015/0017121 A1 | 1/2015 | Becher et al. |
| 2015/0093357 A1 | 4/2015 | Lefrancois et al. |
| 2015/0132257 A1 | 5/2015 | Wong et al. |
| 2015/0133531 A1 | 5/2015 | Wiegand |
| 2015/0139945 A1 | 5/2015 | Lefrancois et al. |
| 2015/0152188 A1 | 6/2015 | Morisseau et al. |
| 2015/0250837 A1 | 9/2015 | Nolin et al. |
| 2016/0068823 A1 | 3/2016 | Palese et al. |
| 2016/0136211 A1 | 5/2016 | Shafren |
| 2017/0037379 A1 | 2/2017 | Palese et al. |
| 2017/0247425 A1 | 8/2017 | Ungerechts et al. |

FOREIGN PATENT DOCUMENTS

| | | |
|---|---|---|
| CN | 105734023 A | 7/2016 |
| CN | 106166294 A | 11/2016 |
| DE | 3922444 A1 | 1/1991 |
| EP | 0780475 A1 | 6/1997 |
| EP | 0974660 A1 | 1/2000 |
| EP | 1248654 B1 | 10/2005 |
| EP | 1032269 B1 | 8/2007 |
| EP | 1486211 B1 | 10/2008 |
| EP | 2085092 A1 | 8/2009 |
| EP | 0702085 B2 | 1/2010 |
| EP | 2669381 A1 | 12/2013 |
| EP | 2393921 B1 | 7/2015 |
| EP | 2766035 B1 | 3/2018 |
| EP | 2987856 B1 | 7/2018 |
| WO | 1994025627 A1 | 11/1994 |
| WO | 1996034625 A1 | 11/1996 |
| WO | 1997006270 A1 | 2/1997 |
| WO | 1997012032 A1 | 4/1997 |
| WO | 1997014433 A1 | 4/1997 |
| WO | 1998002530 A1 | 1/1998 |
| WO | 1998013501 A2 | 4/1998 |
| WO | 1998053078 A1 | 11/1998 |
| WO | 1999002657 A1 | 1/1999 |
| WO | 1999015672 A1 | 4/1999 |
| WO | 1999018799 A1 | 4/1999 |
| WO | 1999066045 A1 | 12/1999 |
| WO | 2000062735 A2 | 10/2000 |
| WO | 2000067786 A1 | 11/2000 |
| WO | 2001004333 A1 | 1/2001 |
| WO | 2001020989 A1 | 3/2001 |
| WO | WO2001307866 A1 | 5/2001 |
| WO | 2002102404 A1 | 12/2002 |
| WO | 2003092579 A2 | 11/2003 |
| WO | WO 2006/017914 A1 | 2/2006 |
| WO | 2006050984 A2 | 5/2006 |
| WO | 2007008918 A2 | 1/2007 |
| WO | WO 2007/025365 A1 | 3/2007 |
| WO | 2007064802 A1 | 6/2007 |
| WO | 2007084342 A2 | 7/2007 |
| WO | 2007113648 A2 | 10/2007 |
| WO | 2008011726 A1 | 1/2008 |
| WO | 2008156712 A1 | 12/2008 |
| WO | 2009002562 A2 | 12/2008 |
| WO | 2009095167 A1 | 8/2009 |
| WO | WO2010091262 A1 | 8/2010 |
| WO | WO 2010/135242 A1 | 11/2010 |
| WO | 2011022656 A2 | 2/2011 |
| WO | 2011041613 A2 | 4/2011 |
| WO | 2011119628 A2 | 9/2011 |
| WO | 2012000188 A1 | 1/2012 |
| WO | 2012000443 A1 | 1/2012 |
| WO | 2012142529 A2 | 10/2012 |
| WO | 2013053775 A1 | 4/2013 |
| WO | WO 2013/112942 A1 | 8/2013 |
| WO | 2013178344 A1 | 12/2013 |
| WO | 2014047350 A1 | 3/2014 |
| WO | 2014066527 A2 | 5/2014 |
| WO | 2014158811 A1 | 10/2014 |
| WO | 2014170032 A1 | 10/2014 |
| WO | 2015018528 A1 | 2/2015 |
| WO | 2015018529 A1 | 2/2015 |
| WO | 2015032755 A1 | 3/2015 |
| WO | 2015131994 A1 | 9/2015 |
| WO | 2016018920 A1 | 2/2016 |

(56) References Cited

FOREIGN PATENT DOCUMENTS

| WO | 2016048903 A1 | 3/2016 |
|---|---|---|
| WO | 2016094377 A1 | 6/2016 |

OTHER PUBLICATIONS

Altomonte, Jennifer, Engineered Newcastle Disease Virus as an Improved Oncolytic Agent Against Hepatocellular Carcinoma, Molecular Therapy, 2010, 275-284, vol. 18, No. 2.
Annels, Nicola E., Oncolytic Immunotherapy for Bladder Cancer Using Coxsackie A21 Virus, Molecular Therapy Oncolytics, 2018, 1-12, 9.
Au, Gough G., Oncolysis of maligant human melanoma tumors by Coxsackieviruses A13, A15 and A18, Virology Journal, 2011, 1-6, 8:22.
Ayers, Mark, IFN-gamma-related mRNA profile predicts clinical response to PD-1 blockade, The Journal of Clinical Investigation, 2017, 2930-2940, 127.
Ayllon, Juan, Rescue of Recombinant Newcastle Disease Virus from cDNA, Journal of Visualized Experiments, 2013, 1-9, 80.
Barber et al., Restoring function in exhausted CD8 T cells during chronic viral infection, Nature, 2006, pp. 682-687, vol. 439.
Bart, Robert S., Role of Interferon in the Anti-Melanoma Effects of Poly (I).Poly (C) and Newcastle Disease Virus, Nature New Biology, 1973, 229-230, vol. 245.
Bauzon, Maxine, Armed therapeutic viruses—a disruptive therapy on the horizon of cancer immunotherapy, Frontiers in Immunology, 2014, 1-10, vol. 5, Article 74.
Berry, Linda J., Potent Oncolytic Activity of Human Enteroviruses Against Human Prostate Cancer, The Prostate, 2008, 577-587, 68(6).
Blackburn, Shawn D., Tissue-Specific Differences in PD-1 and PD-L1 Expression during Chronic Viral Infection Implications for CD8 T-Cell Exhaustion, Journal of Virology, 2010, 2078-2089, 84(4).
Blake II, Robert C., Automated Kinetic Exclusion Assays to Quantify Protein Binding Interactions in Homogeneous Solution, Analytical Biochemistry, 1999, 123-134, 272.
Brahmer, Julie R., Phase I study of single-agent anti-programmed death-1 (MDX-1106) in refractory solid tumors . . . , Journal Clinical Oncology, 2010, 3167-3175, vol. 28, No. 19.
Brown, Keturah E., Role of PD-1 in regulating acute infections, Current Opinion in Immunology, 2010, 397-401, 22(3).
Bryant, Jerry, Development of Intermediate-Grade (Mantle Cell) and Low-Grade (Small Lymphocytic and Marginal Zone) Human Non-Hodgkin's Lymphomas Xenotransplanted in Severe Combined Immunodeficiency Mouse Models, Laboratory Investigation, 2000, 557-573, vol. 80, No. 4.
Bujis, Pascal, Recombinant Immunomodulating Lentogenic or Mesogenic Oncolytic Newcastle Disease Virus for Treatment of Pancreatic Adenocarcinoma, Viruses, 2015, 2980-2998, 7.
Carthon, Bradley C., Preoperative CTLA-4 Blockade: Tolerability and Immune Monitoring in the Setting of a Presurgical Clinical Trial, Clinical Cancer Research, 2010, 2861-2871, 16(10).
Caruso, Manuel, Adenovirus-mediated interleukin-12 gene therapy for metastatic colon carcinoma, Proc. Natl. Acad. Sci. USA, 1996, 11302-11306, 93.
Chen, Hong, CD4 T Cells Require ICOS-Mediated PI3K Signaling to Increase T-Bet Expression in the Setting of Anti-CTLA-4-Therapy, Cancer Immunology Research, 2013, 167-176, 2(2).
Cheng, Xing, Genetic Modification of Oncolytic Newcastle Disease Virus for Cancer Therapy, Journal of Virology, 2016, 5343-5352, 90(1).
Clinical Trial NCT01295827, Study of Pembrolizumab (MK-3475) in Participants With Progressive Locally Advanced or Metastatic Carcinoma, Melanoma, or Non-Small Cell Lung Carcinoma (P07990/MK-3475-001/KEYNOTE-001), Merck Sharp & Dohme Corp., updated Sep. 13, 2018(KEYNOTE-001).
Csatary, L.K., MTH-68/H oncolytic viral treatment in human high-grade gliomas, Journal of Neuro-Oncology, 2004, 83-93, 67.
Curran, Michael A., Combination CTLA-4 Blockade and 4-1BB Activation Enhances Tumor Rejection by Increasing T-Cell Infiltration, Proliferation, and Cytokine Production, PLoS One, 2011, e19499, vol. 6, Issue 4.
D. M. Pardoll, The blockade of immune checkpoints in cancer immunotherapy, Nature Reviews/Cancer, 2012, pp. 252-264, vol. 12.
De Leeuw, Olav S., Virulence of Newcastle disease virus is determined by the cleavage site of the fusion protein and by both the stem region and globular head of the haemagglutinin-neuraminidase protein, Journal of General Virology, 2005, 1759-1769, 86.
Dezfouli, Shala, Enhancing CTL responses to melanoma cell vaccines in vivo: synergistic increases obtained using IFNgamma primed and IFNbeta treated B7-1+ B16-F10 melanoma cells, Immunology and Cell Biology, 2003, 459-471, 81.
Diamond, M.S. et al., Type I interferon is selectively required by dendritic cells for immune rejection of tumors, The Journal of Experimental Medicine, 2011, pp. 1989-2003, vol. 208, No. 10.
Dias, J.D., Targeted cancer immunotherapy with oncolytic adenovirus coding for a fully human monoclonal antibody specific for CTLA-4, Gene Therapy, 2012, 988-998, 19.
Dupraz, Philippe, Dominant Negative MyD88 Proteins Inhibit Interleukin-1 beta/Interferon-gamma-mediated Induction of Nuclear Factor kB-dependent Nitrite Production and Apoptosis in beta Cells, Journal of Biological Chemistry, 2000, 37672-37678, vol. 275, No. 48.
Elankumaran, Subbiah, Type I Interferon-Sensitive Recombinant Newcastle Disease Virus for Oncolytic Virotherapy, Journal of Virology, 2010, 3835 3844, vol. 84, No. 8.
Fan, Xiaozhou, Engagement of the ICOS pathway markedly enhances efficacy of CTLA-4 blockade in cancer mmunotherapy, The Journal of Experimental Medicine, 2014, 715-725, 211(4).
Fecci, Peter E., Systemic CTLA-4 Blockade Ameliorates Glioma-Induced Changes to the CD4+ T Cell Compartment without Affecting Regulatory T-Cell Function, Clinical Cancer Research, 2007, 2158-2167, 13.
Fiola, Christoph, Tumor selective replication of Newcastle Disease Virus: Association with defects of tumor cells in antiviral defence, International Journal of Cancer, 2006, 328-338, 119.
Fisher, Daniel T., IL-6 trans-signaling licenses mouse and human tumor microvascular gateways for trafficking of cytotoxic T cells, The Journal of Clinical Investigation, 2011, 3846-3859, vol. 121, No. 10.
Fodde, Riccardo, Disease model: familial adenomatous polyposis, Trends in Molecular Medicine, 2001, 369-373, vol. 7, No. 8.
Fournier, Philippe, Oncolytic Newcastle Disease Virus as Cutting Edge between Tumor and Host, Biology, 2013, 936-975, 2.
Foy, Eileen, Regulation of Interferon Regulatory Factor-3 by the Hepatitis C Virus Serine Protease, Science, 2003, 1145-1148, 300.
Franciszkiewicz, Katarzyna, Role of Chemokines and Chemokine Receptors in Shaping the Effector Phase of the Antitumor Immune Response, Cancer Research, 2012, 6325-6332, 72.
Fransen, M. et al., Controlled local delivery of CTLA-4 blocking antibody induces CD8(+) T-cell-dependent tumor aradication and decreases risk of toxic side effects, Clinical Cancer Research, 2013, 5381-5389, 19(19).
Freeman, AI, et al., Phase I/II Trial of Intravenous HDV-HUJ Oncolytic Virus in Recurrent Glioblastoma Multiforme, Molecular Therapy, 2006, pp. 221-228, 13(1).
Fu, Tihui, The ICOS/ICOSL Pathway is Required for Optimal Antitumor Responses Mediated by Anti-CTLA-4 Therapy, Cancer Research, 2011, 5445-5454, 71.
Fuertes, Mercedes B., Host type IIFN signals are required for antitumor CD8+ T cell responses through CDS {alpha}+ dendritic cells, J Exp. Med., 2011, 2005-2016, vol. 208, No. 10.
Galivo, Feorillo, Interference of CD40L-Mediated Tumor Immunotherapy by Oncolytic Vesicular Stomatitis Virus, Human Gene Therapy, 2010, 439-450, 21.
Gao, Qinshan, Expression of Transgenes from Newcastle Disease Virus with a Segmented Genome, Journal of Virology, 2008, 2692-2698, vol. 82, No. 6.
Garcia-Sastre, A., Introduction of Foreign Sequences into the Genome of Influenza A Virus, Dev. Biol. Stand., 1994, 237-246, 82.

(56) References Cited

OTHER PUBLICATIONS

Garcia-Sastre, Adolfo, Use of a Mammalian Internal Ribosomal Entry Site Element for Expression of a Foreign Protein by a Transfectant Influenza Virus, Journal of Virology, 1994, 6254-6261, vol. 68, No. 10.
Ghaneh, P., Adenovirus-mediated transfer of p53 and p16(INK4a) results in pancreatic cancer regression in vitro and in vivo, Gene Therapy, 2001, 199-208, 8.
Goff, Peter H., A Majority of Infectious Newcastle Disease Virus Particles Contain a Single Genome, while a Minority Contain Multiple Genomes, Journal of Virology, 2012, 10852-10856, 86(19).
Guo, Zong Sheng, Oncolytic immunotherapy: dying the right way is a key to eliciting potent antitumor immunity, Frontiers in Oncology, 2014, 1-11, vol. 4, Article 74.
Haas, Claudia, A tumor vaccine containing anti-CD3 and anti-CD28 bispecific antibodies triggers strong and durable antitumor activity in human lymphocytes, International Journal of Cancer, 2006, 658-667, 188(3).
Haas, Claudia, An effective strategy of human tumor vaccine modification by coupling bispecific costimulatory molecules, Cancer Gene Therapy, 1999, 254-262, 6(3).
Haas, Claudia, Bispecific Antibodies Increase T-Cell Stimulatory Capacity in Vitro of Human Autologous Virus-modified Tumor Vaccine, Clinical Cancer Research, 1998, 721-730, 4(3).
Haley, Erin S., Regional administration of oncolytic Echovirus 1 as a novel therapy for the peritoneal dissemination of gastric cancer, J. Mol Med., 2009, 385-399, 87(4).
Hamid et al., Safety and Tumor Responses with Lambrolizumab (Anti—PD-1) in Melanoma, New Eng. J. Med., 2013, 134-144, 369(2).
Hemminki, Akseli, Oncolytic Immunotherapy: Where Are We Clinically?, Scientifica, 2014, 1-7, vol. 2014, Article ID 862925.
Herber, Renee, Squamous Epithelial Hyperplasia and Carcinoma in Mice Transgenic for the Human Papillomavirus Type 16 E7 Oncogene, Journal of Virology, 1996, 1873-1881, vol. 70, No. 3.
Herbst, Roy S., Predictive correlates of response to the anti-PD-L1 antibody MPDL3280A in cancer patients, Nature, 2014, 563-567, 515(7528).
Hirschhorn-Cymerman, Daniel, Induction of tumoricidal function in CD4+ T cells is associated with concomitant memory and terminally differentiated phenotype, The Journal of Experimental Medicine, 2012, 2113-2126, vol. 209, No. 11.
Hofmeyer, Kimberly A., The PD-1/PD-L1 (B7-H1) Pathway in Chronic Infection-Induced Cytotoxic T Lymphocyte Exhaustion, Journal of Biomedicine and Biotechnology, 2011, 1-9, 451694.
Holliger et al., Engineered antibody fragments and the rise of single domains, Nat. BiotechnoL, 2005, pp. 1126-1136, 23.
Hosokawa, Yoshitaka, In vivo analysis of mammary and non-mammary tumorigenesis in MMTV-cyclin D1 transgenic mice deficient in p53, Transgenic Research, 2001, 471-478, 10.
Hotte, Sebastien J., An Optimized Clinical Regimen for the Oncolytic Virus PV701, Clinical Cancer Research, 2007, 977-985, 13.
Houdebine, Louis-Marie, Production of pharmaceutical proteins by transgenic animals, Comparative Immunology Microbiology & Infectious Diseases, 2009, 107-121, 32(2).
Hough, Margarei R., A model for spontaneous B-lineage lymphomas in IgHmu-HOX11 transgenic mice, Proc. Natl. Acad. Sci (USA), 1998, 13853-13858, 95.
Huang, Ju, Preclinical validation: LV/IL-12 transduction of patient leukemia cells for immunotherapy of AML, Molecular Therapy—Methods & Clinical Development, 2016, 1-11, 3, 16074.
Huang, Zhuhui, Newcastle Disease Virus V Protein is Associated with Viral Pathogenesis and Functions as an Alpha Interferon Antagonist, Journal of Virology, 2003, 8676-8685, vol. 77, No. 16.
Huard, Bertrand, CD4/major histocompatibility complex class II interaction analyzed with CD4- and lymphocyte activation gene-3 (LAG-3)-lg fusion proteins, Eur. J. Immunol., 1995, 2718-2721, 25.
Iwai et al., PD-1 Inhibits Antiviral Immunity at the Effector Phase in the Liver, J. Exp. Med., 2003, pp. 39-50, vol. 198.
Iwai, Involvement of PD-L1 on tumor cells in the escape from host immune system and tumor immunotherapy by PD-L1 blockade, Proc. Natl Acad. Sci USA, 2002, pp. 12293-12297, vol. 99.
Kado, Shoichi, Intestinal Microflora are Necessary for Development of Spontaneous Adenocarcinoma of the Large Intestine in T-Cell Receptor Beta Chain and p53 Double-Knockout Mice, Cancer Research, 2001, 2395-2398, 61.
Kamphorst, Alice O., Rescue of exhausted CD8 T cells by PD-1 targeted therapies is CD28-dependent, Science, 2017, 1423-1427, 355(6332).
Kato, Hiroki, Cell Type-Specific Involvement of RIG-I in Antiviral Response, Immunity, 2005, 19-28, 23.
KEYTRUDA Highlights of Prescribing Information, revised Aug. 2018.
Khattar, Sunil K., A Y526Q Mutation in the Newcastle Disease Virus HN Protein Reduces its Functional Activities and Attenuates Virus Replication and Pathogenicity, Journal of Virology, 2009, 7779-7782, vol. 83, No. 15.
Kim, Se-Ho, Expression and Characterization of a Recombinant Fab Fragment Derived from an Anti-Human alpha-Fetoprotein Monoclonal Antibody, Molecules and Cells, 2001, 158-163, vol. 11, No. 2.
Krishnamurthy, Sateesh, Differentially Regulated Interferon Response Determines the Outcome of Newcastle Disease Virus Infection in Normal and Tumor Cell Lines, Journal of Virology, 2006, 5145-5155, vol. 80, No. 11.
Kuraguchi, Mari, Tumor-associated Apc mutations in Mlh1-1-Apc1638N mice reveal a mutational signature of Mlh1 deficiency, Oncogene, 2000, 5755-5763, 19.
Lamb, Robert A., Paramyxoviridae: The Viruses and Their Replication, Fundamental Virology, 1996, 577-604, Third Edition, Chapter 20.
Leach, Dr et al., Enhancement of antitumor immunity by CTLA-4 blockade, Science, 1996, pp. 1734-1736, 271.
Lei, N., An oncolytic adenovirus expressing granulocyte macrophage colony-stimulating factor shows improved specificity and efficacy for treating human solid tumors, Cancer Gene Therapy, 2009, 33-43, 16.
Li, Pingdong, Therapeutic Effects of a Fusogenic Newcastle Disease Virus in Treating Head and Neck Cancer, Head & Neck, 2011, 1394-1399, 33.
Liu, BL, ICP34.5 deleted herpes simplex virus with enhanced oncolytic, immune stimulating, and anti-tumour properties, Gene Therapy, 2003, 292-303, 10.
Liu, Y., Adenovirus-mediated intratumoral expression of immunostimulatory proteins in combination with systemic Treg inactivation induces tumor-destructive immune responses in mouse models, Cancer Gene Therapy, 2011, 407-418, 18.
Lorence, Robert M., Phase 1 Clinical Experience Using Intravenous Administration of PV701, an Oncolytic Newcastle Disease Virus, Current Cancer Drug Targets, 2007, 157-167, 7.
Maeda, Yasuko, Live Bivalent Vaccine for Parainfluenza and Influenza Virus Infections, Journal of Virology, 2005, 3674-6679, vol. 79, No. 11.
Mansour, Mena, Oncolytic Specificity of Newcastle Disease Virus is Mediated by Selectivity for Apoptosis-Resistant Cells, Journal of Virology, 2011, 6015-6023, vol. 85, No. 12.
Mazzolini, Guillermo, Adenoviral Gene Transfer of Interleukin 12 into Tumors Synergizes with Adoptive T Cell Therapy Both at the Induction and Effector Level, Human Gene Therapy, 2000, 113-125, 11.
Mazzolini, Guillermo, Regression of colon cancer and induction of antitumor immunity by intratumoral injection of adenovirus expressing interleukin-12, Cancer Gene Therapy, 1999, 514-522, 6(6).
Meseck, Marcia, A Functional Recombinant Human 4-1BB Ligand for Immune Costimulatory Therapy of Cancer, Journal Immunotheraphy, 2011, 175-182, vol. 34, No. 2.
Morris, Gilbert F., Lung-Specific Expression in Mice of a Dominant Negative Mutant Form of the p53 Tumor Suppressor Protein, Journal of the Louisiana State Medical Society, 1998, 179-185, vol. 150, No. 4.
Muranski, Pawel, Tumor-specific Th17-polarized cells eradicate large established melanoma, Blood, 2008, 362-373, vol. 112, No. 2.

(56) References Cited

OTHER PUBLICATIONS

Murawski, Matthew R., Newcastle Disease Virus-Like Particles Containing Respiratory Syncytial Virus G Protein Induced Protection in BALB/c Mice, with No Evidence of Immunopathology, Journal of Virology, 2010, 1110-1123, vol. 84, No. 2.
Nakaya, Takaaki, Recombinant Newcastle Disease Virus as a Vaccine Vector, Journal of Virology, 2001, 11868-11873, vol. 75, No. 23.
Narvaiza, Inigo, Intratumoral Coinjection of Two Adenoviruses, One Encoding the Chemokine IFN-gamma-Inducible Protein-10 and Another Encoding IL-12, Results in Marked Antitumoral Synergy, Journal of Immunology, 2000, 3112-3122, 164(6).
Newcombe, Nicole G., Cellular receptor interactions of C-cluster human group A coxsackieviruses, Journal of General Virology, 2003, 3041-3050, 84.
Newcombe, Nicole G., Enterovirus Capsid Interactions with Decay-Accelerating Factor Mediate Lytic Cell Infection, Journal of Virology, 2004, 1431-1439, 78(3).
Newcombe, Nicole G., Novel Role for Decay-Accelerating Factor in Coxsackievirus A21-Mediated Cell Infectivity, Journal of Virology, 2004, 12677-12682, 78(22).
Niu, Zeshan, Recombinant Newcastle Disease Virus Expressing IL 15 Demonstrates Promising Antitumor Efficiency in Melanoma Model, Technology in Cancer Research and Treatment, 2015, 607-615, 14(5).
Oseledchyk, Anton, Lysis-independent potentiation of immune checkpoint blockade by oncolytic virus, Oncotarget, 2018, 1-2, 9(47):28702-28716 Supplemental Materials.
Oseledchyk, Anton, Lysis-independent potentiation of immune checkpoint blockade by oncolytic virus, Oncotarget, 2018, 28702-28716, 9(47).
Overwijk, Willem W., Tumor Regression and Autoimmunity after Reversal of a Functionally Tolerant State of Self-reactive CD8+ T Cells, The Journal of Experimenetal Medicine, 2003, 568-580, vol. 198, No. 4.
Park, Man-Seong, Engineered viral vaccine constructs with dual specificity: Avian influenza and Newcastle disease. Proc. Natl. Acad. Sci. (USA), 2006, 8203-8208, 103.
Park, Man-Seong, Newcastle Disease Virus V Protein is a Determinant of Host Range Restriction, Journal of Virology, 2003, 9522-9532, vol. 77, No. 17.
Pecora, AL, et al., Phase I Trial of intravenous Administration of PV701, an Oncolytic Virus, in Patients with Advanced Solid Cancers, Journal of Clinical Oncology, 2002, pp. 2251-2266, 20(9).
Peeters, Ben P.H., Generation of a recombinant chimeric Newcastle disease virus vaccine that allows serological differentiation between vaccinated and infected animals, Vaccine, 2001, 1616-1627, 19.
Peeters, BPH, et al., Rescue of Newcastle Disease Virus from Cloned cDNA: Evidence that Cleavability of the Fusion Protein is a Major Determinant for Virulence, Journal of Virology, 1999, pp. 5001-5009, 73(6).
Phuangsab, Anan, Newcastle disease virus therapy of human tumor xenografts: antitumor effects of local or systemic administration, Cancer Letters, 2001, 27-36, 172.
Plitt, Tamar, Cancer therapy with Newcastle disease virus: rationale for new immunotherapeutic combinations, Clinical Investigation, 2015, 75-87, 5(1).
Pühler, F. et al., Generation of a recombinant oncolytic Newcastle disease virus and expression of a full IgG antibody from two transgenes, Gene Therapy, 2008, pp. 371-383, 15.
Quetglas, Jose L, Virotherapy with a Semliki Forest Virus-Based Vector Encoding IL 12 Synergizes with PD-1/PD-L1 Blockade, Cancer Immunology Research, 2015, 449-454, 3(5).
Quezada, Sergio A., CTLA4 blockade and GM-CSF combination immunotherapy alters the intratumor balance of effector and regulatory T cells, The Journal of Clinical Investigation, 2006, 1935-1945, vol. 116, No. 7.
Quinn and Trevor, Rapid Quantitation of Recombinant Retrovirus Produced by Packaging Cell Clones, BioTechniques, 1997, 1038 1044, 23(6).

Ribas, Antoni, Oncolytic Virotherapy Promotes Intratumoral T Cell Infiltration and Improves Anti-PD-1 Immunotherapy, Cell, 2017, 1109-1119, 170(6).
Robbins, Paul F., Human tumor antigens recognized by T cells, Curr. Opin. Immunol., 1996, 628-636, 8(5).
Robert, Caroline, Ipilimumab plus Dacarbazine for Previously Untreated Metastatic Melanoma, The New England Journal of Medicine, 2011, 2517-2526, 364(26).
Sapoznik, Sivan, Novel Anti-Melanoma Immunotherapies: Disarming Tumor Escape Mechanisms, Clinical and Developmental Immunology, 2012, 1-10, vol. 2012, Article ID 818214.
Schirrmacher, V., et al., Antitumor effects of Newcastle Disease Virus in vivo: Local versus systemic effects, International Journal of Oncology, 2001, pp. 945-952, 18.
Schirrmacher, Volker, Newcastle Disease Virus: A Promising Vector for Viral Therapy, Immune Therapy, and Gene Therapy of Cancer, Methods in Molecular Biology, 2009, 565-605, 542.
Scott, Jamie K., Searching for Peptide Ligands with an Epitope Library, Science, 1990, 386-390, 249(4967).
Seliger, Barbara, Characterization of the Major Histocompatibility Complex Class I Deficiencies in B16 Melanoma Dells, Cancer Research, 2001, 1095-1099, 61.
Seppi, T., Direct Determination of Oxygen by HPLC. 2. Chamber and Sample Application System for Determination of O(2) at Trace Levels, Analytical Chemistry, 1997, 4476-4481, vol. 69, No. 21.
Shafren, Darren R., A Decay-Accelerating Factor-Binding Strain of Coxsackievirus B3 Requires the Coxsackievirus-Adenovirus Receptor Protein to Mediate Lytic Infection of Rhabdomyosarcoma Cells, Journal of Virology, 1997, 9844-9848, 71(12).
Shafren, Darren R., Coxsackievirus A21 Binds to Decay-Accelerating Factor but Requires Intercellular Adhesion Molecule 1 for Cell Entry, Journal of Virology, 1997, 4736-4743, 71(6).
Shafren, Darren R., Coxsackieviruses B1, B3, and B5 Use Decay Accelerating Factor as a Receptor for Cell Attachment, Journal of Virology, 1995, 3873-3877, 69(6).
Shafren, Darren R., Mouse Cells Expressing Human Intercellular Adhesion Molecule-1 Are Susceptible to Infection by Coxsackievirus A21, Journal of Virology, 1997, 785-789, 71(1).
Shafren, Darren R., Oncolysis of human ovarian cancers by Echovirus Type 1, Int. J. Cancer, 2005, 320-328, 115(2).
Sharma, Sonia, Triggering the Interferon Antiviral Response Through an IKK-Related Pathway, Science, 2003, 1148-1151, 300.
Shenk, Thomas, Adenoviridae: The Viruses and Their Replication, Fundamental Virology, 1996, 979-1016, Third Edition, Chapter 30.
Shim, Kevin G., Inhibitory Receptors Induced by VSV Viroimmunotherapy Are Not Neccessarily Targets for Improving Treatment Efficacy, Molecular Therapy, 2017, 962-975, 25(4).
Silberhumer, Gerd R., Genetically Engineered Oncolytic Newcastle Disease Virus Effectively Induces Sustained Remission of Malignant Pleural Mesothelioma, Molecular Cancer Therapeutics, 2010, 2761-2769, 9(10).
Simpson, Tyler R., Regulation of CD4 T cell activation and effector function by inducible costimulator (ICOS), Current Opinion in Immunology, 2010, 326-332, 22(3).
Sinkovics, Joseph G., Newcastle disease virus (NDV): brief history of its oncolytic strains, Journal of Clinical Virology, 2000, 1-15, 16.
Skelding, Kathryn A., Enhanced oncolysis mediated by Coxsackievirus A21 in combination with doxorubicin hydrochloride. Invest New Drugs, 2012, 568-581, 30(2).
Skelding, Kathryn A., Systemic targeting of metastatic human breast tumor xenografts by Coxsackievirus A21, Breast Cancer Res Treat., 2009, 21-30, 113(1).
Song, Kyo Young, Antitumor efficacy of viral therapy using genetically engineered Newcastle disease virus [NDV(F3aa)-GFP] for peritoneally disseminated gastric cancer, J Mol Med, 2010, 589-596, 88(6).
Spranger, Stefani, Up-Regulation of PD-L1, IDO, and T(regs) in the Melanoma Tumor Microenvironment is Driven by CD8+ T Cells, Science Translational Medicine, 2013, [200ra116] 1-10, vol. 5, Issue 200.
Swann, Jeremy B., Type IIFN Contributes to NK Cell Homeostasis, Activcation, and Antitumor Function, The Journal of Immunology, 2007, 7540-7549, 178(12).

(56) References Cited

OTHER PUBLICATIONS

Swayne, D.E., et al, Recombinant paramyxovirus Type 1-avian Influenza H7 Virus as a Vaccine for Protection of Chickens against Influenza and Newcastle Disease, Avian Diseases, 2003, pp. 1047-1050, vol. 47.
Tumeh, Paul C., PD-1 blockade induces responses by inhibiting adaptive immune resistance, Nature, 2014, 568-571, (attached Extended Data Figures 1-6 and Extended Data Tablets 1-4), 515(7528).
Turk, Mary Jo, Concomitant Tumor Immunity to a Poorly Immunogenic Melanoma is Prevented by Regulatory T Cells, The Journal of Experimental Medicine, 2004, 771-782, 200(6).
Tuve, Sebastian, In situ adenovirus vaccination engages T effector cells against cancer, Vaccine, 2009, 4225-4239, 27.
Vail, David M., Spontaneously Occurring Tumors of Companion Animals as Models for Human Cancer, Cancer Investigation, 2000, 781-792, 18.
Velu, Vijayakumar, Role of PD-1 co-inhibitory pathway in HIV infection and potential therapeutic options, Retrovirology, 2015, 1-17, 12:14.
Verma, Inder M., Gene therapy—promises, problems and prospects, Nature, 1997, 239-242, 389.
Vigil, Adam, Recombinant Newcastle Disease Virus as a Vaccine Vector for Cancer Therapy, Molecular Therapy, 2008, 1883-1890, 16(11).
Vigil, Adam, Use of Reverse Genetics to Enhance the Oncolytic Properties of Newcastle Disease Virus, Cancer Research, 2007, 8285-8292, 67(17).
Vlasak, Josef, Use of flow cytometry for characterization of human cytomegalovirus vaccine particles, Vaccine, 2016, 2321-2328, 34.
Waitz, Rebecca, Potent Induction of Tumor Immunity by Combining Tumor Cryoablation with Anti-CTLA-4 Therapy, Cancer Research, 2012, 430-439, 72(2).
Wakamatsu, EI, Convergent and divergent effects of costimulatory molecules in conventional and regulatory CD4+ T cells, PNAS, 2013, 1023-1028, 110(3).
Wakamatsu, Nobuko, The Effect on Pathogenesis of Newcastle Disease Virus LaSota Strain from a Mutation of the Fusion Cleavage Site to a Virulent Sequence, Avian Diseases, 2006, 483-488, 50(4).
Walter, Michael J., Targeted Inhibition of Interferon-gamma-dependent Intercellular Adhesion Molecule-1 (ICAM-1) Expression Using Dominant-Negative Statl, Journal of Biological Chemistry, 1997, 28582-28589, 272(45).
Walter, Robert J., Two Avirulent, Lentogenic Strains of Newcastle Disease Virus are Cytotoxic for Some Human Pancreatic Tumor Lines in Vitro, Journal of the Pancreas, 2012, 502-513, 13(5).
Wang, Bailiang, A Novel, Clinically Relevant Animal Model of Metastatic Pancreatic Adenocarcinoma Biology and Therapy, International Journal of Pancreatology, 2001, 37-46, 29(1).
Weber, Friedemann, Viral suppression of the interferon system, Biochimie, 2007, 836-842, 89(6-7).
Wilden, Holger, Expression of RIG-I, IRF3, IFN-beta and IRF7 determines resistance or susceptibility of cells to infection by Newcastle Disease Virus, International Journal of Oncology, 2009, 971-982, 34(4).
Wold, William S.M., Adenovirus Vectors for Gene Therapy, Vaccination and Cancer Gene Therapy, Curr. Gene Therapy, 2013, 421-433, 13(6).
Woller, Norman, Oncolytic viruses as anticancer vaccines, Frontiers in Oncology, 2014, 1-13, 4(188).
Yamaki, Minoru, The potential of recombinant vesicular stomatitis virus-mediated virotherapy against metastatic colon cancer, International Journal of Molecular Medicine, 2013, 299-306, 31.
Yao, Sheng, Reviving exhausted T lymphocytes during chronic virus infection by B7-H1 blockade, Trends in Molecular Medicine, 2006, 244 246, 12(6).
Yoneyama, Mitsutoshi, The RNA helicase RIG-I has an essential function in double-stranded RNA-induced nnate antiviral responses, Nature Immunology, 2004, 730-737, 5.

Zamarin, D., Genetically engineered Newcastle disease virus for malignant melanoma therapy, Gene Therapy, 2009, 796-804, 16(6).
Zamarin, Dmitriy, Enhancement of Oncolytic Properties of Genetically-Engineered Fusogenic Newcastle Disease Mirus through Antagonism of Cellular Innate Immune Responses, Molecular Therapy, 2008, Abstract #43, 16 (Suppl. 1).
Zamarin, Dmitriy, Enhancement of Oncolytic Properties of Recombinant Newcastle Disease Virus Through Antagonism of Cellular Innate Immune Responses, The Journal of the American Society of Gene Therapy, 2009, 697-706, 17(4).
Zamarin, Dmitriy, Localized Oncolytic Virotherapy Overcomes Systemic Tumor Resistance to Immune Checkpoint Blockade Immunotherapy, Science Translational Medicine, 2014, 1-13, vol. 6, Issue 226, 226ra32.
Zamarin, Dmitriy, Localized Oncolytic Virotherapy Overcomes Systemic Tumor Resistance to Immune Checkpoint Blockade Immunotherapy, Science Translational Medicine, 2014, 226ra32 (pp. 1-96—Supplemental Material, Figures and Tables), 6(226).
Zamarin, Dmitriy, Oncolytic Newcastle disease virus for cancer therapy: old challenges and new directions, Future Microbiology, 2012, 347-367, 7.
Zamarin, Dmitriy, PD-L1 in tumor microenvironment mediates resistance to oncolytic immunotherapy, The Journal of Clinical Investigation, 2018, 1413-1428, 128(4).
Zamarin, Dmitriy, Potentiation of immunomodulatory antibody therapy with oncolytic viruses for treatment of Cancer, Molecular Therapy-Oncolytics, 2014, 1-10, 1, 14004.
Zhang, Wei-Wei, Anti-Oncogene and Tumor Suppressor Gene Therapy-Examples from a Lung Cancer Animal Model, In Vivo, 1994, 755-769, 8.
Zimmer, Gert, A Chimeric Respiratory Syncytial Virus Fusion Protein Functionally Replaces the F and HN Glycoproteins in Recombinant Sendai Virus, Journal of Virology, 2005, 10467-10477, 79(16).
Zitvogel, Laurence, Type I interferons in anticancer immunity, Nature Reviews Immunology, 2015, 405-414, 15.
A Safety Study of Two Intratumoural Doses of Coxsackievirus Type A21 in Melanoma Patients (PSX-X03), First Posted Date: Feb. 21, 2007, clinicaltrials.gov.
A Study of Intratumoral CAVATAK™ in Patients With Stage IIIc and Stage IV Malignant Melanoma (VLA-007 CALM ) (CALM), First Posted Date: Oct. 25, 2010, clinicaltrials.gov.
A Study of the Intratumoural Administration of CAVATAK to Head and Neck Cancer Patients (VLA-X06) (VLA-X06), First Posted Date: Jan. 30, 2009, clinicaltrials.gov.
Barbara Merelli et al., Targeting the PD1/PD-L1 axis in melanoma: Biological rationale, clinical challenges and opportunities, Critical reviews in Oncology/Hematology, 2014, 140-165, 89-1.
Blanchard, et al., Vaccines Against Advanced Melanoma, Clinics in Dermatology, 2013, 179-190, 31-2.
Brahmer et al., Safety and Activity of Anti-PD-L1 Antibody in Patients with Advanced Cancer, The New England Journal of Medicine, 2012, pp. 2455-3465, vol. 366, No. 26.
Caroline Roberts, Ipilimumab plus Dacarbazine for Previously Untreated Metastatic Melanoma, The New England Journal of Medicine, 2011, 2517-2526—vol. 362, No. 26 (Jun. 30, 2011).
CAVATAK in Patients With Stage IIIc or IV Malignant Melanoma to Extend Dosing to 48 Weeks (VLA-008 CALM Ext) (CALMext), First Posted Date: Jul. 10, 2012, clinicaltrials.gov.
Chumakov, PM et al., Oncolytic Enteroviruses, Molecular Biology, 2012, 639-650, 46(5).
Coxcackie Virus A21 Administered intravenously (IV) for Solid Tumour Cancers (PSX-X04) (PSX-X04), First Posted Date: Mar. 14, 2008, clinicaltrials.gov.
Curran et al., PD1 and CTLA4 combination blockade expands infiltrating T cells and reduces regulatory T adn myeloid cells within B16 melanoma tumors, PNAS, 2010, pp. 4275-4280, vol. 107.
CVA21 and Pembrolizumab in NSCLC & Bladder Cancer (VLA-009 STORM/KEYNOTE-200) (STORM), First Posted Date: Jan. 23, 2014, clinicaltrials.gov.
Eisenhauer et al., New Response Evaluation Criteria in Solid Tumours: Revised RECIST Guideline (Version 1.1), European Journal of Cancer, 2009, 228-247, 45.

(56) References Cited

OTHER PUBLICATIONS

Gao, Y et al, Recombinant vesicular stomatitis virus targeted to Her2/neu combined with anti-CTLA4 antibody eliminates implanted mammary tumors, Cancer Gene Therapy, 2009, 44-52, 16.
Garbe, et al., Systematic Review of Medical Treatment in Melanoma:, The Oncologist, 2011, 5-24, 16-1.
Gough G. Au et al., Oncolysis of vascular malignant human melanoma tumors by Coxsackievirus A21, Int. J. Oncol., 2005, 1471-1476, 26.
Gough G. Au, Oncolytic Coxsackievirus A21 as a novel therapy for multiple myeloma, British Journal of Haematology, Apr. 2007, 133-141, 137-2.
Intratumoral Cavatak (CVA21) and Ipilimumab in Patients with Advanced Melanoma (VLA-013 MITCI) (MITCI), First Posted Date: Dec. 4, 2014, clinicaltrials.gov.
Intratumoural Administration of Coxsackievirus A21 for the Control of Malignant Melanoma (PXS-X02) (PXS-X02), First Posted Date: Oct. 10, 2005, clinicaltrials.gov.
Mary E. Keir, et al., PD-1 and its Ligands in Tolerance and Immunity, Annu. Rev. Immunol., 2008, 677-704, 26.
Ott, et al., CTLA-4 and PD-1/PD-L1 Blockade: New Immunotherapeutic Modalities with Durable Clinical Benefit in Melanoma Patients, Clin.Cancer Res., 2013, 5300-5309, 19.
Puzanov, I et al., Phase 1 results of a phase 1b/2, multicenter, open-label trial to evaluate safety and efficacy of talimogene laherparepvec (T-VEC) and ipilimumal (ipi) vs ipi alone in previously untreated, unresected stage IIIB-IV melanoma, Journal for ImmunoTherapy of Cancer, 2013, 84, 1 (Suppl. 1).
Quah, MY et al, Abstract 2341: Elevated immune activity following an anticancer combination therapy of a novel oncolytic immunotherapeutic agent, CAVATAK (Coxsackievirus A21), and immune checkpoint blockade, Cancer Research, 2016, 1-2, Suppl. 2341, American Association for Cancer Research.
Quay, M et al., Immune-checkpoint blockade in combination with a novel oncolytic immunotherapeutic agent, Coxsackievirus A21, significantly reduces tumor growth and tumor rechallenge, European Journal of Cancer, 2015, S106, 51 (Suppl 3).
Safety and Clinical Activity of CAVATAK™ Alone or With Low Dose Mitomycin C in Non-muscle Invasive Bladder Cancer (CANON), First Posted Date: Dec. 12, 2014, clinicaltrials.gov.
Sharpen, DR et al., Systemic Therapy of Malignant Human Melanoma Tumors by a Common Cold-Producing Enterovirus, Coxsackievirus, Clinical Cancer Research, The American Association for Cancer Research, 2004, 53-60, 10(1).
Stephen Hodi, et al., Improved Survival with Ipilimumab in Patients with Metastatic Melanoma, The New England Journal of Medicine, Aug. 19, 2010, 711-723, 363-8.

Topalian et al., Safety, Activity, and Immune Correlates of Anti-PD-1 Antibody in Cancer, New Eng. J. Med., 2012 2443-2454, 366(26).
U.S. Office Action in connection with U.S. Appl. No. 15/121,517, dated, Jul. 11, 2017.
Zamarin, D et al., Localized oncolytic virotheraphy inflames distant tumors and synergizes with immune checkpoint blockade leading to systemic tumor rejection, Journal for ImmunoTherapy of Cancer, 2013, 09, 1 (Suppl 1).
Assudani, D.P et al.: "*Immunotherapeuticpotential of DISC-HSV and OX4OL in cancer*"; Cancer Immunology Inimunotherapeutics, 2006. 55(1): 104-111. Abstract.
International Search Report dated Mar. 30, 2015, regarding PCT/AU2015/000111.
Selman, A. A. et al.: "*Anti-tumour therapeutic efficacy of OX4OL in murine tumour model*"; Vaccine, 2004, 22: 3585-3594.
Shafren, D. et al.: "*Combination of a novel oncolytic immunotherapeutic agent, CAVATAK (coxsackievirus A21) and immune-checkpoint blockade significantly reduces tumor growth and improves survival in an immune competent mouse melanoma model*"; Journal for ImmunoTherapy of Cancer, Nov. 2, 2014, 2(Suppl 3): (2 pages).
Clinical Trial—Posting Date: Jan. 21, 2014: A Phase 1, Dose-finding and Signal-seeking Study of the Safety and Efficacy of Intravenous CAVATAK, (Coxsackievirus A21, CVA21) Alone and in Combination with Cytotoxic Chemotherapy in Patients with Late Stage Solid Tumours (NSCLC, Castrate-resistant Prostate Cancer, Melanoma, Bladder Cancer), clinicaltrials.gov, 2014, pp. 1-5.
Clinical Trial—Posting Date: Jul. 25, 2016: A Phase 1, Dose-finding and Signal-seeking Study of the Safety and Efficacy of Intravenous CAVATAK, (Coxsackievirus A21, CVA21) Alone and in Combination with Cytotoxic Chemotherapy in Patients with Late Stage Solid Tumours (NSCLC, Castrate-resistant Prostate Cancer, Melanoma, Bladder Cancer), clinicaltrials.gov, 2016, pp. 1-5.
Office Action, U.S. Appl. No. 15/789,340, dated Jun. 14, 2019.
Fan, Daiming, Frontiers in Cancer Research, Xi'an Jiaotong University Press, 2004, 112-127, 4.
Hou, Jian-Gang, et al., Oncolytic viruses for cancer treatment, Journal of Microbes and Infection, 2009, 35-39, 4 (1).
Kageshita, Toshiro et al., Clinical Relevance of ICAM-1 Expression in Primary Lesions and Serum of Patients with Malignant Melanoma, Cancer Research, 1993, 4927-4932, 53.
Kuppner, M.C. et al., Cytokine regulation of intercellular adhesion molecule-1 (ICAM-1) expression on human glioblastoma cells, Clin. Exp. Immunol., 1990, 142-148, 81.
Maruo, Y. et al., ICAM-1 Expression and the Soluble ICAM-1 Level for Evaluating the Metastatic Potential of Gastric Cancer, Int. J. Cancer, 2002, 486-490, 100.

\* cited by examiner

|  | NTC<br>n = 4 | Saline + Control Ab<br>n = 7 | Saline + anti-PD-1<br>n = 7 | UV-CVA21 + Control Ab<br>n = 7 |
|---|---|---|---|---|
| # deaths/events | 0 | 7 | 6 | 6 |
| Median survival | Undefined | 28 | 31 | 30 |

|  | UV-CVA21 + anti-PD-1<br>n = 8 | CVA21 + Control Ab<br>n = 8 | CVA21 + anti-PD-1<br>n = 8 |
|---|---|---|---|
| # deaths/events | 7 | 6 | 6 |
| Median survival | 32 | 28 | 36.5 |

FIG. 7G

Table 9: Immune-competent animal model: Summary of mouse body weights (g) in each treatment group.

| Study Day | Group 1 NTC Mean | S.D. | n | Group 2 Saline + Control Ab Mean | S.D. | n | Group 3 Saline + anti-PD-1 Mean | S.D. | n | Group 4 UV CVA21 + Control Ab Mean | S.D. | n | Group 5 UV CVA21 + anti-PD-1 Mean | S.D. | n |
|---|---|---|---|---|---|---|---|---|---|---|---|---|---|---|---|
| -2 | 16.7 | ±1.2 | 4 | 16.8 | ±0.8 | 8 | 16.5 | ±0.8 | 8 | 15.8 | ±0.7 | 8 | 16.8 | ±1.1 | 8 |
| 0 | 16.9 | ±0.9 | 4 | 16.6 | ±0.8 | 8 | 16.5 | ±0.6 | 8 | 15.9 | ±0.7 | 8 | 16.6 | ±0.8 | 8 |
| 3 | 17.7 | ±0.9 | 4 | 16.8 | ±0.8 | 8 | 16.7 | ±0.7 | 8 | 16.3 | ±0.7 | 8 | 17.1 | ±0.9 | 8 |
| 5 | 17.8 | ±0.6 | 4 | 17.0 | ±0.8 | 8 | 17.2 | ±0.8 | 8 | 16.5 | ±0.7 | 8 | 17.2 | ±0.8 | 8 |
| 7 | 17.9 | ±0.4 | 4 | 17.4 | ±0.8 | 8 | 17.5 | ±0.6 | 8 | 17.0 | ±0.7 | 8 | 17.7 | ±0.9 | 8 |
| 10 | 18.1 | ±0.5 | 4 | 17.7 | ±0.9 | 8 | 17.9 | ±0.8 | 8 | 16.9 | ±1.2 | 8 | 17.9 | ±0.6 | 8 |
| 12 | 18.5 | ±0.6 | 4 | 18.1 | ±0.9 | 8 | 18.1 | ±0.9 | 8 | 17.4 | ±1.2 | 6 | 18.3 | ±1.0 | 8 |
| 14 | 18.7 | ±0.7 | 4 | 17.3 | ±1.0 | 7 | 17.3 | ±1.8 | 7 | 17.3 | ±1.0 | 6 | 18.1 | ±0.9 | 7 |
| 17 | 18.8 | ±0.7 | 4 | 18.1 | ±0.9 | 5 | 19.0 | ±0.9 | 4 | 17.2 | ±1.0 | 5 | 18.3 | ±0.9 | 7 |
| 19 | 18.9 | ±0.6 | 4 | 18.3 | ±0.9 | 5 | 18.9 | ±1.0 | 4 | 17.5 | ±1.1 | 5 | 18.6 | ±1.0 | 7 |
| 21 | 19.4 | ±0.5 | 4 | 18.4 | ±1.1 | 5 | 19.5 | ±1.1 | 4 | 17.9 | ±1.2 | 5 | 18.8 | ±1.0 | 7 |
| 24 | 19.1 | ±0.4 | 4 | 19.2 | ±1.0 | 4 | 19.4 | ±1.1 | 4 | 18.5 | ±1.1 | 5 | 19.3 | ±1.0 | 7 |
| 26 | 19.9 | ±0.2 | 4 | 19.7 | ±0.7 | 4 | 19.8 | | | 19.1 | ±1.5 | 5 | 19.8 | ±1.2 | 7 |
| 27 | | | | | | | | | | | | | | | |
| 28 | 19.3 | ±0.4 | 4 | 19.8 | ±0.6 | 4 | 19.7 | ±0.9 | 4 | 18.6 | ±0.4 | 5 | 19.9 | ±1.4 | 7 |
| 31 | 19.7 | ±0.2 | 4 | 20.5 | ±1.0 | 3 | 20.1 | ±1.3 | 4 | 19.0 | ±0.2 | 3 | 20.7 | ±1.7 | 6 |
| 32 | | | | | | | | | | 17.9 | ±0.0 | 1 | 20.3 | ±1.5 | 2 |
| 33 | 19.7 | ±0.6 | 4 | | | | 20.3 | ±1.5 | 3 | 20.1 | ±0.6 | 2 | 21.5 | ±2.2 | 4 |
| 34 | | | | | | | | | | | | | 20.5 | ±0.0 | 1 |
| 35 | 20.3 | ±0.4 | 4 | | | | 20.6 | ±1.7 | 3 | 20.9 | 0.0 | 1 | 21.3 | ±3.3 | 2 |
| 36 | | | | | | | | | | | | | | | |
| 37 | | | | | | | | | | | | | | | |
| 38 | 20.2 | ±0.4 | 4 | | | | 21.6 | ±2.0 | 3 | | | | 19.8 | ±0.0 | 1 |
| 40 | 20.7 | ±0.5 | 4 | | | | 22.2 | ±2.0 | 3 | | | | 19.6 | ±0.0 | 1 |
| 42 | 20.9 | ±0.9 | 4 | | | | 20.3 | ±0.0 | 1 | | | | 20.0 | ±0.0 | 1 |
| 45 | 21.0 | ±1.0 | 4 | | | | 21.1 | ±0.0 | 1 | | | | 20.4 | ±0.0 | 1 |

FIG. 7H

Table 10: Immune-competent animal model: Summary of mouse body weights in each treatment group.

|  | Group 6 CVA21 + Control Ab | | | Group 7 CVA21 + anti-PD-1 | | |
|---|---|---|---|---|---|---|
| Study Day | Mean | S.D. | n | Mean | S.D. | n |
| -2 | 15.6 | ± 0.9 | 8 | 17.0 | ± 1.2 | 8 |
| 0 | 15.6 | ± 0.9 | 8 | 17.0 | ± 1.1 | 8 |
| 3 | 15.9 | ± 1.1 | 8 | 17.4 | ± 0.7 | 8 |
| 5 | 16.3 | ± 1.1 | 8 | 17.5 | ± 1.0 | 8 |
| 7 | 16.8 | ± 1.0 | 8 | 17.9 | ± 1.1 | 8 |
| 10 | 16.8 | ± 1.1 | 8 | 18.5 | ± 1.2 | 8 |
| 12 | 17.1 | ± 1.3 | 8 | 18.7 | ± 1.3 | 8 |
| 14 | 16.8 | ± 1.2 | 7 | 18.4 | ± 1.0 | 8 |
| 17 | 17.3 | ± 1.4 | 7 | 18.6 | ± 1.3 | 8 |
| 19 | 17.5 | ± 1.2 | 7 | 18.8 | ± 1.2 | 8 |
| 21 | 17.7 | ± 1.4 | 7 | 19.0 | ± 1.5 | 8 |
| 24 | 17.9 | ± 1.7 | 7 | 19.2 | ± 1.1 | 8 |
| 26 | 18.9 | ± 1.5 | 5 | 19.6 | ± 1.4 | 8 |
| 27 | - | - | - | 18.3 | ± 0.0 | 1 |
| 28 | 19.3 | ± 1.0 | 4 | 19.8 | ± 1.4 | 7 |
| 31 | 18.4 | ± 0.2 | 3 | 20.2 | ± 1.8 | 7 |
| 32 | - | - | - | - | - | - |
| 33 | 19.2 | ± 0.3 | 2 | 19.9 | ± 0.8 | 7 |
| 34 | - | - | - | - | - | - |
| 35 | 20.2 | ± 0.3 | 2 | 19.9 | ± 1.2 | 5 |
| 36 | - | - | - | 16.2 | ± 0.0 | 1 |
| 37 | - | - | - | 16.1 | ± 0.0 | 1 |
| 38 | 21.0 | ± 0.0 | 2 | 21.2 | ± 0.8 | 3 |
| 40 | 21.7 | ± 0.0 | 1 | 21.6 | ± 2.6 | 3 |
| 42 | 22.4 | ± 0.0 | 1 | 22.2 | ± 2.7 | 2 |
| 45 | 24.7 | ± 0.0 | 1 | 21.6 | ± 2.3 | 2 |

FIG. 7I

Table 11: Table showing significance values (p) following statistical analysis of survival curve comparisons. Values of p < 0.05 are shaded.

|  | Saline + Control Ab | Saline + anti-PD-1 | UV-CVA21 + Control Ab | UV-CVA21 + anti-PD-1 | CVA21 + Control Ab | CVA21 + anti-PD-1 |
|---|---|---|---|---|---|---|
| Saline + Control Ab | - | 0.2219 | 0.2472 | 0.0475 | 0.3409 | 0.0014 |
| Saline + anti-PD-1 | 0.2219 | - | 0.7745 | 0.9488 | 0.847 | 0.4901 |
| UV-CVA21 + Control Ab | 0.2472 | 0.7745 | - | 0.7555 | 0.8866 | 0.0269 |
| UV-CVA21 + anti-PD-1 | 0.0475 | 0.9488 | 0.7555 | - | 0.6073 | 0.0149 |
| CVA21 + Control Ab | 0.3409 | 0.847 | 0.8866 | 0.6073 | - | 0.2141 |
| CVA21 + anti-PD-1 | 0.0014 | 0.4901 | 0.0269 | 0.0149 | 0.2141 | - |

FIG. 7J

PT 12-002: LOCAL INJECTED AND NON-INJECTED LESION RESPONSES

MALE WITH METASTATIC MELANOMA TO THE LEG. INJECTION IN LEG LESIONS.

PT 03-032: NON-INJECTED DISTANT VISCERAL LESION RESPONSE

MALE WITH METASTATIC MELANOMA TO LEFT NECK AND LUNGS. INJECTION IN LEFT NECK.

COMBINATION METHOD FOR TREATMENT OF CANCER

CROSS REFERENCE TO RELATED APPLICATIONS

This is a Continuation of application Ser. No. 15/121,517, filed Aug. 25, 2016 which is a 35 USC § 371 National Stage application of International Application No. PCT/AU2015/000111 filed Feb. 27, 2015, now pending; which claims the benefit under 35 USC § 119(a) to Australian Provisional Application Serial No. 2014900647 filed Feb. 27, 2014. The disclosure of each of the prior applications is considered part of and is incorporated by reference in the disclosure of this application.

BACKGROUND OF THE INVENTION

Field of the Invention

The present invention relates to methods of treating tumours comprising delivering an oncolytic virus or oncolytic viral RNA via direct injection or systemic administration to the tumour or cancer in combination with the co-administration of an immuno-stimulatory agent via the systemic route to a mammal.

INCORPORATION OF SEQUENCE LISTING

The material in the accompanying sequence listing is hereby incorporated by reference into this application. The accompanying sequence listing text file, name SPRUSON1160_1_Sequence_Listing.TXT, was created on Apr. 18, 2018, and is 1,100 bytes. The file can be assessed using Microsoft Word on a computer that uses Windows Os.

BACKGROUND INFORMATION

Several new immunotherapeutic approaches for melanoma treatment have shown promising results in recent clinical trials. The antibody based therapy, ipilimumab was approved by the U.S. Food and Drug Administration (FDA) in March 2011, having demonstrated improved overall survival in patients with metastatic melanoma in Phase III clinical trials. Ipilimumab (Trade name: Yervoy®, Bristol-Myers Squibb) is a monoclonal antibody that targets the protein cytotoxic T lymphocyte-associated antigen 4 (CTLA-4)(CD152). Signaling through CTLA-4 is known to have an inhibitory effect on cytotoxic T-lymphocytes (CTLs) and by blocking this inhibitory signal with ipilimumab, CTLs are able to successfully target the destruction of cancer cells. In melanoma patients, the overall survival with ipilimumab alone was 10.1 months compared to 6.4 months for patients treated with a glycoprotein 100 (gp100) peptide vaccine [Hodi, et al., 2010]. In phase III studies, the response rate of previously treated advanced melanoma patients was 11% following ipilimumab treatment alone, and 15% in ipilimumab plus dacarbazine therapy of treatment-naïve patients [Hodi, et al., 2010; Robert, et al., 2011]. In both of these trials, improved overall survival with ipilimumab was clearly shown, as evident by reductions in the probability of death by 34% (compared with vaccine) and 28% (compared with dacarbazine alone). When ipilimumab was used in combination with dacarbazine, the median duration of best overall response was 19.3 months compared with 8.1 months with dacarbazine monotherapy.

Another immune checkpoint molecule being targeted for the immunotherapy of cancer, is programmed cell death 1 (PD-1)(CD279) found on the surface of activated T cells, B cells and myeloid cells [Ken, et al., 2008]. When the molecule programmed cell death 1 ligand 1 (PD-L1) (CD274) or PDL-2 (CD273) binds to the PD-1 receptor, the T cell is inhibited thereby limiting potential anti-tumoural responses. Currently there are a range of antibodies designed to target PD-1 and PD-L1 as a means of stimulating anti-tumoural T cell immunity, namely nivolumab (BMS-936558, Bristol-Myers Squibb) and the anti-PD-L1 antibody BMS-936559 [Brahmer, et al., 2012; Topalian, et al., 2012]. These antibodies against PD-1 and PD-L1 have been used in a range of preclinical studies in combination with CTLA-4 and in Phase III human trials [Curran et al, 2010; Merelli, 2014; Ott et al, 2013].

Coxsackievirus A21 (CVA21) is a naturally occurring picornavirus that has the capacity to preferentially infect and destroy malignant cells bearing the virus-cell entry receptor intercellular adhesion molecule-1 (ICAM-1) and/or decay accelerating factor (DAF). Previously we have demonstrated the efficacy of CVA21 against melanoma cells in a range of pre-clinical xenograft models using immune-deficient mice, as well as against other cancers such as breast cancer, prostate cancer, colorectal cancer and ovarian cancer [Shafren, et al., 2004; Au, et al., 2005; Au et al., 2007; WO2001/037866]; and against hematologic cancers [WO/2006/017914].

There remains a need for new and improved methods for the treatment, alleviation, or prevention of cancer and for methods of improving survival in subjects with tumors or cancer.

SUMMARY OF INVENTION

The inventors propose that CVA21 infection and subsequent lysis of tumour cells, results in the release of cellular debris that contains melanoma antigens that stimulate anti-tumoural immunity, thereby acting as a personalised in situ cancer vaccine. First we established an immune-competent B16-ICAM-1 melanoma model where B16 cells, normally resistant to CVA21, were transfected with human ICAM-1 to make them permissive to infection. Given the generally poor induction of anti-tumoural immunity of most cancer vaccines [Blanchard, et al., 2013; Garbe, et al., 2011], we investigated the use of the immunostimulatory anti-PD-1 antibody in combination with CVA21 virotherapy and separately the use of the immune-stimulatory anti-CTLA-4 antibody in combination with CVA21 virotherapy, as well as the use of CVA21 virotherapy in combination with both anti-PD-1 antibody and anti-CTLA-4 antibody.

As demonstrated herein the use of immunostimulatory agents targetting immune checkpoint molecules, exemplified herein by the use of a murine anti-PD-1 antibody and a murine anti-CTLA-4 antibody, in combination with oncolytic CVA21 would be therapeutically beneficial in reducing tumour burden, rates of tumour ulceration and prolong survival in a murine B16-ICAM-1 model of melanoma.

In one aspect the invention provides a method for the treatment of cancer in a subject, the method comprising delivering an oncolytic virus or oncolytic viral RNA via direct injection to a tumor or systemic administration to the subject in combination with the co-administration of an immuno-stimulatory agent via the systemic route to the subject.

In one aspect the invention provides a method for the treatment of bladder cancer in a subject, the method comprising delivering an oncolytic virus or oncolytic viral RNA via direct injection to a tumor or systemic administration or intravesicular administration to the subject in combination with the co-administration of an immuno-stimulatory agent via the systemic route to the subject.

In an embodiment the oncolytic virus or oncolytic viral RNA is selected from the group consisting of Family Picornaviridae. In an embodiment the oncolytic virus or oncolytic viral RNA selected from the group consisting of Family Picornaviridae virus that bind to intercellular adhesion molecule-1 (ICAM-1) and/or decay-accelerating factor (DAF) on the surface of the tumour cell. In an embodiment the oncolytic virus or oncolytic viral RNA is selected from the group consisting of genus enterovirus that bind to intercellular adhesion molecule-1 (ICAM-1) and/or decay-accelerating factor (DAF) on the surface of the tumour cell. In an embodiment the enterovirus is a human enterovirus C. In an embodiment the oncolytic virus or oncolytic viral RNA is selected from the group consisting of Group A Coxsackievirus that bind to intercellular adhesion molecule-1 (ICAM-1) and/or decay-accelerating factor (DAF) on the surface of the tumour cell. In an embodiment the oncolytic virus or oncolytic viral RNA is Coxsackievirus A21.

In an embodiment the immuno-stimulatory agent is an agent that targets an immune checkpoint molecule selected from the group consisting of PD-1, PD-L1, PD-L2, CTLA-4, CD134, CD134L, CD137, CD137L, CD80, CD86, B7-H3, B7-H4, B7RP1, ICOS, TIM3, GAL9, CD28 or OX-40. In an embodiment the immunostimulatory agent is selected from the group consisting of an agent that specifically binds to the surface expressed PD-1, PD-L1, PD-L2, CTLA-4 or OX-40. In an embodiment the immunostimulatory agent is selected from the group consisting of monoclonal antibodies that specifically binds to the surface expressed PD-1, PD-L1, PD-L2, CTLA-4 or OX-40.

In an embodiment the method comprises delivering the oncolytic virus or oncolytic viral RNA via direct injection or systemic administration or intravesicular administration prior to the administration of an immuno-stimulatory agent via the systemic route.

In an embodiment the method comprises delivering the oncolytic virus or oncolytic viral RNA via direct injection or systemic administration or intravesicular administration following the administration of an immuno-stimulatory agent via the systemic route to the subject.

In an embodiment the treatment provides increased survival time for a subject compared to estimated survival time in the absence of said treatment. In an embodiment the treatment provides retardation of tumour growth compared to estimated tumour growth in the absence of said treatment.

In one aspect the invention provides use of oncolytic virus or oncolytic viral RNA for the manufacture of a medicament for the treatment of a subject having cancer, wherein said medicament is for use in combination with an immuno-stimulatory agent delivered via the systemic route to the subject, and wherein said medicament is for delivery via direct injection to the tumor or systemic administration to the subject.

In one aspect the invention provides use of oncolytic virus or oncolytic viral RNA for the manufacture of a medicament for the treatment of a subject having bladder cancer, wherein said medicament is for use in combination with an immuno-stimulatory agent delivered via the systemic route to the subject, and wherein said medicament is for delivery via direct injection to a tumor or systemic administration or intravesicular administration to the subject.

In an embodiment of said use, the oncolytic virus or oncolytic viral RNA is for administration to the tumour via direct injection or systemic or intravesicular administration prior to the administration of an immuno-stimulatory agent via the systemic route to the mammal. In an embodiment of said use, the medicament comprising an oncolytic virus or oncolytic viral RNA is for administration to the tumour via direct injection or systemic or intravesicular administration following the administration of an immuno-stimulatory agent via the systemic route to the mammal.

In one aspect the invention provides an oncolytic virus or oncolytic viral RNA for use in treatment of a subject having cancer, wherein said use is in combination with an immuno-stimulatory agent, wherein in said use the oncolytic virus or oncolytic viral RNA is administered to said subject via direct injection to a tumor or systemic administration to the subject and said immuno-stimulatory agent is administered via the systemic route to the subject.

In one aspect the invention provides an oncolytic virus or oncolytic viral RNA for use in treatment of a subject having bladder cancer, wherein said use is in combination with an immuno-stimulatory agent, wherein in said use the oncolytic virus or oncolytic viral RNA is administered to said subject via direct injection to a tumor or systemic administration or intravesicular administration to the subject and said immuno-stimulatory agent is administered via the systemic route to the subject.

In an embodiment the administration of said oncolytic virus or oncolytic viral RNA is prior to the administration of the immuno-stimulatory agent. In an embodiment the administration of said oncolytic virus or oncolytic viral RNA is following the administration of the immuno-stimulatory agent.

In an embodiment the mammal or subject is a human.

In an embodiment the cancer or tumour is selected from the group consisting of prostate cancer, breast cancer, ovarian cancer, lymphoid cancer, leukemia, brain cancer, lung cancer, colorectal cancer, thyroid cancer, renal cancer, adrenal cancer, liver cancer, stomach cancer, intestinal cancer, bladder cancer, cancer of the kidney, multiple myeloma, non-small cell lung cancer (NSCLC), pancreatic cancer, glioblastoma and melanoma.

In an embodiment the cancer or tumour is melanoma.

In an embodiment the cancer or tumor is metastatic cancer or a metastatic tumor.

BRIEF DESCRIPTION OF DRAWINGS

FIG. 7A-7J: Survival of C57BL/6 mice following treatment with either saline, UV-inactivated CVA21, CVA21 in combination with the control antibody or anti-PD-1 antibody. Survival curve comparisons between A) Saline+control Ab vs CVA21+control Ab, B) Saline+anti-PD-1 vs CVA21+anti-PD-1, C) Saline+control Ab vs Saline+anti-PD-1, D) CVA21+control Ab vs CVA21+anti-PD-1, E) Saline+control Ab vs CVA21+anti-PD-1, F) UV-CVA21+anti-PD-1 vs CVA21+anti-PD-1. The dotted lines show the 50% survival cut offs and corresponding median survival time, G) Saline+Control Ab vs Saline+anti-PD-1 vs UV-CVA21+Control Ab, H) Table 9: Immune-competent animal model: Summary of mouse body weights (g) in each treatment group, I) Table 10: Immune-competent animal model: Summary of mouse body weights (g) in each treatment group, J) Table 11: Table showing significance values (p) following statistical analysis of survival curve comparisons. Values of p<0.05 are shaded.

Figure 1A:
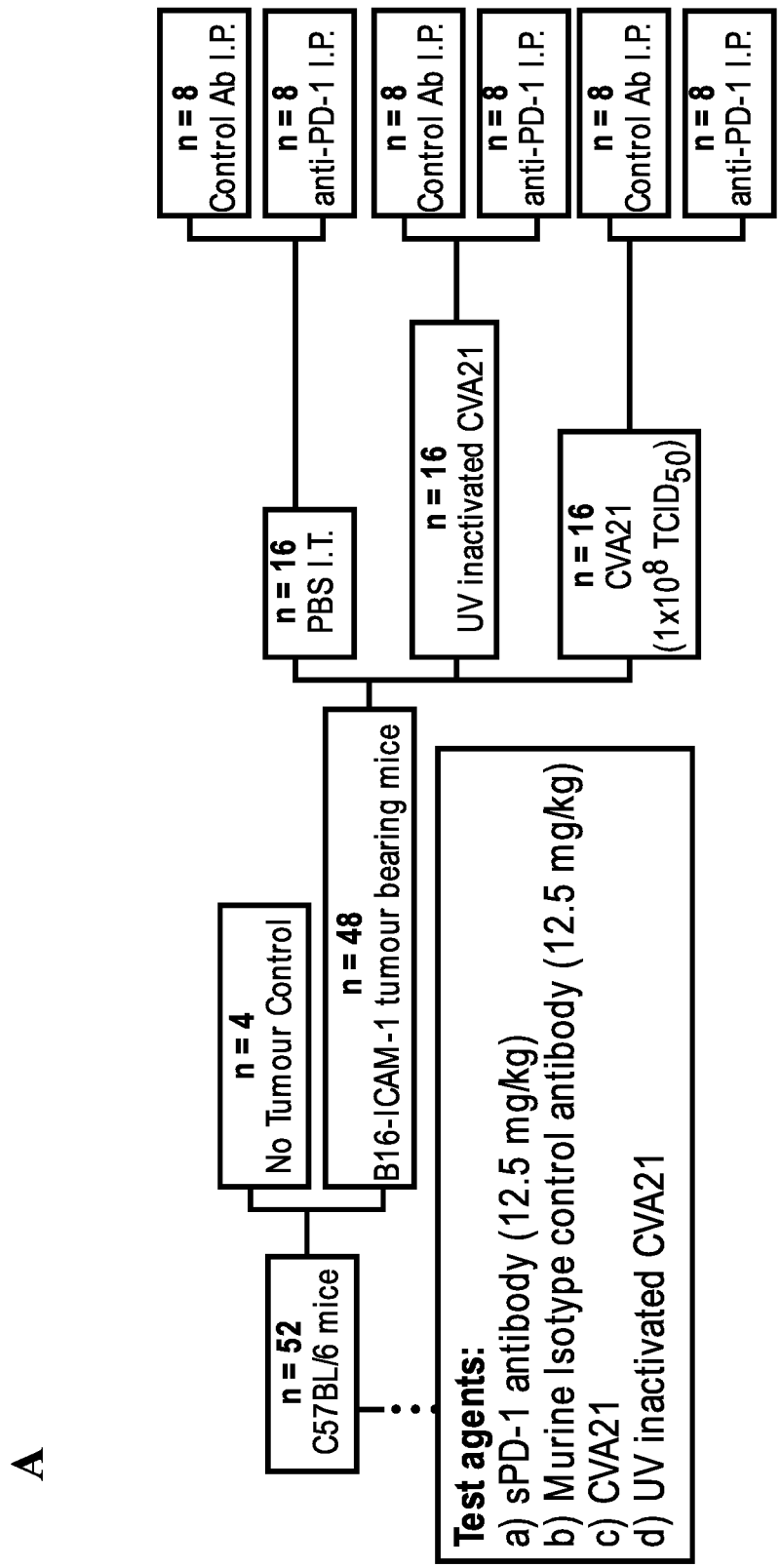
FIG. 1A-1B: Overview of immune-competent murine melanoma protocol. A) Flow diagram showing treatment groups. Animals were first treated with either CVA21 ($1 \times 10^8$ TCID 50 [$5 \times 10^9$ TCID 50/kg]) intratumourally, UV-inactivated CVA21 or saline, followed by intraperitoneal injections with the murine isotype control antibody or the anti-PD-1 antibody (12.5 mg/kg). B) Time line showing the schedule of treatments (green triangles and orange stars) and monitoring procedures. The experiment was terminated on day 45. (NTC=No Tumour Control).

| Abbreviations | |
|---|---|
| Ab | antibody |
| ACEC | Animal Care and Ethics Committee |
| ANOVA | Analysis of Variance |
| ATCC | American Type Culture Collection |
| BSA | bovine serum albumin |
| CI | Combination Index |
| $CO_2$ | carbon dioxide |
| CD | cluster of differentiation |
| CPE | cytopathic effect |
| CTL | cytotoxic T lymphocyte |
| CVA21 | Coxsackievirus A21 |
| DAF | decay-accelerating factor |
| $dH_2O$ | distilled water |
| DMEM | Dulbecco's Modified Eagle's Medium |
| DNA | deoxynucleotide phosphate |
| EtOH | ethanol |
| FCS | foetal calf serum |
| g | gamma |

-continued

| Abbreviations | |
|---|---|
| ICAM-1 | intercellular adhesion molecule-1 |
| i.p. | intraperitoneal |
| i.t. | intratumoral |
| i.v. | intravenous |
| irPFS | immune-related progression-free survival |
| MAb | monoclonal antibody |
| nAb | neutralising antibody |
| MOI | multiplicity of infection |
| PBS | phosphate buffered saline |
| PCR | polymerase chain reaction |
| PD-1 | programmed cell death 1 |
| PD-L1 | programmed cell death 1 ligand 1 |
| p.i. | post inoculation |
| p.t.i. | post tumour inoculation |
| RNA | ribonucleic acid |
| RPMI | Royal Park Memorial Institute |
| RT | room temperature |
| RT-PCR | reverse transcriptase-polymerase chain reaction |
| s.c. | subcutaneous |
| SCID | severe combined immunodeficient |
| SD | standard deviation |
| SE | standard error |
| sICAM-1 | soluble intercellular adhesion molecule-1 |
| $TCID_{50}$ | Tissue Culture Infectious Dose 50% |
| UV | ultraviolet |
| XTT | 2,3-Bis-(2-Methoxy-4-Nitro-5-Sulfophenyl)-2H-Tetrazolium-5-Carboxanilide |

| Units | |
|---|---|
| ° C. | degrees Celsius |
| d | day |
| g | gravitational force |
| g | gram |
| h | hour |
| L | liter |
| m | meter |
| M | Molar |
| min | minute |
| mol | mole |
| rpm | revolutions per minute |
| s | second |
| U | units |
| V | volts |
| v/v | volume per volume |
| w/v | weight per volume |

| Nucleotides | |
|---|---|
| A | adenine |
| C | cytosine |
| G | guanine |
| T | thymine |

| Prefixes | | |
|---|---|---|
| k | kilo | $10^3$ |
| m | milli | $10^{-3}$ |
| μ | micro | $10^{-6}$ |
| n | nano | $10^{-9}$ |
| p | pico | $10^{-12}$ |

DESCRIPTION OF EMBODIMENTS

The invention will now be described in more detail, including, by way of illustration only, with respect to the examples which follow.

The following are some definitions that may be helpful in understanding the description of the present invention. These are intended as general definitions and should in no way limit the scope of the present invention to those terms alone, but are put forth for a better understanding of the following description.

The methods of the invention typically involve administration of a therapeutically effective amount of the oncolytic virus or oncolytic viral RNA and of the immuno-stimulatory agent. The term "therapeutically effective amount" as used herein, includes within its meaning a non-toxic but sufficient amount the oncolytic virus or oncolytic viral RNA and of the immuno-stimulatory agent for use in the invention to provide the desired therapeutic effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

In the context of this specification, the term "treatment" and related terms such as "treating", "treated", and "treat" refer to any and all uses which remedy or alleviate a disease state or symptoms, prevent the establishment of disease, or otherwise prevent, hinder, retard, or reverse the progression of disease or other undesirable symptoms in any way whatsoever. For the avoidance of misunderstanding it is noted that "treatment" and related terms as used herein does not require complete cure or remission of the disease being treated.

In the context of this specification, the term "comprising" means "including principally, but not necessarily solely". Furthermore, variations of the word "comprising", such as "comprise" and "comprises", have correspondingly varied meanings.

To the extent permitted, the contents of documents referred to herein are incorporated by reference.

In the context of this specification, the term "subject" or "patient" includes humans and individuals of any species of social, economic or research importance including but not limited to members of the genus ovine, bovine, equine, porcine, feline, canine, primates, rodents. In preferred embodiments the subject or patient is a human.

Unless the context requires otherwise or specifically stated to the contrary, integers, steps, or elements of the invention recited herein as singular integers, steps or elements clearly encompass both singular and plural forms of the recited integers, steps or elements.

In the context of this specification, the singular encompasses also the plural except where the sepcifc context clearly indicates otherwise. For example, where it is stated that the invention includes methods for treatment of cancer by administration of an oncolytic virus or oncolytic viral RNA in combination with co-administration of an immuno-stimulatory agent, it will be understood that this encompasses the administration of one or more such viruses or viral RNAs and encompasses the administration of one or more immuno-stimulatory agents.

In the context of this specification, the term "about" when used in relation to a numerical value will be understood to convey the usual degree of variation known in the art for the measure being described. Where the art does not recognise a usual degree of variation for a measure or where it does and additional direction is nevertheless desirable, the term "about" as used herein will be understood to convey a variation of plus or minus 10% of the numerical value to which the term "about" is used.

Any description of prior art documents herein, or statements herein derived from or based on those documents, is not an admission that the documents or derived statements are part of the common general knowledge of the relevant art in Australia or elsewhere.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

In the context of this specification, where a numerical range is provided it will be understood to encompass the stated end points of the range and all values between those end points, including any sub-ranges within those endpoints.

The inventors herein demonstrate the use of immunostimulatory agents targetting immune checkpoint molecules, exemplified herein by the use of a murine anti-PD-1 antibody and a murine anti-CTLA-4 antibody, in combination with oncolytic CVA21 would be therapeutically beneficial in reducing tumour burden, rates of tumour ulceration and prolong survival in a murine B16-ICAM-1 model of melanoma. Whilst it would be expected that enhancing the immune system by the use of immuno-stimulating agents would disadvantage the efficacy of an oncolytic virus, for example by enhanced immune clearance or targeting of the virus, the inventors herein demonstrate that surprisingly and counter-intuitively the combination of oncolytic virus and immuno-stimulatory agent offers improved anti-tumor effects compared to either agent virus or immuno-stimulatory agent alone. The invention described herein thus provides a method of treating tumours comprising delivering an oncolytic virus or oncolytic viral RNA via direct injection or systemic administration to the tumour in combination with the co-administration of immuno-stimulatory agent via the systemic route to a mammal. Where the cancer desired to be treated is one for which a specific mechanism of delivery of virus or agent may be be advantageous, that method of delivery is preferred. For example, where the method isfor the treatment of bladder cancer or metastatic bladder cancer, administration of at least the virus or viral RNA is advantageously by the intravesicular route.

CVA21 is a member of the human enterovirus C (HEC) family of viruses. Other notable members of the HEC family include the Coxsackieviruses, for example CVA13, CVA15, and CVA18. Each of CVA13, CVA15, CVA18 and CVA21 have been demonstrated to have oncolytic effect in the treatment of various solid cancers, such as breast cancer, prostate cancer, colorectal cancer, ovarian cancer and melanoma (Shafren et al, 2004; Au et al., 2005; Au et al., 2007; WO2001/037866 filed 27 Nov. 2000 and entitled "A method of treating a malignancy in a subject and a pharmaceutical composition for use in same"; the contents of which is incorporated herein in its entirety by reference) as well as hematologic cancers such as multiple myeloma (WO/2006/017914 filed 22 Aug. 2005 and entitled "Methods and compositions for treatment of hematologic cancers", the contents of which is incorporated herein in its entirety by reference). Each interacts with the ICAM-1 receptor for infection of a host cell (Shafren et al, 1997) with decay accelerating factor (DAF) acting as a cooperative sequestration site (Shafren et al, 1997). Accordingly, the demonstration herein of a beneficial effect in a cancer model of the co-administration of CVA21 with immune-stimulatory agents will also apply to viruses functionally related to CVA21, such as CVA13, CVA15 and CVA18 and other human enterovirus C.

Any suitable source of the virus may be used in the methods of the invention. For example, various suitable strains of virus may be obtained from the American Type Culture Collection (ATCC), 10801 University Blvd., Manassas, Va. 20110-2209 USA, such as material deposited under the Budapest Treaty on the dates provided below, and is available according to the terms of the Budapest Treaty. Coxsackie group A virus, strain CVA13 ATCC No.: PTA-8854 Deposited 20 Dec. 10 2007; Coxsackie group A virus, strain CVA15 (G9) ATCC No.: PTA-8616 Date of Deposit: Aug. 15, 2007; Coxsackie group A virus, strain CVA1 8 ATCC No.: PTA-8853 Deposited 20 Dec. 2007; Coxsackie group A virus, strain CVA21 (Kuykendall) ATCC No.: PTA-8852 Deposited 20 Dec. 2007.

As described herein the methods encompass the viral agent being administered as an oncolytic virus and the viral agent being administered in the form of oncolytic viral RNA, such as viral RNA corresponding to CVA21. Methods for the use of oncolytic viral RNA in the treatment of cancer have been described in WO2006/074526 entitled "Method and composition for treatment of neoplasms", the contents of which are incorporated herein by reference.

Following infection, an oncolytic virus can kill a cancerous cell by direct lytic infection, induction of apoptosis or by initiating an immune response to viral antigens. An oncolytic virus is thus not limited to a single input dose and can undergo a multi-cycle infection, resulting in the production of large numbers of progeny virus. These progeny can spread either locally to adjacent tumour cells, or systemically to distant metastatic sites. This feature of oncolytic therapy is particularly attractive for the treatment of inaccessible tumours or un-diagnosed micro-metastases. The demonstration herein, for example, that intra-tumoral administration of CVA21 to a melanoma on the neck of a patient is associated with antitumour activity in both injected and distant non-injected lesions (FIG. 17), is consistent with a systemic effect occurring. As demonstrated herein intralesional CVA21 is a promising novel oncolytic immunotherapeutic agent for the treatment of unresectable Stage IIIC-IVM1c melanoma and the clinical study described herein under Example 5 study met its primary endpoint of irPFS at 6 months. CVA21 was well tolerated and exhibited both local and distant durable tumor responses.

Figure 18:
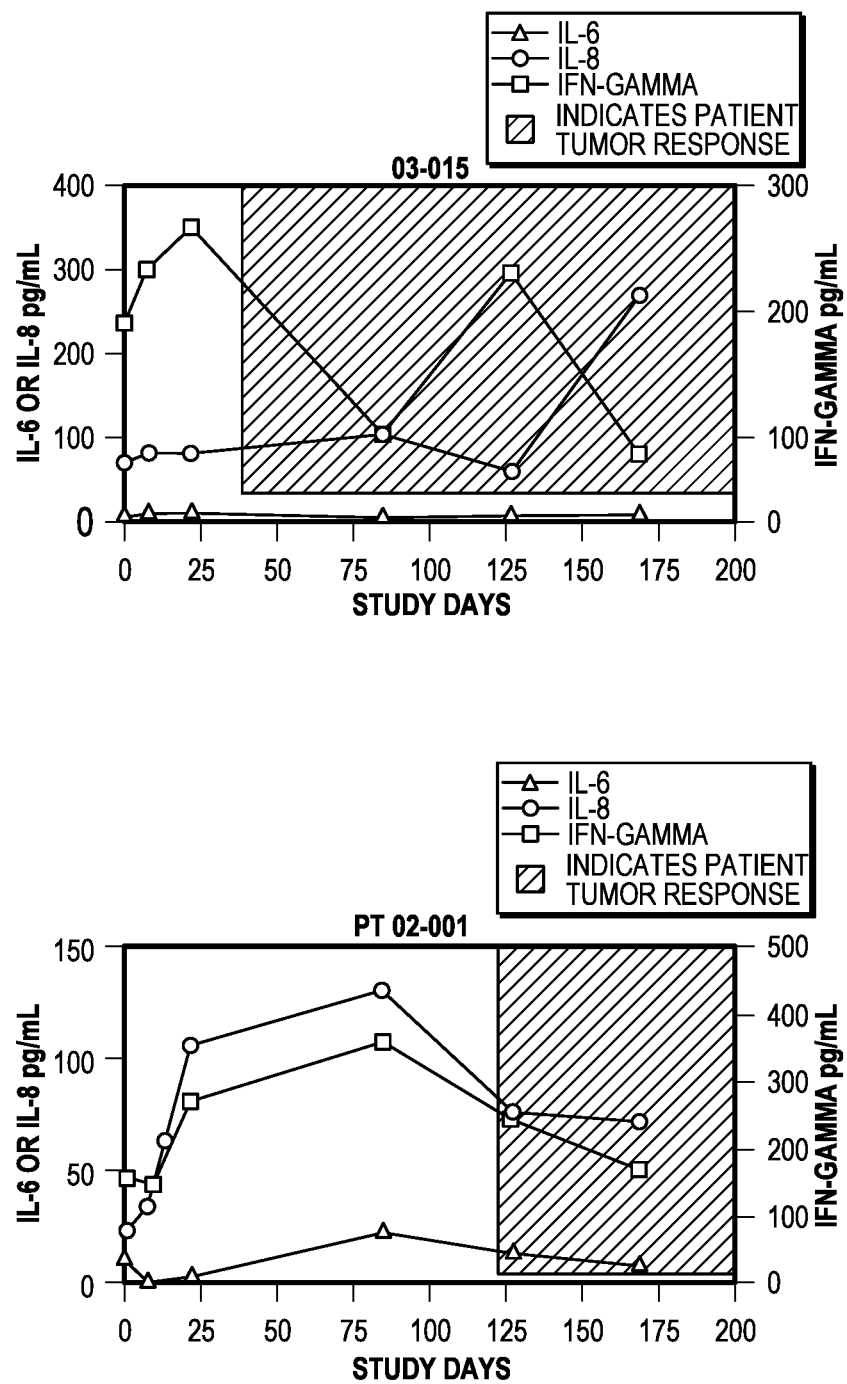
FIG. 18: CALM Phase II trial. Preliminary analysis: Serum cytokine activity (Patients with objective responses). Serum samples from individual patients were taken at the indicated times following the initial intratumoral CVA21 injection. Serum samples were assessed for inflammatory cytokine levels as per manufactures instructions by multiplex immunoassay using a Bio-Plex Pro™ Human Cytokine 17-plex Assay (#M50-00031YV) BioRad, Richmond, Va., USA. Patient tumour responses were assessed employing immune-related RECIST 1.1 criteria.
Figure 18:
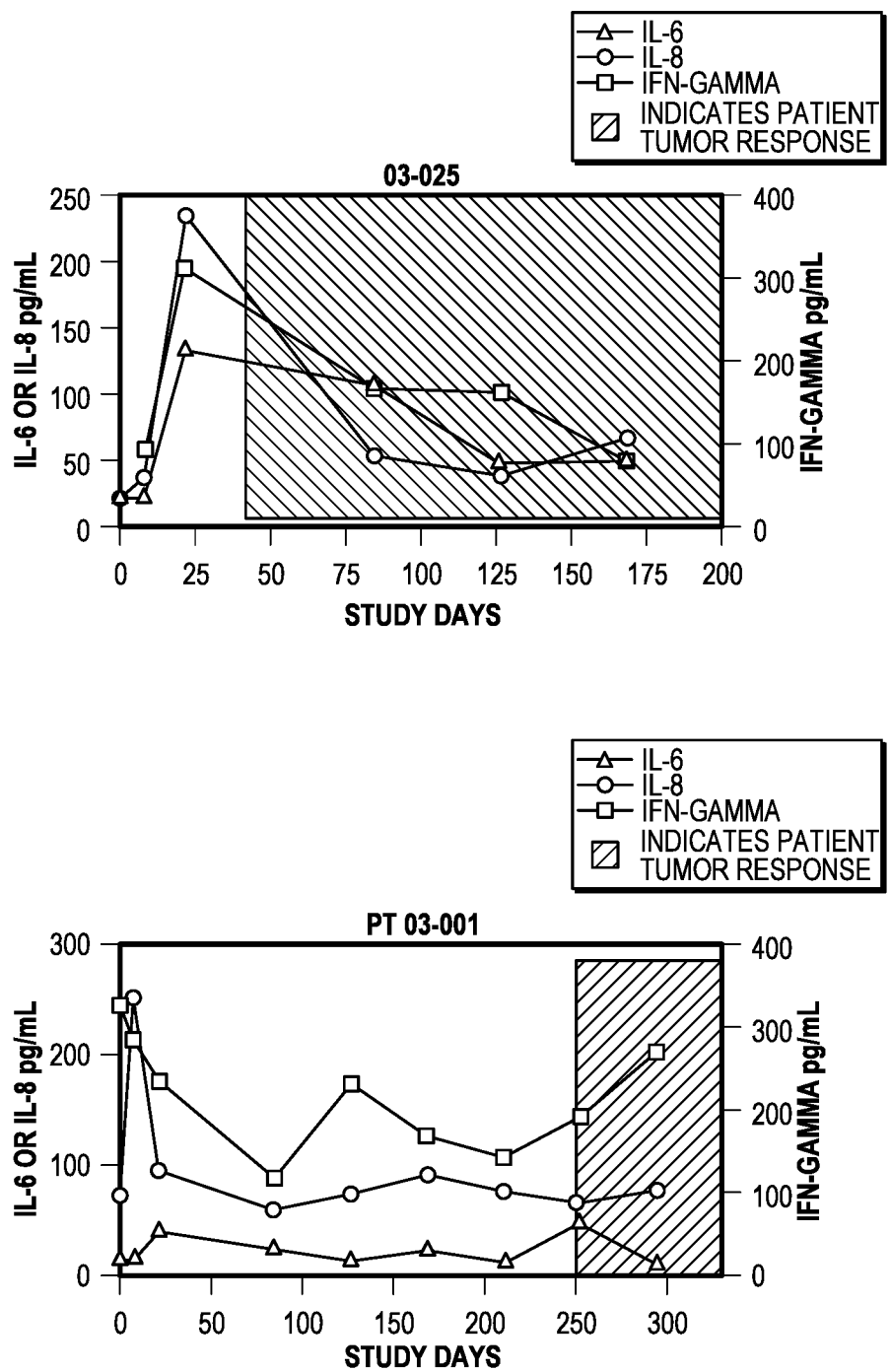
Figure 18:
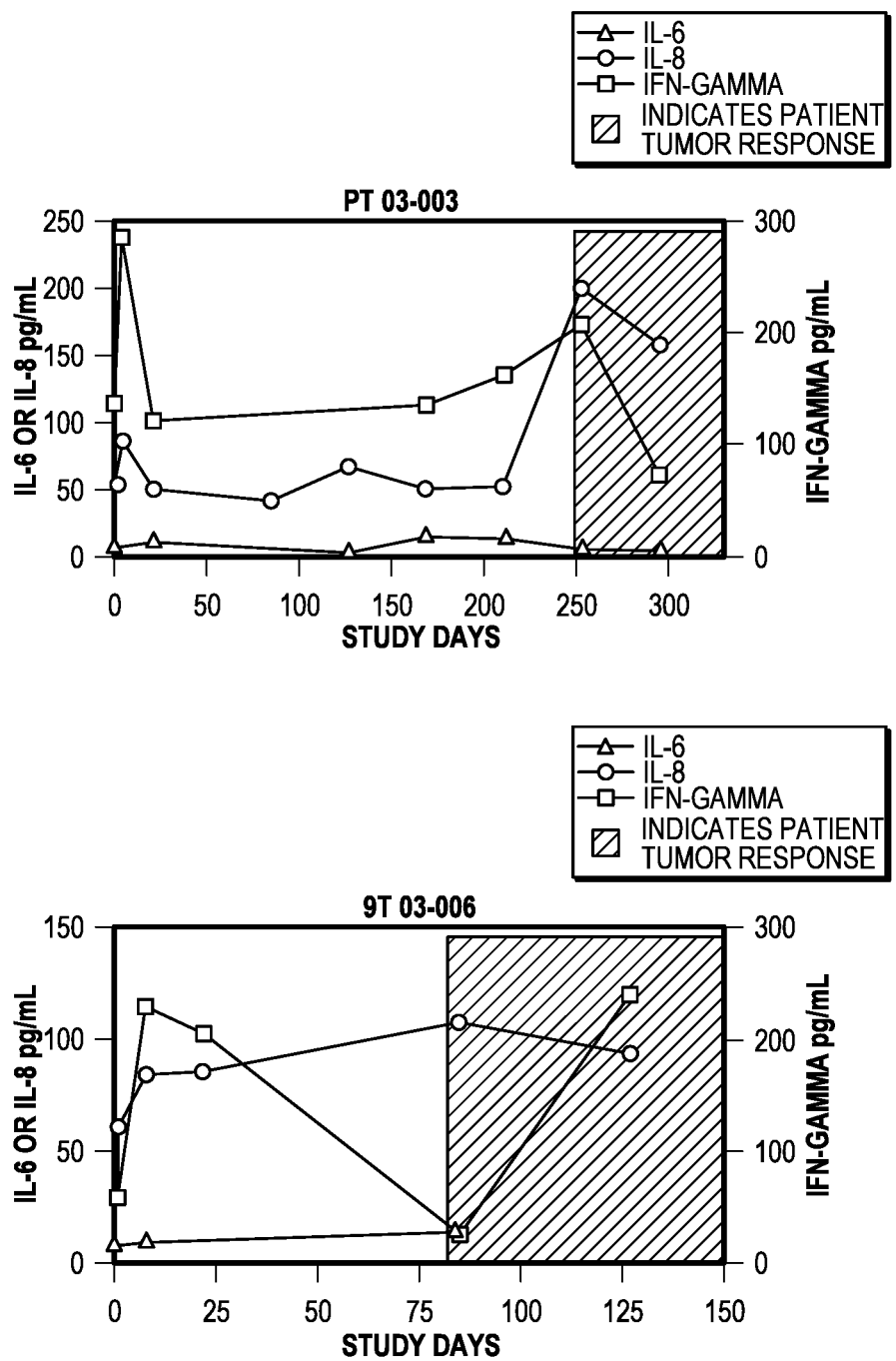
Figure 19:
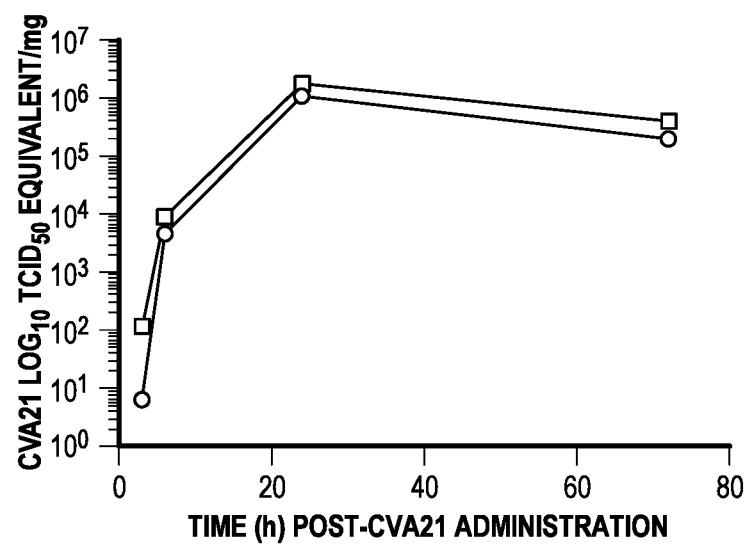
FIG. 19: Intravenous administered CVA21 (also noted on the figure as CAVATAK™) induces tumor cell gene expression changes. BALB mice were administered CVA21 or saline and sacrificed 3, 6, 24 and 72 h post-administration and analysed for gene expression (right four panels). CVA21 replication kinetics are shown in the left single panel.
Figure 19:
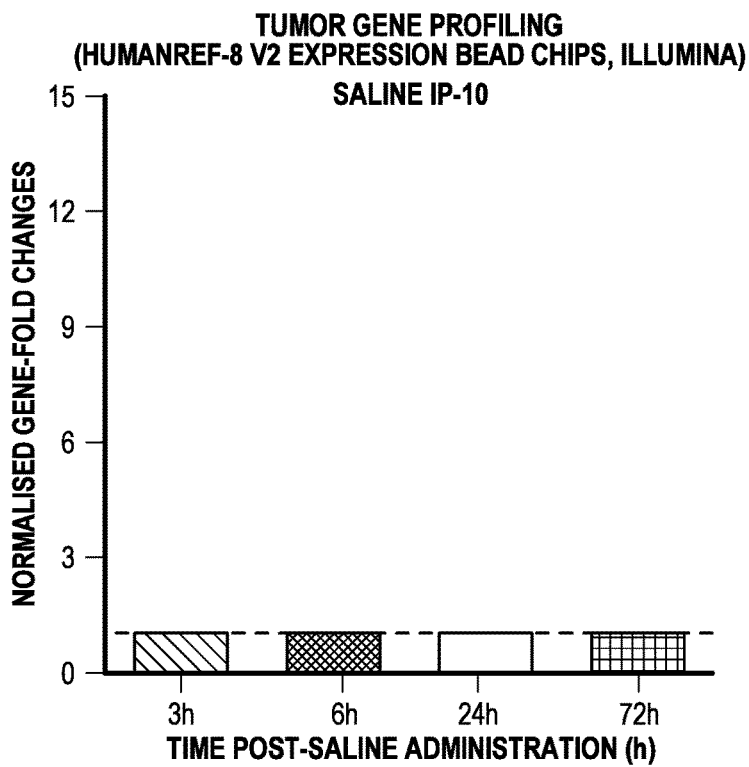
Figure 19:
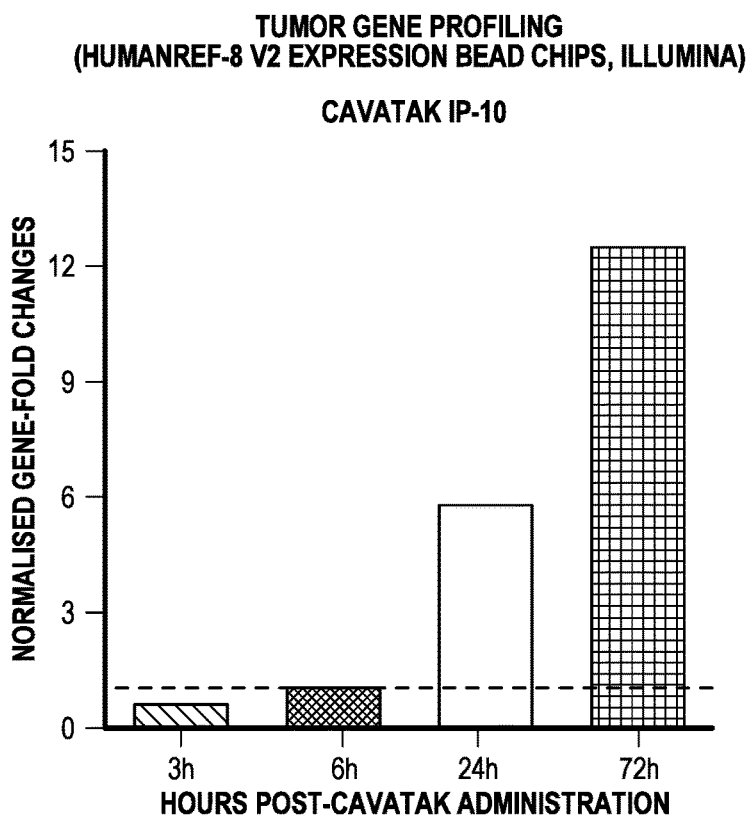
Figure 19:
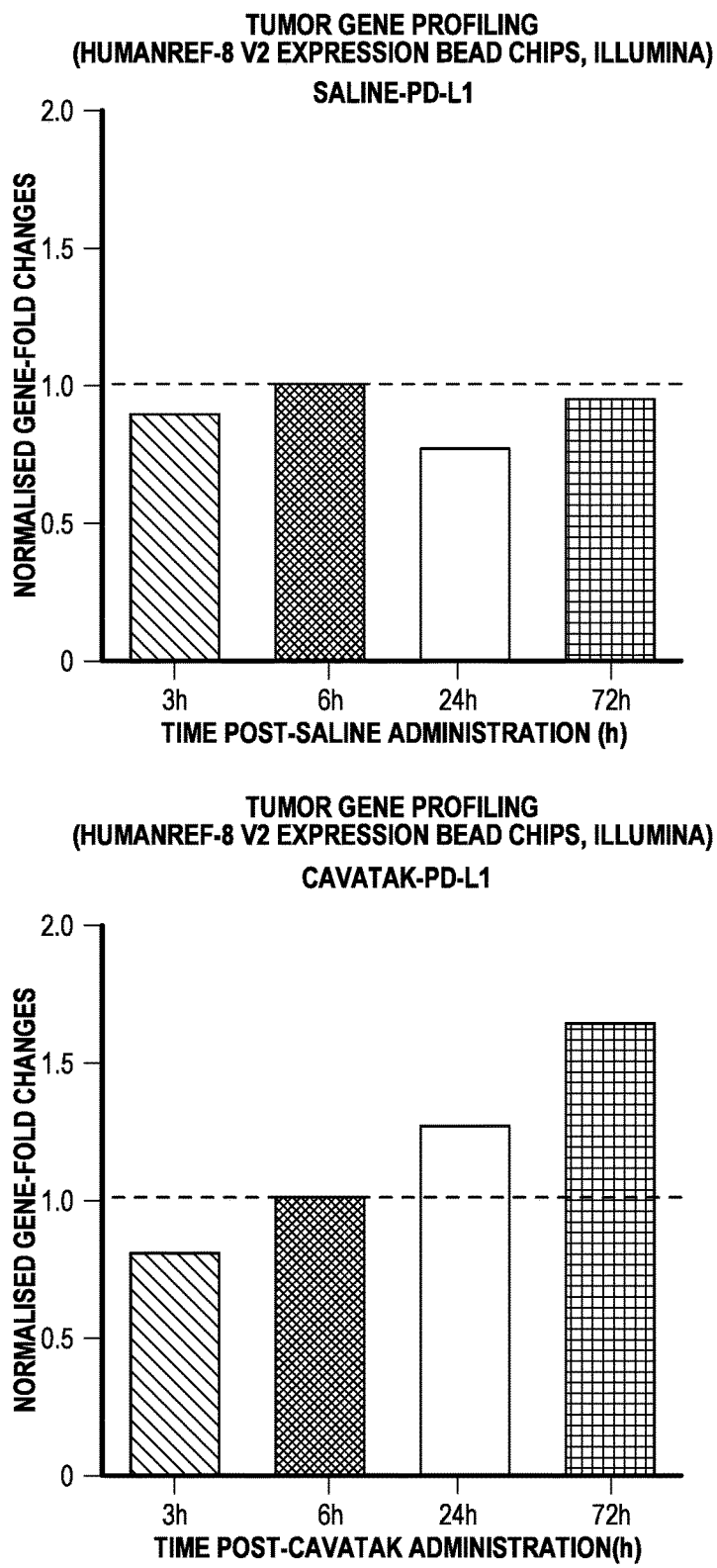

The observation herein of antitumour activity in non-injected lesions in particular is consistent with a systemic host immune-mediated anti-tumour response. The Examples herein suggest that the CVA21 mediated non-injected distant metatastic lesion activity was linked to a host generated immune response as evidence by a possible novel serum cytokine signature of elevated levels of serum IL-8 and g-IFN (FIG. 18). Intravenous delivery of CVA21 in a mouse model, implanted in the flank with melanoma cells (SK-Mel 28), was associated with an increase in the expression of interferon-γ inducible protein 10 (IP-10) and PD-L1 by the tumor cells, as assessed by a timecourse of tumor biopsy following administration of the virus (FIG. 19). IP-10 is a chemokine secreted by cells exposed to IFN-g and plays an important role in recruiting activated T cells into sites of tissue inflammation. In on-going clinical studies it is becoming increasingly apparent that patients whose tumours express higher levels of immune checkpoint molecules, such as PD-L1 display superior tumour responses compared to patients whose tumour lack PD-L1 expression following treatment using anti-PD-1 or anti-PD-L1 bloackade. This demonstrates the potential for CVA21 to act as a tumor immuno-agitator in combination with immune checkpoint inhibitor antibodies in ICAM-1 expressing cancers, such as melanoma, NSCLC, metastatic bladder cancer, kidney, multiple myeloma, pancreatic, glioblastoma and prostate cancers, and others.

The methods of the invention typically involve administration of a therapeutically effective amount of the virus and of the immuno-stimulatory agent. The term "therapeutically effective amount" as used herein, includes within its meaning a non-toxic but sufficient amount of the virus or immuno-stimulatory agent, to provide the desired therapeutic effect. As noted herein, due to synergistic effects the amount of virus and immuno-stimulatory agent, used may be less than that which would be used in a monotherapy (being treatment of a cancer in a subject using just one of the virus or the immuno-stimulatory agent). The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount" in the abstract. However, for any given case, an appropriate "effective amount" may be determined by one of ordinary skill in the art using only routine experimentation.

The oncolytic virus or oncolytic viral RNA and the immuno-stimulatory agent are used in conjunction with each other for, in one aspect, the treatment of a subject having a tumour or having cancer. In embodiments where the method involves "co-administration" of the viral and the immuno-stimulatory agents to a subject, it will be understood that this term means that the agents are administered so as to have overlapping therapeutic activities, and not necessarily that the agents are administered simultaneously to the subject. The agents may or may not be in physical combination prior to administration. Typically, the agents will not be in physical combination prior to or when administered. In an embodiment the virus and the immuno-stimulatory agent(s) are administered to a subject simultaneously or at about the same time. In an embodiment the virus is administered to the subject before the immuno-stimulatory agent(s) is administered.

The virus is typically administered to the subject in the form of a pharmaceutical composition comprising virus and a pharmaceutically acceptable carrier. The composition may comprise the virus at any suitable concentration, such as in a concentration range of about $10^5$ viral particles per ml to about $10^{15}$ viral particles per ml, or about $10^6$ viral particles per ml, or about $10^7$ viral particles per ml or about $10^8$ viral particles per ml, or about $10^9$ viral particles per ml, or about $10^{10}$ viral particles per ml, or about $10^{11}$ viral particles per ml, or about $10^{12}$ viral particles per ml, about $10^{13}$ viral particles per ml, or about $10^{14}$ viral particles per ml, or about $10^{15}$ viral particles per ml.

A stock of the virus composition may be diluted to an appropriate volume suitable for dosing, for example to achieve the desired dose of viral particles administered in a desired volume. For example, a subject may be administered a dose of virus comprising about $10^5$ viral particles to about $10^{15}$ viral particles, or about $10^6$ viral particles, or about $10^7$ viral particles, or about $10^8$ viral particles, or about $10^9$ viral particles, or about $10^{10}$ viral particles, or about $10^{11}$ viral particles, or about $10^{12}$ viral particles, or about $10^{13}$ viral particles, or about $10^{14}$ viral particles, or about $10^{15}$ viral particles. The volume in which the virus is administered will be influenced by the manner of administration. For example, administration of the virus by injection would typically be in a smaller volume, for example about 0.5 ml to about 10 ml, compared to administration by intravesicular instillation in the case of treatment of bladder cancer, which may typically use about 10 ml to about 100 ml, for example about 20 ml, about 30 ml, about 40 ml, about 50 ml, about 60 ml, about 70 ml, about 80 ml or about 90 ml, or in volumes similar to known procedures for instillation of BCG for treatment of bladder cancer. As a further example, intravenous administration of virus may typically use about 100 ml to about 500 ml of virus diluted in normal saline, infused by an automatic pump over approximately 30 minutes.

Compositions may additionally include a pharmaceutically acceptable diluent, excipient and/or adjuvant. The carriers, diluents, excipients and adjuvants must be "acceptable" in terms of being compatible with the other ingredients of the composition, and not unacceptably deleterious to the recipient subject.

The virus may be administered as naked viral RNA encoding the virus, rather than viral particles, as described for example in PCT/AU2006/000051 entitled "Methods and composition for the treatment of neoplasms", filed 17 Jan. 2006, published as WO2006/074526, the entire contents of which are incorporated herein by reference). In such an embodiment the viral RNA may be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

The virus may be administered to the subject by any appropriate means, such as by injection. The injection may be systemically, parenterally, direct injection into the cancer, or intravesically. Typically, in the treatment of bladder cancer the administration of the virus is intravesically (infused directly into the bladder).

Intralesional injection of a tumor may be performed by any appropriate means known to the skilled person, taking into account factors such as the type of tumour being treated, the size and location of the tumor, accessibility of the tumour to direct injection. Injection techniques which increase or maximise the distribution of the virus throughout the tumor may offer improved therapeutic outcomes. For example, in the treatment of melanoma and other solid tumors, multiple lesions may be injected in a dose hyper-fraction pattern, starting with the largest lesion(s) (2.0 mL injected into tumors>2.5 cm, 1.0 mL into 1.5 to 2.5 cm; 0.5 mL into 0.5 to 1.5 cm) to a 4.0 mL maximum. Following initial injection with CVA21, any injected lesion that reduces in diameter to <0.5 cm may be injected with 0.1 mL of CVA21 as per the stated treatment schedule until the lesion completely resolves.

Maximizing the number of cancer cells and regions throughout the tumor that are initially infected theoretically will increase the amount of cancer cells destroyed. It will also increase the amount of viral progeny produced by the tumor, and therefore increase the chance of ongoing viremia for the seeding of remote tumors. Any appropriate means to achieve desired distribution of the administered virus through the tumour may be used and will be apparent to the skilled addressee. The following describes one illustrative means, in the context of administration of CVA21 to a tumour, that the inventors have used in experiments reported herein.

A syringe that will accommodate the volume of virus, such as CVA21, required and a 25-gauge needle are used for administration. The volume of CVA21 to be administered may be determined based on the diameter of the tumor to be injected, as noted above. To load the syringe with CVA21, remove vial from individual carton and thaw at room temperature (18-25° C.). Do not leave the vial at RT for longer than is necessary to thaw the contents. Gently mix the vial for 5 seconds. Use a luer-lock syringe of appropriate volume and 21-gauge needle to draw up the required volume. Remove air bubbles. Remove the withdrawal needle and replace with a 25-gauge capped needle. Hold on ice until required (2-8° C.). Administer within 3 hours from loading the syringe as distributed into the tumors as described below.

The injection may be in 9 regions within the tumor on each injection day. The regions do not overlap, and they may be selected by using the following landmarks. The distribution of the viral solution may be as follows for Day 1, the first injection: (i) the center of the tumor is estimated and marked; (ii) marks are made around the periphery of the tumor at 45 degree radiants; (iii) the site of the needle insertion is between the center mark and the 270 degree radiant, at the approximate midpoint—this is the first dose injection site; (iv) the volume of distribution is divided by 10, and will be distributed into 9 zones within the tumor. The target zone for injection is the area within the tumor adjacent to the radiant marks, estimated to be approximately within the outer 20% "rim" of the tumor. This will result in 8 injections. These first 8 injections should be aimed to be deep to the midline plane of the tumor as guided by ultrasound. The final injection is made directly deep to the predicted center of the tumor, and on this first dose is aimed at a depth above the midline and comprises 20% of the injection volume.

It will be understood that the aforementioned calculation of amount of virus to be administered, as well as the described methods by which the virus may be administered are provided only for the purpose of illustration and are not intended to be limiting on the invention described herein.

The present invention provides methods for the treatment of cancer, the methods comprising the use of a human enterovirus C, such as CVA21, in combination with an immuno-stimulatory agent. The immuno-stimulatory agents that have been the subject of much recent research and clinical development are those that target the so-called checkpoint inhibitors. In checkpoint blockade humanised monoclonal antibodies are used to interfere with host immune checkpoint molecules and their natural ligands. Blockade of such molecules including PD-1, PDL1/L2 and CTLA-4 has resulted in dramatic anti-tumor responses in large numbers of advanced cancer patients (melanoma, non-small cell lung cancer, bladder and renal cancers). Immune checkpoint molecules normally function to keep the host immune system in balance and in maintaining self-tolerance. Specific blockade immune checkpoint molecules relaxes the negative feedback system and elevates the activity of the host immune system to be more active, in particular to cancerous cells and antigens. In simple terms it takes the "biological handbrake" of the host immune system Immune checkpoint blockade has resulted in improved durable tumor responses which have translated into meaning survival benefits. Despite the dramatic widespread tumor responses in large numbers of cancer patients there remains a need to increase the rate and durabililty of tumor responses elicited by immune checkpoint blockade.

As demonstrated herein, the combination of an oncolytic human enterovirus C, such as CVA21, with an immune checkpoint blockade molecule (an immuno-stimulatory agent), such as an anti-PD-1 antibody or an anti-CTLA-4 antibody, provides surprising advantages in eliciting favourable tumour response. Importantly, it has surprisingly been identified that administration of the virus induces changes to the stasis of the tumor microenvironment, with regard to impact on expression levels of immune checkpoint molecules and host immune cell infiltrates. As a number of these immune up-regulation processes involve the direct activity of immune stimulating agents such as interferons, in particular interferon-γ, therapeutic approaches involving administration of human enterovirus C, such as CVA21, to induce intracellular viral replication is an attractive process to initiate a targeted disruption of the delicate balance of host immune system activities.

The immuno-stimulatory agent(s) may be selected from any appropriate agents. In the context of the invention an immuno-stimulatory agent will be understood as any agent capable of stimulating an immune response to tumor cells when administered to an individual. In preferred embodiments of the invention the immuno-stimulatory agent may be any agent that interacts with an immune checkpoint molecule to block, diminish or counteract the ability of that immune checkpoint molecule, or a complex comprising that immune checkpoint molecule, in reducing the innate immune-based anti-tumor responses of the individual. Hence, an immuno-stimulatory agent reduces the "handbrake" effect that the immune checkpoint molecules have on the anti-tumor response. For example, the immuno-stimulatory agent may be any agent that targets an immune checkpoint molecule selected from the group consisting of PD-1, PD-L1, PD-L2, CTLA-4, CD134, CD134L, CD137, CD137L, CD80, CD86, B7-H3, B7-H4, B7RP1, ICOS, TIM3, GAL9, CD28 or OX-40. It will also be understood that the term "immuno-stimulatory agent" as used herein may also be referred to as immune checkpoint inhibitors, when the immuno-stimulatory agent targets an immune checkpoint.

Typically, the immuno-stimulatory agent may be an antibody, or in preferred embodiments may be a monoclonal antibody. Preparation of antibodies for use in the present invention may be carried out by methods well known in the art, including preparing monoclonal antibodies using well known techniques and screening for high affinity antibodies, or by first identifying a monoclonal antibody having reasonably high affinity and then improving the affinity using well known methods [e.g., Huse, W. D., et al., Internat'l Rev. Immunol. 10: 129-137 (1993); Yelton, D. E., et al., J. Immunol. 155: 1994-2004 (1995); Wu, H., et al., Proc. Natl. Acad. Sci. (USA) 95: 6037-6042 (1998); Crameri, A., et al., Nature Medicine 2: 100-103 (1996); Stemmer, Proc. Natl. Acad. Sci. (USA) 91: 10747-10751 (1994); Stemmer, Nature 370: 389-391 (1994), the portion of each of which having to do with preparation of antibodies is incorporated herein by reference]. Alternatively, the agent may be obtained rather than prepared. Examples antibodies to checkpoint inhibitor molecules include Nivolumab (BMS-936558, MDX-1106, ONO-4538), a fully human Immuno-globulin G4 (IgG4) monoclonal PD-1 antibody which was the first of its class to be tested in a phase I trial of 107 patients with metastatic melanoma [Sosman et al. 2012b]. Lambrolizumab (MK-3475), a humanized monoclonal IgG4 PD-1 antibody, which was studied in a phase I trial that included 132 patients with metastatic melanoma [Iannone et al. 2012]. BMS-936559, a fully human IgG4 PD-L1 antibody, was tested in 55 patients with metastatic melanoma as part of the phase I trial [Brahmer et al. 2012].

In the treatment of a patient for a particular type of cancer the skilled addressee will be aware that additional methods or steps of treatment may also be appropriate. For example, in the treatment of a patient for bladder cancer, the methods of the invention may optionally include a bladder rinse or washout prior to administration of the virus, for example to prepare the bladder for improved receptivity of the virus by removing or reducing the presence of agents which may reduce the efficacy of the virus. For example, the urothelium is protected by a glycosaminoglycan (GAG) layer, disruption of which may permit more efficient binding of the virus to cells and hence more efficient transduction of cells. In a non-limiting example DDM (n-dodecyl-β-D-maltoside), a nonionic mild detergent used as a food additive and solubilizing agent, may be used to disrupt or remove the GAG layer at any appropriate concentration, for example at a concentration of about 0.1%, and thereby assist in facilitating transduction.

The methods of the invention may be used in combination with surgical treatment of the cancer. For example tumor resection may be followed by treatment of the subject using a combination method according to the invention. It is anticipated that this may prevent or reduce recurrence of the tumour.

The methods may comprise single or multiple doses of any one or more of the virus, or the immuno-stimulatory agent, such as an agent for example a monoclonal antibody, that specifically binds to the surface expressed PD-1, PD-L1, PD-L2, CTLA-4 or OX-40.

The invention also relates to kits for use in the methods of the invention. In a basic form, the kit may comprise a pharmaceutical composition comprising the human enterovirus C and a pharmaceutically acceptable carrier, and instructions for the use of the composition, in combination with a chemotherapeutic agent or radiation, for the treatment of cancer in a patient. The composition may be provided in any suitable container, such as for example a vial, ampoule or syringe. The composition may be provided lyophilised, freeze-dried, in liquid form or frozen state.

The kit may comprise any number of additional components. By way of non-limiting example, additional components may include (i) one or more anti-viral agents, such as Plecornil; (ii) one or more additional pharmaceutical compositions comprising an oncolytic virus; (iii) one or more additional pharmaceutical compositions comprising oncolytic viral RNA; (iv) one or more additional therapeutic agents useful in the treatment of cancer in a patient. The kit may additionally comprise a an immuno-stimulatory agent for use in the combination therapy, such as a monoclonal antibody that specifically binds to the surface expressed PD-1, PD-L1, PD-L2, CTLA-4 or OX-40. The kit may also comprise of the composition being contained in a single-use vial, a pre-loaded syringe for direct human administration, diluted in a physiological solution for intravenous infusion or in a concentrated form enabling suitable dilution with physiological solutions. Such solutions may be, for example, phosphate buffered saline or physiological concentrations of $NaCl_2$.

As used herein, the term "kit" refers to any delivery system for delivering materials. In the context of pharmaceutical compositions, such delivery systems include systems that allow for the storage, transport, or delivery of therapeutic agents (for example, oncolytic viruses in appropriate containers; or immuno-stimulatory agents in appropriate containers) and/or supporting materials (for example, buffers, written instructions for use of the compositions, etc.) from one location to another. For example, kits include one or more enclosures, such as boxes, containing the relevant components and/or supporting materials.

The kit may be a fragmented kit. As used herein, the term "fragmented kit" refers to a delivery system comprising two or more separate containers that each contain a subportion of the total kit components. The containers may be delivered to the intended recipient together or separately. A fragmented kit may be suitable, for example, where one or more components, such as the virus or the immuno-stimulatory agent, may optimally be stored and or transported under different conditions, such as at a different temperature, compared to one or more other components. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

EXAMPLES

Example 1: Oncolytic CVA21 Virotherapy in Combination with the Immunostimulatory Antibody Anti-PD-1

This study investigated the effectiveness of CVA21 oncolytic virotherapy in combination with the immunostimulatory antibody anti-PD-1 in a B16-ICAM-1 murine model of malignant melanoma. Mice were implanted with tumours intradermally ($2 \times 10^5$ cells) and allowed to establish for 12 days before commencement of therapy. Mice were treated with either saline, CVA21 or UV-inactivated CVA21, in combination with either a murine anti-PD-1 antibody or a matched control antibody on days 12, 15, 18 and 21. The saline, CVA21 or UV-inactivated CVA21 treatments were administered intratumourally while the anti-PD-1 and control antibodies were administered intraperitoneally. Animals treated with CVA21 in combination with the anti-PD-1 antibody showed a slight survival benefit compared to animals in the control group (saline+control antibody) based on the endpoint of tumour ulceration or a loss in bodyweight greater than 10%. During the treatment period between days 12 and 21, the combination of CVA21+anti-PD-1 showed a tumoristatic effect, however once therapy was stopped, the tumours slowly increased in volume. Despite this, the animals in this group showed a statistically significant survival advantage compared to the saline+control antibody, UV-CVA21+control antibody and UV-CVA21+anti-PD-1 antibody treatment groups. This study also confirmed the immunostimulatory properties of the anti-PD-1 antibody, as anti-CVA21 neutralising antibody levels were detected at higher levels in mice receiving CVA21+anti-PD-1 vs CVA21+control antibody. In summary the main finding of this study was that tumour bearing mice treated CVA21+ anti-PD-1 showed an overall survival benefit that related to retardation of tumour growth and reduction in tumour ulceration.

Test Material: Virus

The test article, Coxsackievirus A21 (CVA21) [Trade name:CAVATAK™] was provided by Viralytics Ltd. Research stocks for in vitro use were made from a vial of commercially prepared CAVATAK™. Batch: CCVA2115; Concentration: $1 \times 10^9$ TCID$_{50}$/ml (1.1 ml vials); Re-test Date: December-2008, January 2014 for Examples 2 and 3; Storage Recommendations: Store below $-70°$ C.

The UV-inactivated CVA21 was prepared by exposing 7 ml of the same CAVATAK™ Batch:CVA2115 product to UV-light for one hour in a biohazard hood. The virus was first transferred from the original product vials to wells of a 6-well plate and exposed to the UV-light source at a distance of approximately 10 cm for one hour. The UV-inactivated virus was then aliquoted and frozen at $-80°$ C.

Antibodies

Control Antibodies

The antibody InVivoMAb Rat IgG2a from BioXCell was used as a control antibody in Examples 1 and 2. Clone: 2A3. Catalog #: BE0089. Lot: 4807/0713. Endotoxin: <0.35 EU/mg. Formulation: PBS, pH 6.5. Sterile: 0.2 um filtration. Purity: >95%. Storage: $4°$ C. undiluted in the dark. The antibody InVivoMAb Rat IgG2b from BioXCell was used as a control antibody in Example 3. Clone MPC-11. Catalog #BE0086. Lot 4700-2/0414. Endotoxin: <2.0 EU/mg. Formulation: PBS, pH 7. Sterile: 0.2 um filtration. Purity: >95%. Storage: $4°$ C. undiluted in the dark.

Anti-PD-1

The active anti-murine PD-1 antibody was obtained from BioXCell. Product name: InVivoMAb anti m PD-1. Clone: RMP1-14. Catalog #: BE0416. Lot: 4781/0813. Endotoxin: <0.61 EU/mg. Formulation: PBS, pH 7. Sterile: 0.2 um filtration. Purity: >95%. Storage: $4°$ C. undiluted in the dark.

Anti-CTLA-4

The active anti-murine CTLA-4 antibody was obtained from BioXCell. Product name: InVivoMAb anti m CTLA-4. Clone: 9D9. Catalog #: BE0164. Lot: 5159/0414. Endotoxin: <2.0 EU/mg. Formulation: PBS, pH 7. Sterile: 0.2 um filtration. Purity: >95%. Storage: $4°$ C. undiluted in the dark.

Cells

The human melanoma cell line SK-Mel-28 and murine melanoma cell lines B16 and B16-ICAM-1 were used in this study. The melanoma cell line SK-Mel-28 was obtained from the ATCC (American Type Culture Collection). Mel-RM was a gift by Dr. P. Hersey (University of Newcastle, New South Wales, Australia). B16 murine melanoma cells were originally obtained from Dr A. Shurbier (Queensland Institute for Medical Research, Brisbane, Queensland, Australia), and then stably transfected with the human ICAM-1 gene to generate the cell line B16-ICAM-1. All cell lines were maintained in DMEM (Thermo Scientific), containing 10% fetal calf serum (FCS) (SAFC Biosciences™, Australia), 10 mM sterile N-2-hydroxyethylpiperazine N'-2-ethanesulphonic acid (HEPES) (ThermoScientific, Australia), 2 mM L-glutamine (ThermoScientific, Australia), sodium pyruvate (Invitrogen, Australia) and 100 IU/ml penicillin-streptomycin (Invitrogen, Auckland, NZ). All cells were cultured at 37 in a 5% $CO_2$ environment.

Animals

All animal work was approved by The University of Newcastle Animal Care and Ethics Committee (ACEC) under approval number: A-2013-327. Six to eight week-old female C57BL/6 mice (n=52) were obtained through the Animal Services Unit of The University of Newcastle. They were maintained in a specific pathogen-free area in the animal resources facility within individually ventilated cages. Mice were housed in groups of 4 within HEPA-filtered Techni-Plast Cages (1145 IVC) connected to a Techni-Plast Slim Line air handling system within a PC2 laboratory with a 12/12 hour light/dark cycle. Mice were fed ad libitum with mouse cubes/pellets manufactured by Specialty Feeds, WA, Australia. This standard mouse feed was formulated to be low in fat content (approximately 5%) and is meat free. The airflow in the room was 12 to 15 air changes per hour but the airflow in the IVC cages was at a rate of 70 changes per hour. The mice were identified by tail markings with a permanent pen. All animal studies were conducted according to protocols approved by the Animal Ethics Committee. At the conclusion of the study or when animals reached a humane endpoint mice were euthanased by $CO_2$ asphyxiation.

Methods

Virus $TCID_{50}$ Assay

Confluent monolayers of SK-Mel-28 cells in 96-well tissue culture plates were inoculated with 10-fold serial dilutions (100 μL/well in quadruplicate) of CVA21 and incubated at 37° C. in a 5% $CO_2$ environment for 72 h. The mouse serum was serially diluted 10-fold ranging from $1:10^2$ to $1:10^8$ in DMEM containing 2% fetal calf serum (FCS). Wells were scored for cytopathic effects (CPE) visually under an inverted microscope. Wells that had detectable CPE were scored positive and the 50% viral endpoint titre was calculated using the Karber method (Dougherty 1964).

Virus Neutralisation Assay

To test for the presence of neutralising antibodies, heat inactivated mouse serum samples were first diluted in DMEM (2% FCS) 1:32 to 1:2048. One hundred microlitres of each serum dilution was incubated with 100 μL of CVA21 (100 $TCID_{50}$) at 37° C. for 1 hr. Fifty microlitres of this serum/virus mixture was then plated in triplicate on SK-Mel-28 cells in a 384-well format. A +IgG (positive control) was obtained commercially through Commonwealth Serum Laboratories (Sandoglobulin NF Liquid, Batch number: 4322800002). Wells were scored for the presence of virus neutralisation (lack of CPE) visually under an inverted microscope. The neutralising antibody titre was then calculated using the Karber method (Dougherty1964).

Immune-Competent B16-ICAM-1 Mouse Model of Melanoma

Fifty two female C57BL/6 mice (Animal Services Unit, The University of Newcastle, Australia) aged between six to eight weeks were housed in the same conditions as described above. The hind flanks of mice were shaved using electric clippers three days prior to the injection of tumour cells to allow sufficient recovery time. B16-ICAM-1 cells were harvested with trypsin, washed twice and resuspended in sterile PBS. The viability of the prepared cells was assessed by trypan blue staining and analysis with a TC-10 Automated Cell Counter (Biorad, Hercules, Calif., USA), and only cell preparations with >95% viability were used for xenotransplantation. Prior to tumour transplantation, animals were anesthetized with 5% isoflurane. Tumours were inoculated intradermally with a single injection of $2 \times 10^5$ B16-ICAM-1 cells in a volume of 50 μL of PBS in the hind flank of mice.

The treatment groups and overview of the protocol used in Examples 1-3 is briefly as follows.

Figure 1B:
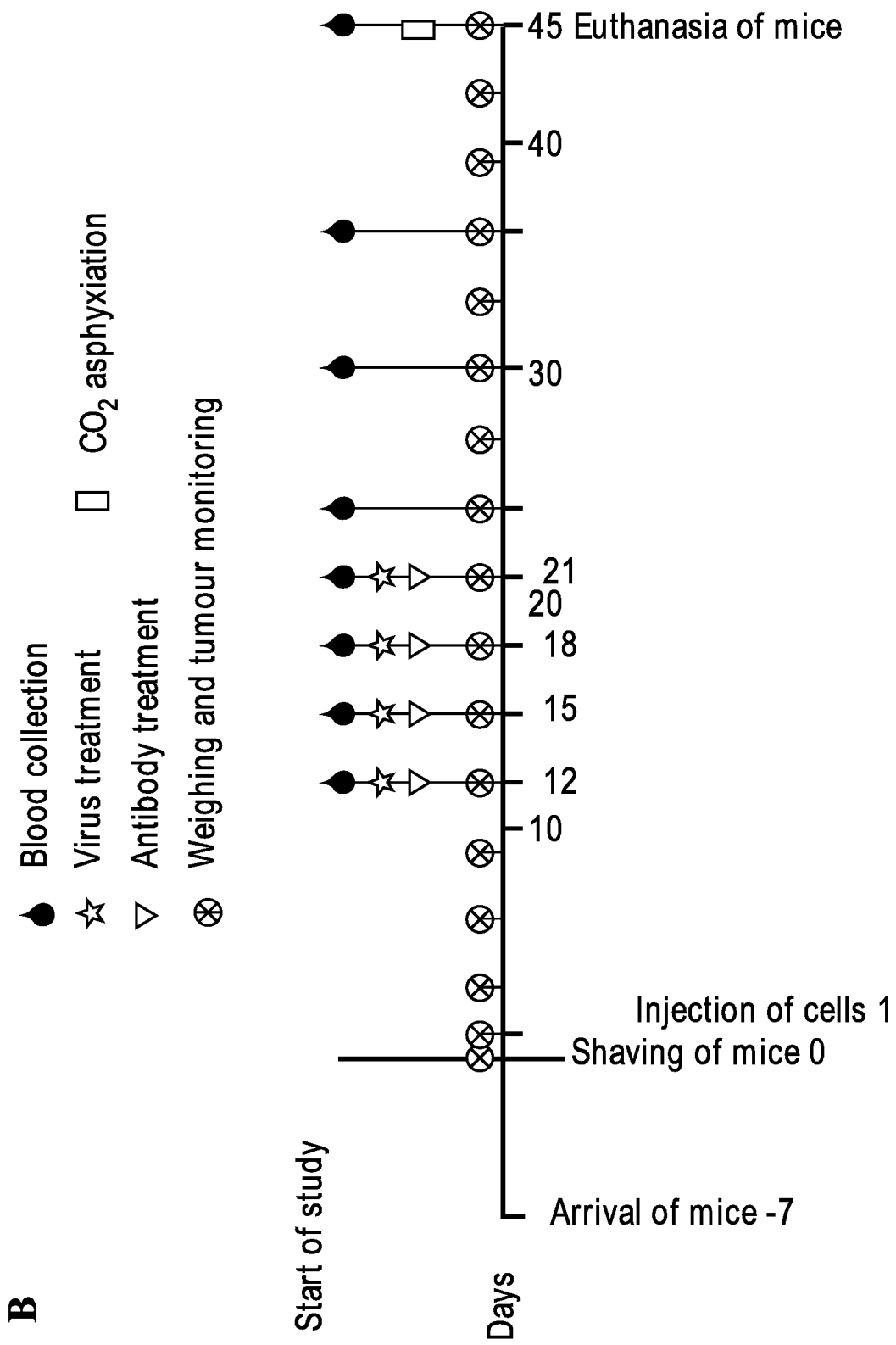
Figure 2:
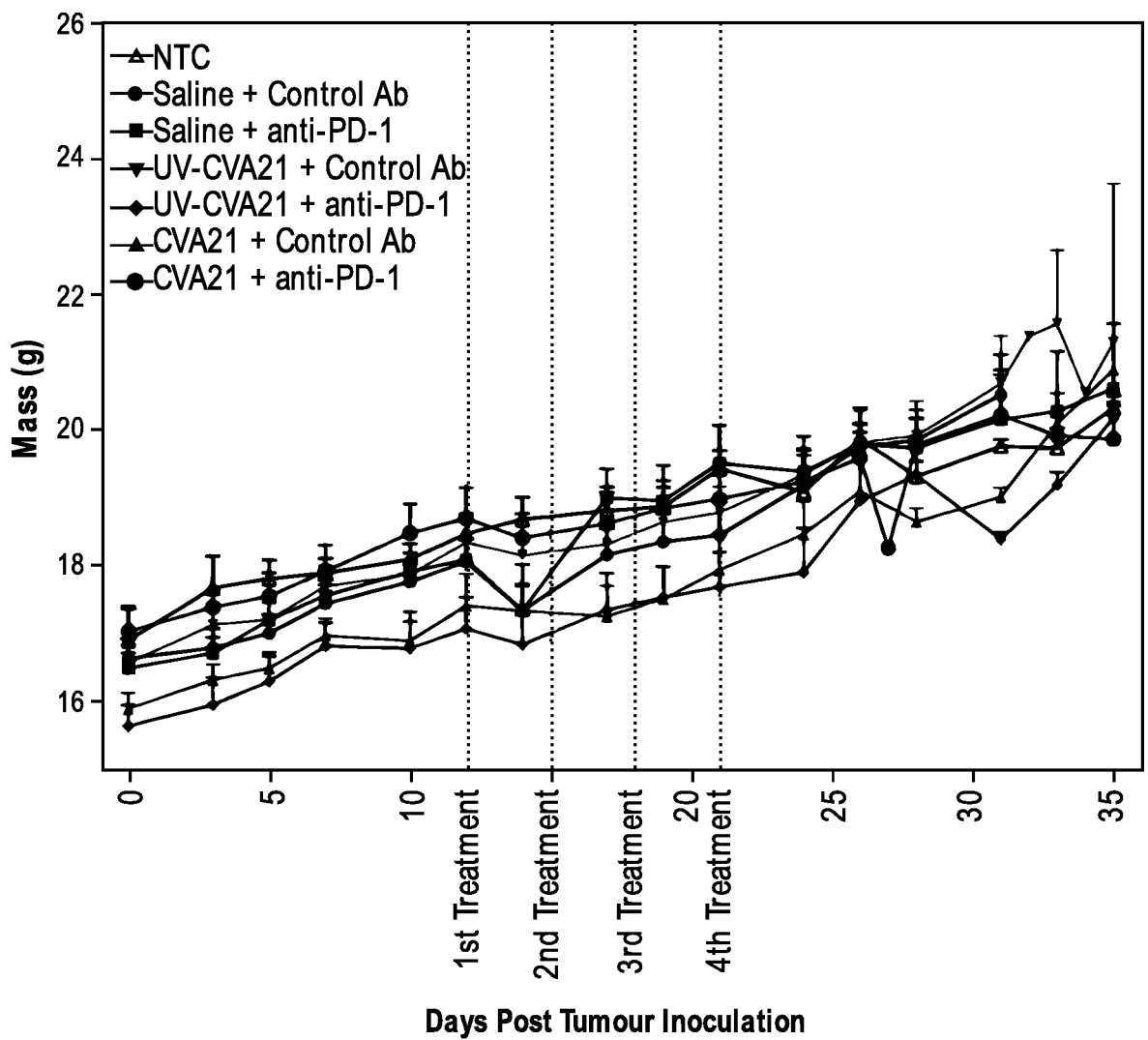
FIG. 2: Average body weights of mice (g) vs time (days). Error bars indicate standard error. The dotted lines at day 12, 15, 18 and 21 show each cycle of therapy. Using multiple t-tests corrected for multiple comparisons (Holm-Sidak method), there were no statistically significant differences between the average body weights of treatment groups and the no tumour control (NTC) mice, except for the UV-CVA21+anti-PD-1 group at day 31. Some fluctuations in mean weights were observed due to the euthanasia of mice over the duration of the study.
Figure 3A:
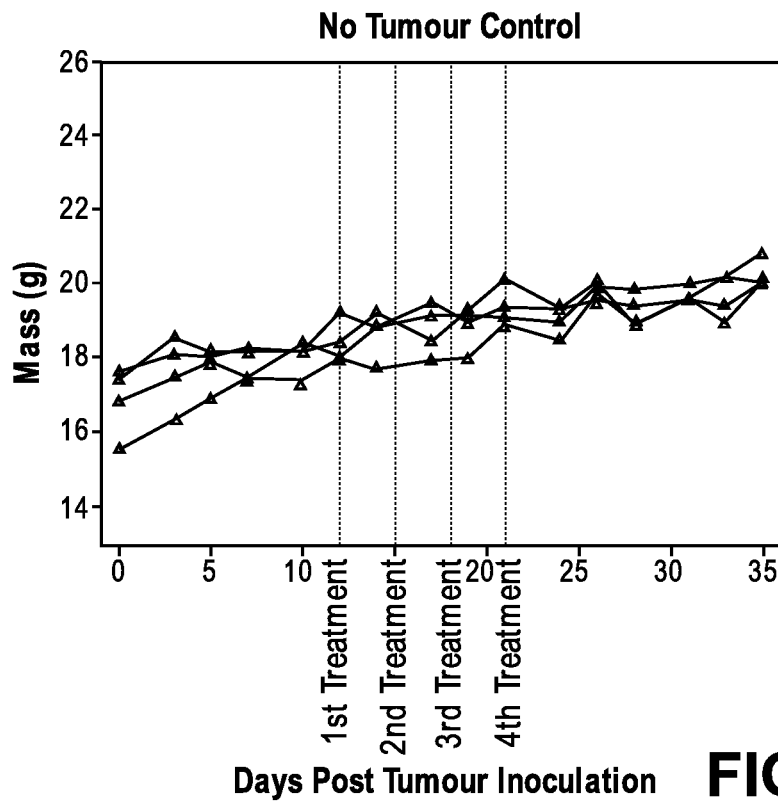
FIG. 3A-3G: Individual body weights of mice (g) vs time (days). The dotted lines indicate the four rounds of therapy at day 12, 15, 18 and 21. A) No Tumour control group, B) Saline+Control Ab, C) Saline+anti-PD-1, D) UV-CVA21+Control Ab, E) UV-CVA21+anti-PD-1, F) CVA21+Control Ab, G) CVA21+anti-PD-1.
Figure 3B:
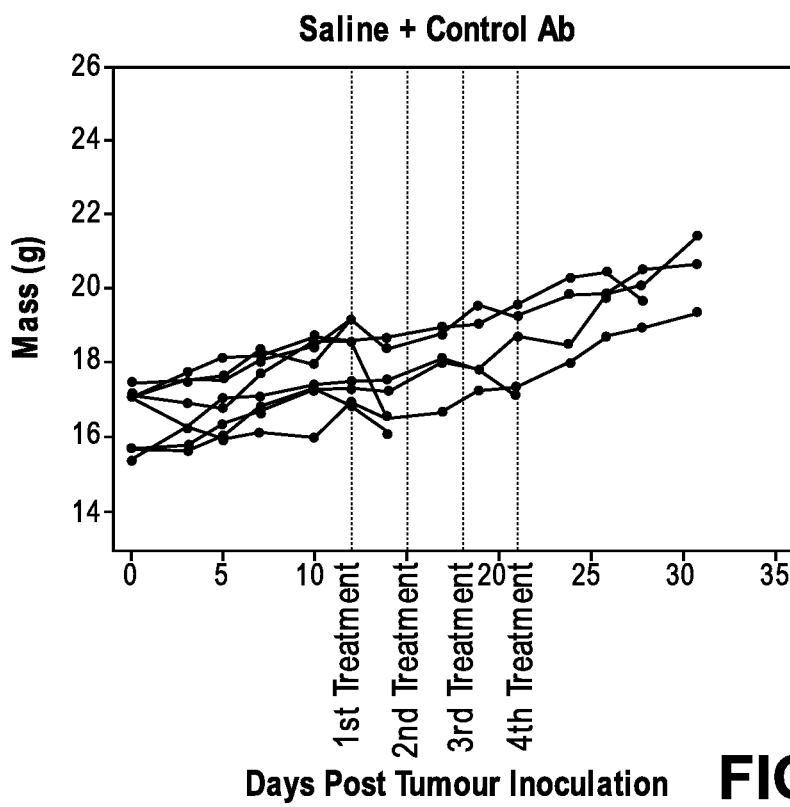
Figure 3C:
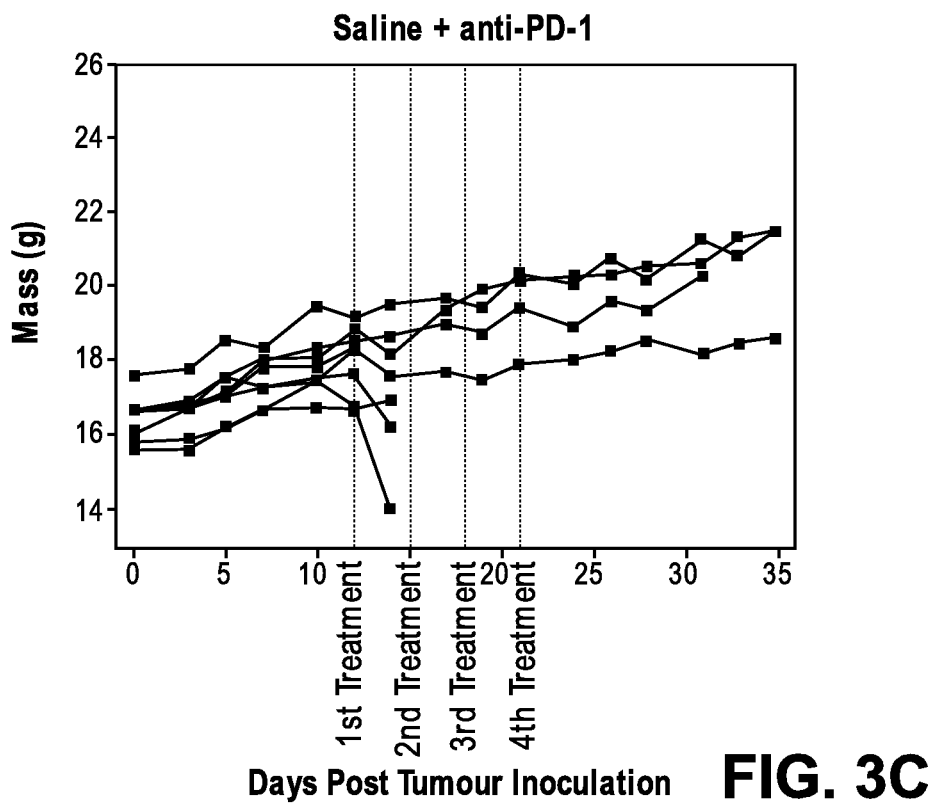
Figure 3D:
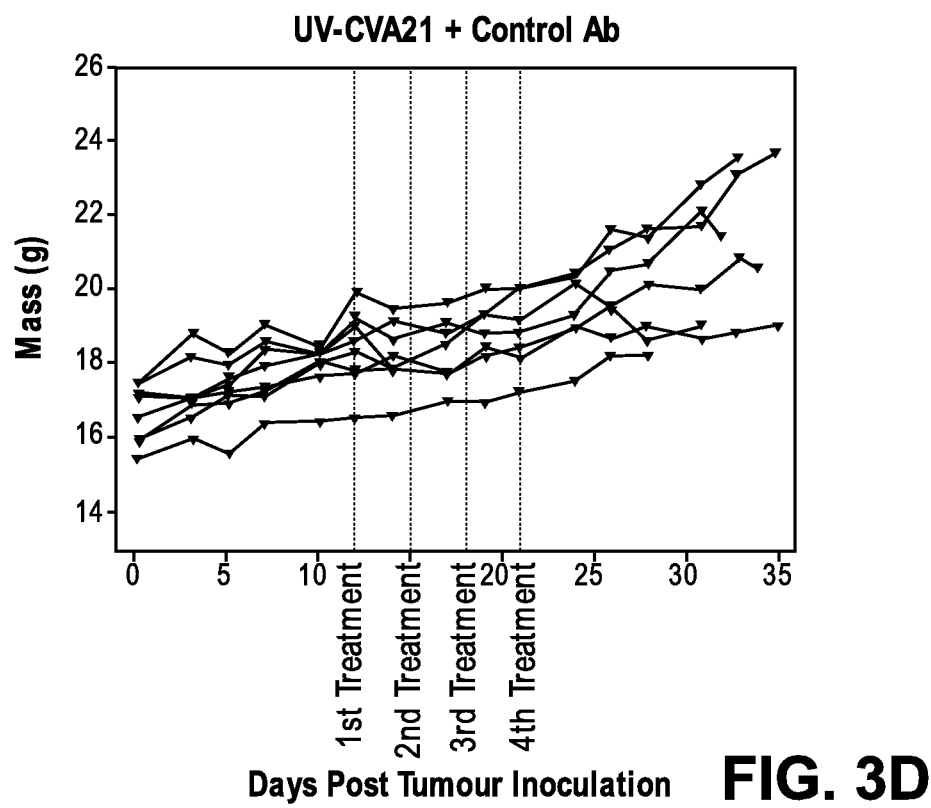
Figure 3E:
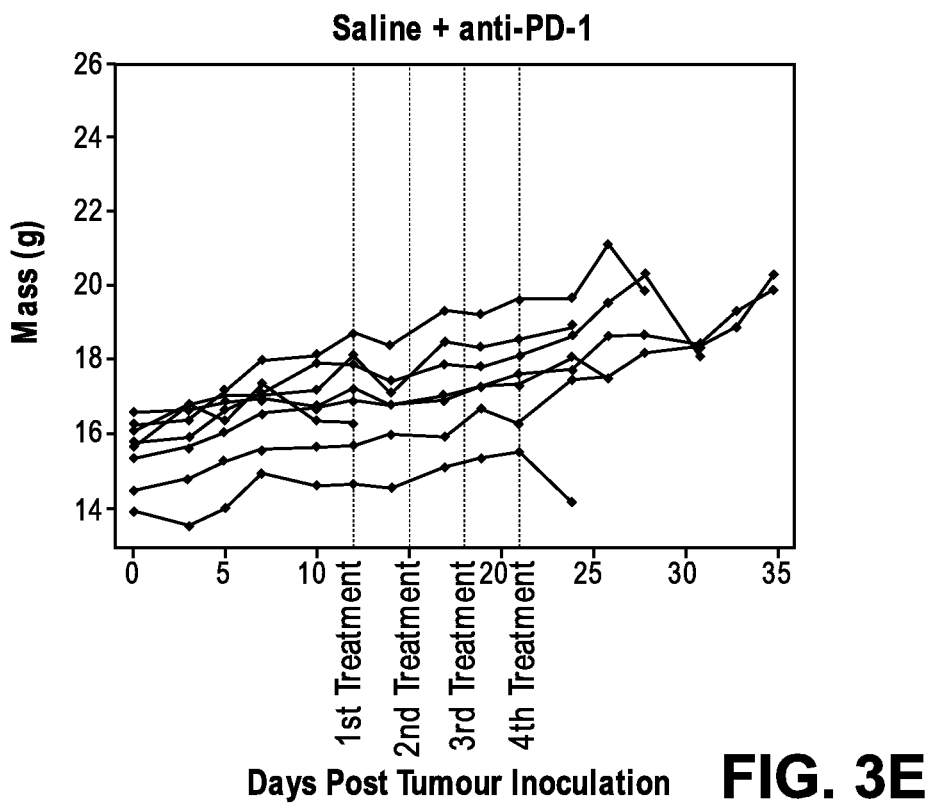
Figure 3F:
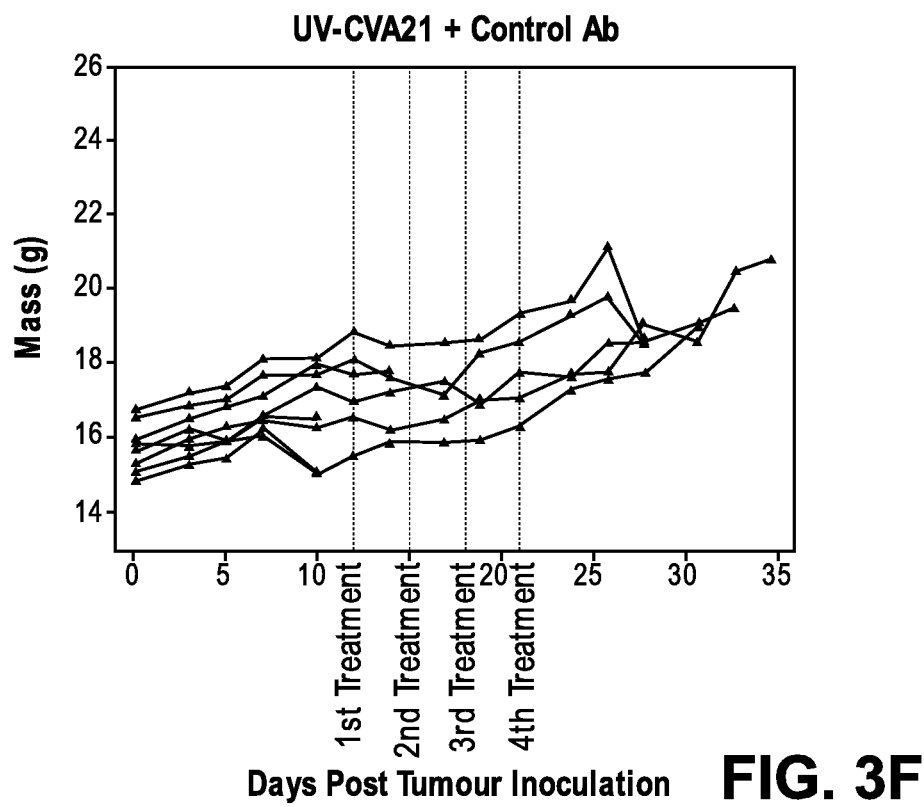
Figure 3G:
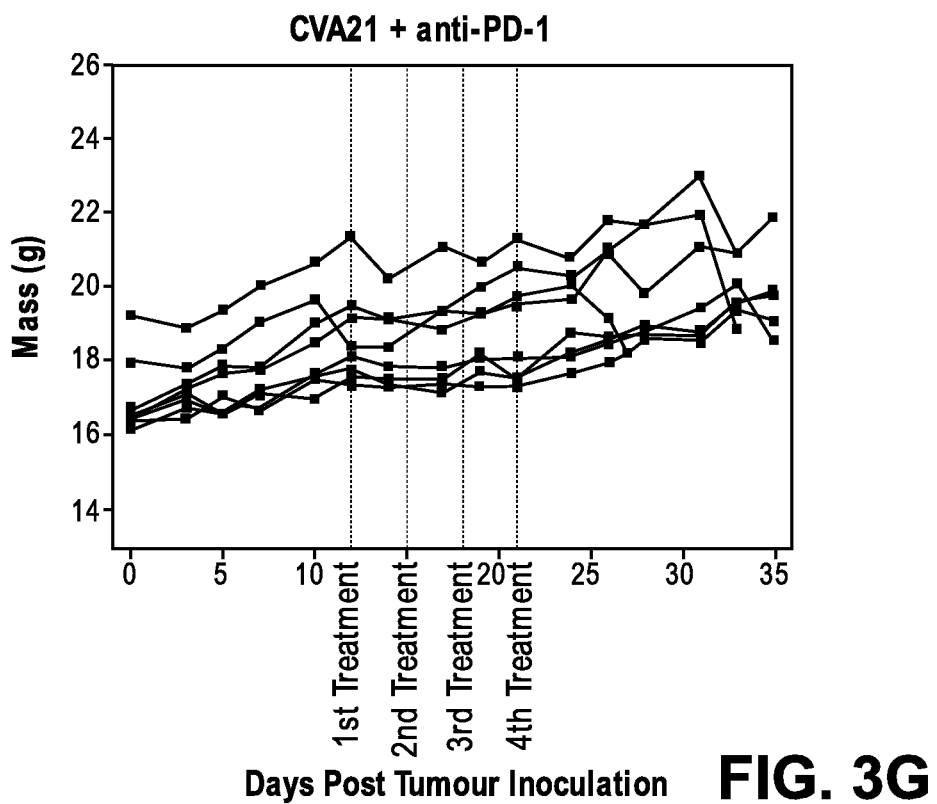

In Example 1, animals were treated with either saline, CVA21 ($1 \times 10^8$/injection) or UV-inactivated CVA21 ($1 \times 10^8$/injection), in combination with the control antibody or the anti-PD-1 antibody (12.5 mg/kg respectively). Treatment was initiated 12 days post tumour cell implantation with animals receiving the intratumoral treatment first (0.1 ml), followed by the intraperitoneal antibody (0.2 ml) immediately after. Mice were given four courses of therapy every 3 days, starting at day 12 and ending on day 21 post tumour inoculation. A summary of the treatment schedule used for Example 1 is shown in FIG. 1.

Figure 8:
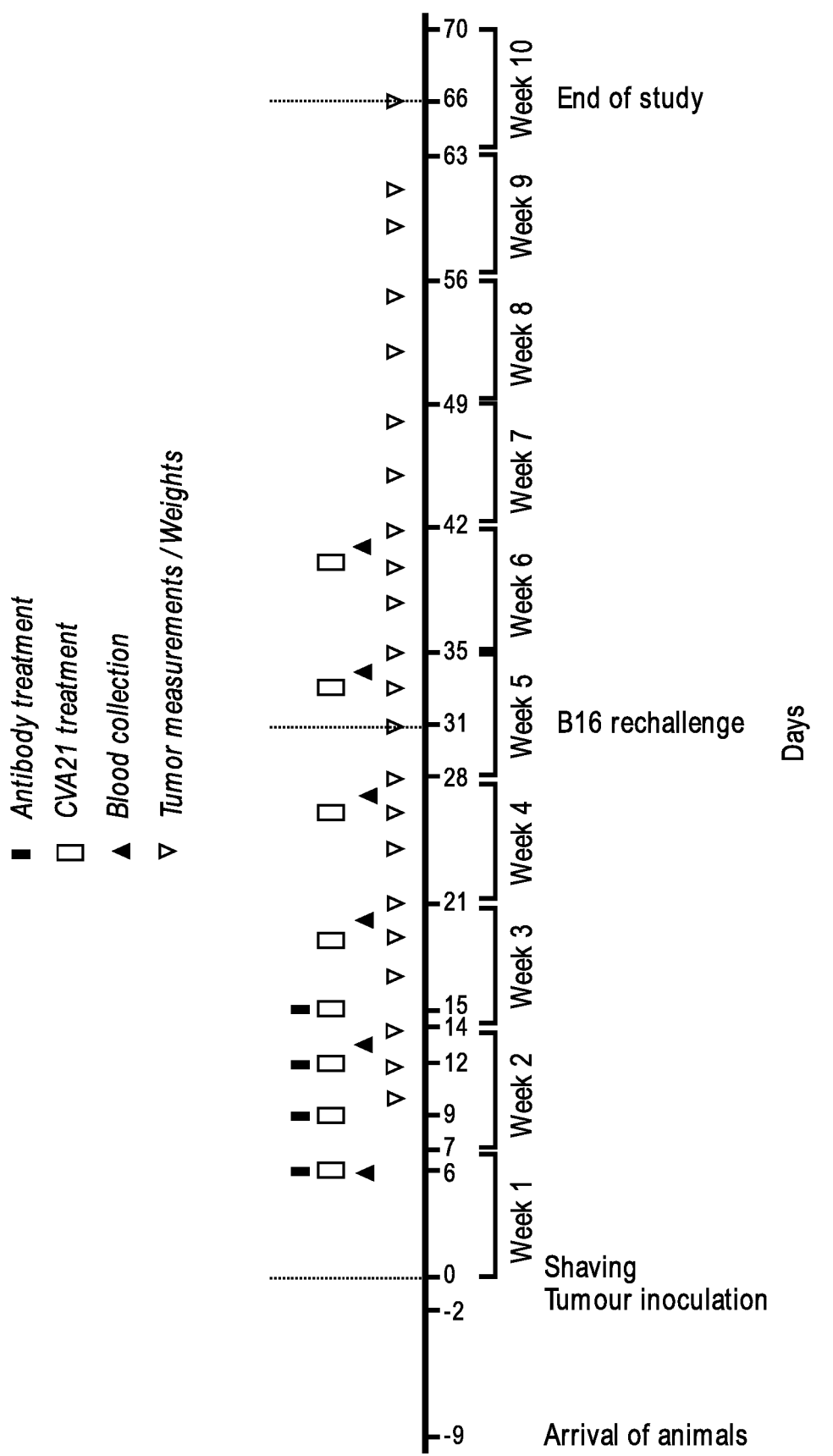
FIG. 8: Overview of immune-competent murine melanoma protocol, as described in Example 2. Time line showing the schedule of treatments (blue circles [anti-PD-1 antibody], orange squares [CVA21]) and monitoring procedures (red triangles [blood collection] and green triangles [tumor measurements and body weight measurements]). Animals were first treated with either saline or CVA21 ($1 \times 10^8$ $TCID_{50}$/injection [$5.56 \times 10^9$ $TCID_{50}$/kg]), followed by intraperitoneal injections with the murine isotype control antibody or the anti-PD-1 antibody (12.5 mg/kg). The experiment was terminated on day 66.

In Example 2 animals were treated with either saline or CVA21 ($1 \times 10^8$ $TCID_{50}$/injection), in combination with either the control antibody or the anti-PD-1 antibody (12.5 mg/kg respectively). Treatment was initiated 6 days post tumor cell implantation with animals receiving the intratumoral treatment first (0.1 ml/mouse), followed by the intraperitoneal antibody (0.2 ml/mouse) immediately after. Mice were given four courses of therapy every 3 days, starting at day 6 and ending on day 15 post tumor inoculation. Animals were given additional top-up injections of saline of CVA21 ($1 \times 10^8$ $TCID_{50}$/injection) at weekly intervals thereafter for a period of four weeks. A summary of the treatment schedule used for Example 2 is shown in FIG. 8.

Figure 12:
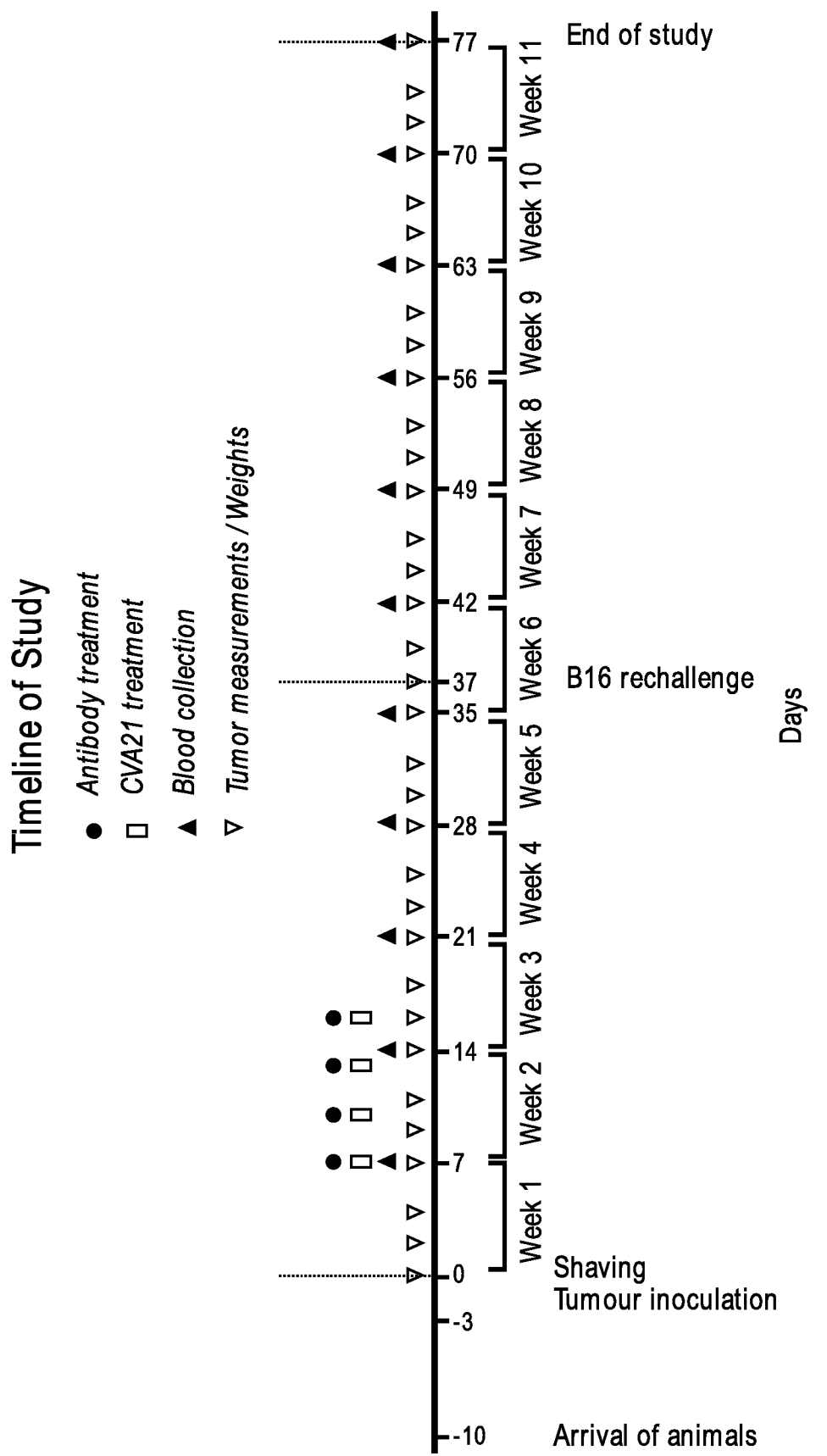
FIG. 12: Overview of immune-competent murine melanoma protocol. Time line showing the schedule of treatments (blue circles [anti-CTLA-4 antibody] and orange squares [CVA21]) and monitoring procedures (red triangles [blood collection] and green triangles [tumor measurements and body weight measurements]). The experiment was terminated on day 77.

In Example 3 animals were treated with either saline, CVA21 ($1 \times 10^8$ TCIDso/injection), in combination with the control antibody or the anti-CTLA-4 antibody (12.5 mg/kg respectively). Treatment was initiated 7 days post tumor cell implantation with animals receiving the intratumoral treatment first (0.1 ml), followed by the intraperitoneal antibody (0.2 ml) immediately after. Mice were given four treatments spaced 3 days apart, starting at day 10 and ending on day 16 post tumor inoculation. A summary of the treatment schedule used for Example 3 is shown in FIG. 12.

In Example 4 mice were treated with either intravenous saline or intravenous CVA21 ($1 \times 10^8$ $TCID_{50}$ [$5.56 \times 10^9$ $TCID_{50}$/kg assuming a 18 g mouse]), in combination with either a murine anti-PD-1 or anti-CTLA-4 or anti-PD-1+ anti-CTLA-4 antibodies or a matched control antibody as described above (12.5 mg/kg) on days 7, 10, 13 and 16. Saline or CVA21 treatments were administered intravenously while the anti-CTLA-4, the anti-PD-1 and control antibodies were administered intraperitoneally (n=12-14 per group). As will be understood by the skilled addressee intraperitoneal administration is an effective way of getting the antibody into the bloodstream and so provides an appropriate model for systemic administration.

Tumours were measured twice a week and tumour volumes were estimated based on the volume of a spheroid $V = \Pi/6 \cdot a \cdot b^2$ where "a" and "b" are the longest and shortest perpendicular diameters of the tumour respectively. Blood from all mice were collected on a weekly basis by venipuncture of the saphenous vein and centrifuged at 10,000 rpm for 5 min at room temperature to collect the serum. Serum samples were stored at −80° C. until further testing. The animals were humanely euthanased by $CO_2$ asphyxiation when tumours became ulcerated or loss in body weight exceeded 10%, otherwise mice were sacrificed at endpoint of study (day 45 in Example 1; day 66 in Example 2; day 77 in Example 3).

TABLE 1

Immune-competent C57BL/6 mouse model: Mouse identification numbers and allocation of treatment groups

| Group 1 NTC | Group 2 Saline + Control Ab | Group 3 Saline + anti-PD-1 | Group 4 UV CVA21 + Control Ab | Group 5 UV CVA21 + anti-PD-1 | Group 6 CVA21 + Control Ab | Group 7 CVA21 + anti-PD-1 |
|---|---|---|---|---|---|---|
| 1515 | 1519 | 1523 | 1551 | 1539 | 1531 | 1559 |
| 1516 | 1520 | 1524 | 1552 | 1540 | 1532 | 1560 |
| 1517 | 1521 | 1525 | 1553 | 1541 | 1533 | 1561 |
| 1518 | 1522 | 1526 | 1554 | 1542 | 1534 | 1562 |
| — | 1527 | 1535 | 1555 | 1547 | 1543 | 1563 |
| — | 1528 | 1536 | 1556 | 1548 | 1544 | 1564 |
| — | 1529 | 1537 | 1557 | 1549 | 1545 | 1565 |
| — | 1530 | 1538 | 1558 | 1550 | 1546 | 1566 |

Statistical Analysis

All data was analyzed and plotted using GraphPad Prism v6.0 (GraphPad Software Inc.). For analysis of animal data, GraphPad Prism v6.0 (GraphPad Software Inc.) was used to compare the difference in tumour volumes between treatment groups using the two-way ANOVA (with repeated measures) and Bonferroni post-tests. Comparison of survival curves was performed using the Log-rank (Mantel-Cox) test.

Results

In Vivo Assessment of Combination Oncolytic Virotherapy and Anti-PD-1 Immunotherapy in an Immune-Competent Mouse Model To assess whether the combination CVA21 and anti-PD-1 therapy approach was effective in an immune-competent mouse model of melanoma, C57BL/6 mice were implanted with murine B16-ICAM-1 tumour cells ($2 \times 10^5$) intradermally on the hind flank. Tumours were allowed to establish before commencement of therapy at 12, 15, 18 and 21 days post tumour inoculation (see FIG. 1). Saline or CVA21 was administered intratumourally at the indicated time points, while the control antibody or anti-PD-1 antibody were administered intraperitoneally. Mice were monitored daily and weighed up to three times a week and tumour volumes measured by electronic calipers twice a week. Blood sampling from the saphenous vein was carried out at weekly intervals. The study was terminated at day 45 post tumour inoculation.

Body Weights Following Treatment with Either Saline, CVA21 or UV-Inactivated CVA21 in Combination with Anti-PD-1 or Control Antibody.

Animals were weighed up to three times a week and results recorded electronically using FileMaker Pro and a proprietary animal monitoring database for record keeping (Internal Ref: Experiment #53). Raw weights can be found in Tables 2 to 10. Weights were also transcribed to the animal monitoring checklist/records to meet the requirements of our institutional Animal Care and Ethics Committee. No statistically significant differences in the mean body weight were observed between the treatment groups and NTC mice at any time points (multiple t-tests corrected for multiple comparisons using the Holm-Sidak method) except for the UV-CVA21+anti-PD-1 group at day 31 (Prism 6 for Mac OS X Version 6.0c, GraphPad Software, La Jolla Calif. USA, www.graphpad.com). Animals appeared to tolerate the CVA21 and anti-PD-1 therapy well and there were no observable toxicities from the treatments. A total of 9 animals were euthanased due to tumour ulceration and/or greater than 10% body weight loss. The decrease in weight was in the majority of cases linked to tumour ulceration and associated tumour burden.

TABLE 2

Immune-competent animal model: Individual mouse body weights of Group 1 - No Tumour Control (NTC) mice.

| | Group 1 - NTC - Mouse no. | | | |
|---|---|---|---|---|
| Study Day | 1515 | 1516 | 1517 | 1518 |
| −2 | 15.34 | 16.13 | 18.02 | 17.23 |
| 0 | 15.6 | 16.86 | 17.65 | 17.45 |
| 3 | 16.4 | 17.5 | 18.16 | 18.57 |
| 5 | 16.99 | 17.92 | 18.07 | 18.21 |
| 7 | 17.46 | 17.54 | 18.31 | 18.2 |
| 10 | 17.41 | 18.45 | 18.25 | 18.22 |
| 12 | 17.97 | 18.11 | 19.29 | 18.47 |
| 14 | 17.73 | 18.87 | 18.85 | 19.24 |
| 17 | 17.95 | 19.18 | 19.54 | 18.52 |
| 19 | 18.01 | 19.15 | 18.96 | 19.3 |
| 21 | 18.94 | 19.15 | 19.4 | 20.18 |
| 24 | 18.52 | 19.02 | 19.32 | 19.43 |
| 26 | 19.81 | 20.07 | 19.95 | 19.59 |
| 28 | 18.92 | 18.99 | 19.89 | 19.43 |
| 31 | 19.68 | 19.64 | 20.05 | 19.62 |
| 33 | 19.03 | 19.45 | 20.2 | 20.22 |
| 35 | 20.21 | 20.12 | 20.06 | 20.85 |
| 38 | 19.89 | 19.96 | 20.26 | 20.79 |
| 40 | 20 | 20.83 | 20.78 | 21.04 |
| 42 | 19.69 | 20.98 | 21.02 | 21.9 |
| 45 | 19.98 | 20.95 | 20.68 | 22.32 |

TABLE 3

Immune-competent animal model: Individual mouse body weights of Group 2 – Saline + Control Ab treated mice.

| | Group 2 – Saline + Control Ab – Mouse no. | | | | | | | |
|---|---|---|---|---|---|---|---|---|
| Study Day | 1519 | 1520 | 1521 | 1522 | 1527 | 1528 | 1529 | 1530 |
| −2 | 17.44 | 17.31 | 17.24 | 16.41 | 15.79 | 17.94 | 16.52 | 15.79 |
| 0 | 17.49 | 17.1 | 17.21 | 15.46 | 15.74 | 17.11 | 17.13 | 15.75 |
| 3 | 17.59 | 17.6 | 16.96 | 16.39 | 15.73 | 17.77 | 16.31 | 15.85 |

TABLE 3-continued

Immune-competent animal model: Individual mouse body weights of Group 2 – Saline + Control Ab treated mice.

| | Group 2 – Saline + Control Ab – Mouse no. | | | | | | | |
|---|---|---|---|---|---|---|---|---|
| Study Day | 1519 | 1520 | 1521 | 1522 | 1527 | 1528 | 1529 | 1530 |
| 5 | 17.71 | 17.61 | 16.85 | 16.02 | 16.13 | 18.14 | 17.08 | 16.41 |
| 7 | 18.37 | 18.11 | 17.76 | 16.23 | 16.88 | 18.19 | 17.15 | 16.76 |
| 10 | 17.98 | 18.5 | 18.58 | 16.07 | 17.39 | 18.72 | 17.46 | 17.29 |
| 12 | 19.2 | 19.14 | 18.63 | 17.01 | 17.36 | 18.62 | 17.54 | 16.9 |
| 14 | — | 18.41 | 16.55 | 16.54 | 17.28 | 18.72 | 17.57 | 16.23 |
| 17 | — | 18.82 | — | 16.75 | 18.06 | 18.97 | 18.13 | — |
| 19 | — | 19.58 | — | 17.32 | 17.86 | 19.08 | 17.86 | — |
| 21 | — | 19.31 | — | 17.4 | 17.22 | 19.54 | 18.73 | — |
| 24 | — | 19.86 | — | 18.11 | — | 20.24 | 18.5 | — |
| 26 | — | 19.92 | — | 18.79 | — | 20.4 | 19.84 | — |
| 28 | — | 20.49 | — | 19.02 | — | 19.7 | 20.14 | — |
| 31 | — | 20.69 | — | 19.4 | — | — | 21.43 | — |

TABLE 4

Immune-competent animal model: Individual mouse body weights of Group 3 – Saline + anti-PD-1 treated mice.
Group 3 – Saline + anti-PD-1 – Mouse no.

| Study Day | 1523 | 1524 | 1525 | 1526 | 1535 | 1536 | 1537 | 1538 |
|---|---|---|---|---|---|---|---|---|
| −2 | 16.03 | 17.41 | 16.25 | 16.95 | 17.18 | 15.65 | 15.25 | 17.14 |
| 0 | 16.66 | 17.63 | 16.08 | 16.73 | 16.68 | 15.6 | 15.81 | 16.64 |
| 3 | 16.77 | 17.8 | 16.78 | 16.96 | 16.85 | 15.64 | 15.93 | 16.88 |
| 5 | 17.61 | 18.56 | 17.07 | 17.53 | 17.07 | 16.29 | 16.21 | 17.18 |
| 7 | 18.08 | 18.37 | 17.32 | 17.34 | 17.89 | 16.64 | 16.71 | 18.03 |
| 10 | 18.33 | 19.48 | 17.58 | 17.49 | 17.92 | 16.75 | 17.53 | 18.12 |
| 12 | 18.57 | 19.17 | 18.35 | 16.83 | 18.41 | 16.72 | 17.69 | 18.87 |
| 14 | 18.68 | 19.55 | 17.61 | 14.06 | — | 16.97 | 16.25 | 18.17 |
| 17 | 19.03 | 19.72 | 17.76 | — | — | — | — | 19.43 |
| 19 | 18.8 | 19.49 | 17.54 | — | — | — | — | 19.95 |
| 21 | 19.47 | 20.38 | 17.93 | — | — | — | — | 20.22 |
| 24 | 18.96 | 20.14 | 18.08 | — | — | — | — | 20.31 |
| 26 | 19.66 | 20.8 | 18.3 | — | — | — | — | 20.34 |
| 28 | 19.42 | 20.27 | 18.61 | — | — | — | — | 20.6 |
| 31 | 20.37 | 21.3 | 18.24 | — | — | — | — | 20.65 |
| 33 | — | 20.9 | 18.52 | — | — | — | — | 21.37 |
| 35 | — | 21.54 | 18.68 | — | — | — | — | 21.58 |
| 38 | — | 23.02 | 19.34 | — | — | — | — | 22.4 |
| 40 | — | 23.47 | 19.91 | — | — | — | — | 23.12 |
| 42 | — | — | 20.34 | — | — | — | — | — |
| 45 | — | — | 21.05 | — | — | — | — | — |

TABLE 5

Immune-competent animal model: Individual mouse body weights of Group 4 – UV CVA21 + Control Ab treated mice.

| | Group 4 – UV CVA21 + Control Ab – Mouse no. | | | | | | | |
|---|---|---|---|---|---|---|---|---|
| Study Day | 1551 | 1552 | 1553 | 1554 | 1555 | 1556 | 1557 | 1558 |
| −2 | 16.05 | 14.82 | 16.43 | 15.56 | 16.09 | 14.88 | 15.62 | 16.9 |
| 0 | 16.12 | 14.99 | 16.88 | 15.42 | 15.97 | 15.23 | 15.79 | 16.64 |
| 3 | 16.66 | 15.45 | 17.32 | 16.07 | 15.92 | 15.67 | 16.36 | 17.01 |
| 5 | 16.98 | 15.65 | 17.49 | 16.41 | 16.02 | 16.02 | 16.09 | 17.19 |
| 7 | 17.2 | 16.35 | 18.22 | 16.63 | 16.6 | 16.2 | 16.67 | 17.8 |
| 10 | 18.09 | 15.18 | 18.26 | 17.48 | 16.4 | 15.23 | 16.62 | 17.78 |
| 12 | 17.81 | 15.66 | 18.94 | 17.1 | 16.69 | — | — | 18.2 |
| 14 | 17.92 | 16.02 | 18.58 | 17.35 | 16.33 | — | — | 17.74 |
| 17 | — | 16.03 | 18.66 | 17.64 | 16.62 | — | — | 17.27 |
| 19 | — | 16.12 | 18.77 | 17.05 | 17.13 | — | — | 18.41 |
| 21 | — | 16.45 | 19.43 | 17.85 | 17.21 | — | — | 18.7 |
| 24 | — | 17.45 | 19.82 | 17.75 | 17.82 | — | — | 19.41 |

TABLE 5-continued

Immune-competent animal model: Individual mouse body weights of Group 4 – UV CVA21 + Control Ab treated mice.

| | Group 4 – UV CVA21 + Control Ab – Mouse no. | | | | | | | |
|---|---|---|---|---|---|---|---|---|
| Study Day | 1551 | 1552 | 1553 | 1554 | 1555 | 1556 | 1557 | 1558 |
| 26 | — | 17.71 | 21.26 | 18.66 | 17.9 | — | — | 19.89 |
| 28 | — | 17.91 | 18.66 | 18.7 | 19.14 | — | — | 18.77 |
| 31 | — | 19.09 | — | 19.19 | 18.73 | — | — | — |
| 32 | — | 17.9 | — | — | — | — | — | — |
| 33 | — | — | — | 19.63 | 20.53 | — | — | — |
| 35 | — | — | — | — | 20.88 | — | — | — |

TABLE 6

Immune-competent animal model: Individual mouse body weights of Group 5 – UV CVA21 + anti-PD-1 treated mice.

| | Group 5 – UV CVA21 + anti-PD-1 – Mouse no. | | | | | | | |
|---|---|---|---|---|---|---|---|---|
| Study Day | 1539 | 1540 | 1541 | 1542 | 1547 | 1548 | 1549 | 1550 |
| -2 | 16.96 | 15.96 | 17.42 | 16.43 | 18.51 | 15.41 | 15.61 | 17.99 |
| 0 | 17.05 | 15.9 | 17.15 | 16.45 | 17.39 | 15.82 | 15.34 | 17.34 |
| 3 | 16.96 | 16.5 | 16.97 | 17 | 18.72 | 16.8 | 15.9 | 18.09 |
| 5 | 17.53 | 17.06 | 17.38 | 17.14 | 18.18 | 16.88 | 15.51 | 17.87 |
| 7 | 17.88 | 17.06 | 18.3 | 17.31 | 18.93 | 17.16 | 16.33 | 18.51 |
| 10 | 18.24 | 17.97 | 18.19 | 17.61 | 18.37 | 17.95 | 16.38 | 18.17 |
| 12 | 18.93 | 17.71 | 19.14 | 17.72 | 19.84 | 18.23 | 16.47 | 18.58 |
| 14 | 17.72 | 18.16 | 18.59 | 17.83 | 19.42 | 17.82 | 16.52 | 19.06 |
| 17 | — | 17.65 | 19.03 | 17.68 | 19.57 | 18.48 | 16.93 | 18.78 |
| 19 | — | 18.11 | 18.73 | 18.36 | 19.94 | 19.21 | 16.87 | 19.21 |
| 21 | — | 18.33 | 18.78 | 18.11 | 19.93 | 19.1 | 17.16 | 19.97 |
| 24 | — | 18.86 | 19.31 | 18.95 | 20.38 | 20.08 | 17.46 | 20.27 |
| 26 | — | 19.49 | 20.44 | 18.62 | 21.02 | 19.42 | 18.15 | 21.5 |
| 28 | — | 18.59 | 20.65 | 18.92 | 21.57 | 20.06 | 18.17 | 21.35 |
| 31 | — | 18.95 | 22.04 | 18.64 | 21.66 | 19.93 | — | 22.79 |
| 32 | — | 19.29 | 21.37 | — | — | — | — | — |
| 33 | — | — | — | 18.81 | 23.07 | 20.78 | — | 23.53 |
| 34 | — | — | — | — | — | 20.53 | — | — |
| 35 | — | — | — | 18.94 | 23.62 | — | — | — |
| 38 | — | — | — | 19.78 | — | — | — | — |
| 40 | — | — | — | 19.55 | — | — | — | — |
| 42 | — | — | — | 20.03 | — | — | — | — |
| 45 | — | — | — | 20.39 | — | — | — | — |

TABLE 7

Immune-competent animal model: Individual mouse body weights of Group 6 – CVA21 + Control Antibody treated mice.

| | Group 6 – CVA21 + Control Ab – Mouse no. | | | | | | | |
|---|---|---|---|---|---|---|---|---|
| Study Day | 1531 | 1532 | 1533 | 1534 | 1543 | 1544 | 1545 | 1546 |
| -2 | 16.26 | 13.98 | 15.65 | 15.27 | 16.13 | 16.8 | 14.75 | 15.63 |
| 0 | 16.7 | 14.05 | 15.87 | 15.48 | 16.34 | 16.19 | 14.59 | 15.77 |
| 3 | 16.75 | 13.69 | 16.06 | 15.81 | 16.53 | 16.83 | 14.93 | 16.91 |
| 5 | 16.93 | 14.14 | 16.73 | 16.17 | 17.25 | 17.14 | 15.4 | 16.51 |
| 7 | 17.06 | 15.05 | 17.19 | 16.67 | 18.09 | 17.2 | 15.7 | 17.46 |
| 10 | 16.85 | 14.75 | 17.32 | 16.81 | 18.21 | 17.98 | 15.76 | 16.48 |
| 12 | 17.32 | 14.8 | 18.22 | 17.03 | 18.82 | 17.99 | 15.82 | 16.45 |
| 14 | 16.88 | 14.69 | 17.19 | 16.91 | 18.47 | 17.52 | 16.13 | — |
| 17 | 17.04 | 15.25 | 18.59 | 17.11 | 19.4 | 17.97 | 16.02 | — |
| 19 | 17.35 | 15.51 | 18.39 | 17.38 | 19.31 | 17.91 | 16.79 | — |
| 21 | 17.69 | 15.64 | 18.65 | 17.44 | 19.69 | 18.19 | 16.41 | — |
| 24 | 17.84 | 14.33 | 18.96 | 18.12 | 19.74 | 18.72 | 17.54 | — |
| 26 | 18.75 | — | — | 17.57 | 21.15 | 19.61 | 17.64 | — |
| 28 | 18.77 | — | — | — | 19.91 | 20.33 | 18.27 | — |
| 31 | 18.51 | — | — | — | — | 18.19 | 18.44 | — |

TABLE 7-continued

Immune-competent animal model: Individual mouse body
weights of Group 6 – CVA21 + Control Antibody treated mice.

| | Group 6 – CVA21 + Control Ab – Mouse no. | | | | | | | |
|---|---|---|---|---|---|---|---|---|
| Study Day | 1531 | 1532 | 1533 | 1534 | 1543 | 1544 | 1545 | 1546 |
| 33 | 19.37 | — | — | — | — | — | 18.98 | — |
| 35 | 19.97 | — | — | — | — | — | 20.35 | — |
| 38 | 20.96 | — | — | — | — | — | 21.01 | — |
| 40 | 21.68 | — | — | — | — | — | — | — |
| 42 | 22.37 | — | — | — | — | — | — | — |
| 45 | 24.67 | — | — | — | — | — | — | — |

TABLE 8

Immune-competent animal model: Individual mouse body
weights of Group 7 – CVA21 + anti-PD-1 treated mice.

| | Group 7 – CVA21 + anti-PD-1 – Mouse no. | | | | | | | |
|---|---|---|---|---|---|---|---|---|
| Study Day | 1559 | 1560 | 1561 | 1562 | 1563 | 1564 | 1565 | 1566 |
| -2 | 17.88 | 16.47 | 16.52 | 19.57 | 15.37 | 16.5 | 16.68 | 17.03 |
| 0 | 18.02 | 16.59 | 16.73 | 19.24 | 16.45 | 16.46 | 16.19 | 16.47 |
| 3 | 17.84 | 17.03 | 17.4 | 18.91 | 17.34 | 16.54 | 16.8 | 17.15 |
| 5 | 18.35 | 16.62 | 17.88 | 19.38 | 17.69 | 17.07 | 16.61 | 16.68 |
| 7 | 19.09 | 17.25 | 17.89 | 19.98 | 17.82 | 16.77 | 17.17 | 17.28 |
| 10 | 19.63 | 17.6 | 18.53 | 20.61 | 19.05 | 17.59 | 17.06 | 17.66 |
| 12 | 18.44 | 17.79 | 19.2 | 21.32 | 19.47 | 17.43 | 17.62 | 18.18 |
| 14 | 18.39 | 17.45 | 19.16 | 20.23 | 19.12 | 17.37 | 17.57 | 17.88 |
| 17 | 19.34 | 17.24 | 18.92 | 21.07 | 19.36 | 17.48 | 17.59 | 17.87 |
| 19 | 19.32 | 17.74 | 19.27 | 20.69 | 19.96 | 17.37 | 18.25 | 18.11 |
| 21 | 19.8 | 17.54 | 19.54 | 21.25 | 20.54 | 17.38 | 17.58 | 18.13 |
| 24 | 20.02 | 18.29 | 19.7 | 20.76 | 20.28 | 17.76 | 18.79 | 18.23 |
| 26 | 19.15 | 18.5 | 20.89 | 21.76 | 21 | 18.01 | 18.69 | 18.61 |
| 27 | 18.25 | — | — | — | — | — | — | — |
| 28 | — | 18.84 | 19.82 | 21.67 | 21.68 | 18.61 | 18.77 | 19 |
| 31 | — | 19.44 | 21.06 | 22.94 | 21.92 | 18.56 | 18.7 | 18.81 |
| 33 | — | 20.09 | 20.9 | 20.88 | 18.94 | 19.37 | 19.62 | 19.53 |
| 35 | — | 18.62 | 21.82 | — | — | 19.09 | 19.8 | 19.94 |
| 36 | — | — | — | — | — | 16.21 | — | — |
| 37 | — | 16.05 | — | — | — | — | — | — |
| 38 | — | — | 22.15 | — | — | — | 20.67 | 20.77 |
| 40 | — | — | 24.17 | — | — | — | 19.03 | 21.68 |
| 42 | — | — | 24.15 | — | — | — | — | 20.27 |
| 45 | — | — | 23.23 | — | — | — | — | 19.96 |

Tables 9, 10 and 11 are included in the Figures section of this document.

Tumour Volume Data Following Treatment with Either Saline, CVA21 or UV-Inactivated CVA21 in Combination with Anti-PD-1 or Control Antibody.

Figure 4:
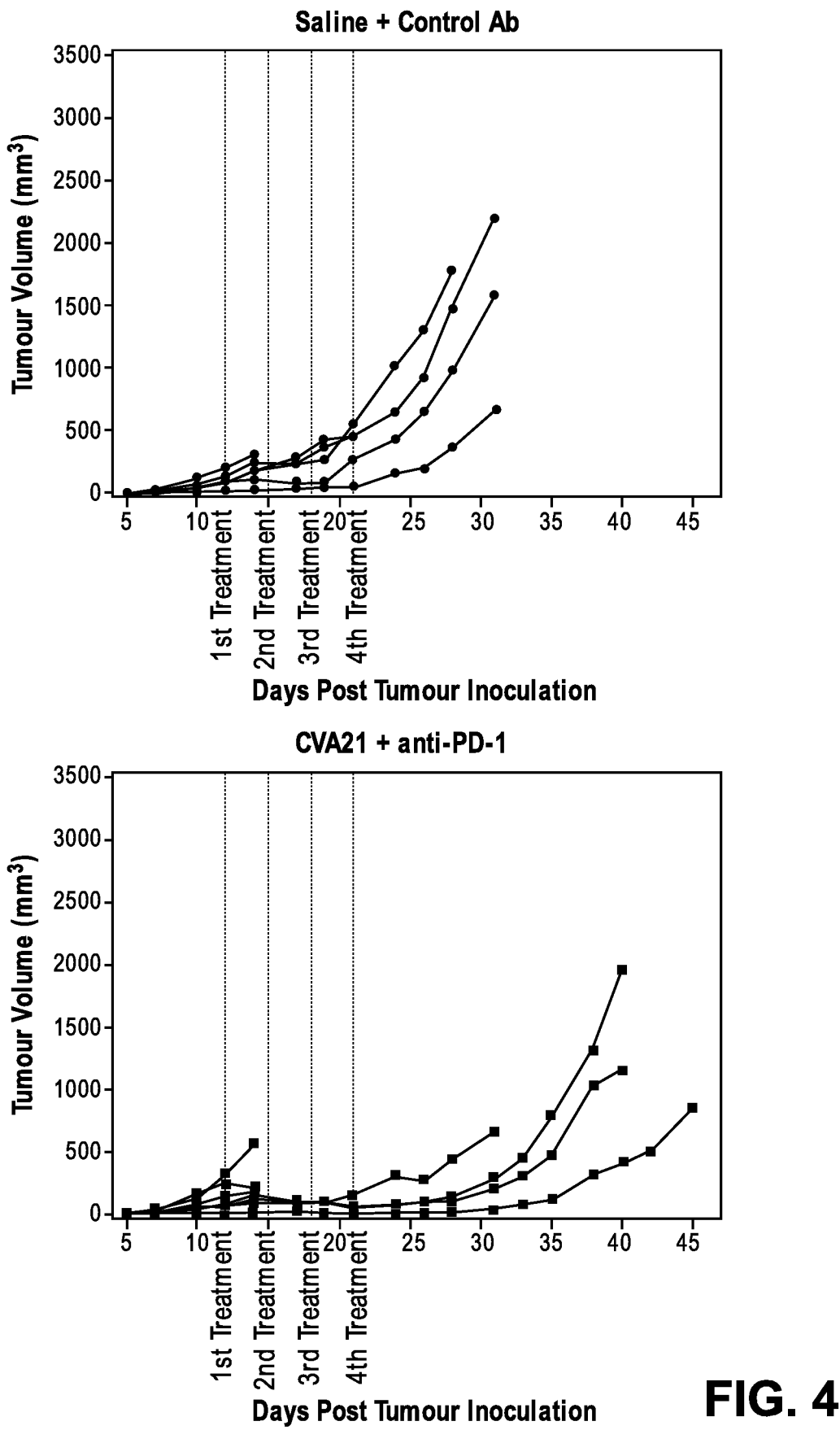
FIG. 4: Individual tumour volumes from each mouse following combination immunotherapy and CVA21 virotherapy on B16-ICAM-1 murine melanoma tumours (n=8 per group). C57BL/6 mice were injected with B16-ICAM-1 cells intradermally on the hind flank. On days 12, 15, 18 and 21 tumours were injected intratumourally with either saline, CVA21 ($1 \times 10^8$ $TCID_{50}$ [$5 \times 10^9$ $TCID_{50}$/kg]) or UV-inactivated CVA21 ($1 \times 10^8$ $TCID_{50}$ [$5 \times 10^9$ $TCID_{50}$/kg]), in combination with the control or anti-PD-1 antibody (12.5 mg/kg respectively). Treatment days are indicated by the dotted lines. During the treatment period there was a noticeable trend of delayed tumour growth in the anti-PD-1 treated groups vs control antibody groups. The tumour take rate in the saline+anti-PD-1 treatment group was quite variable and at least three animals were euthanased before the course of therapy was completed.
Figure 4:
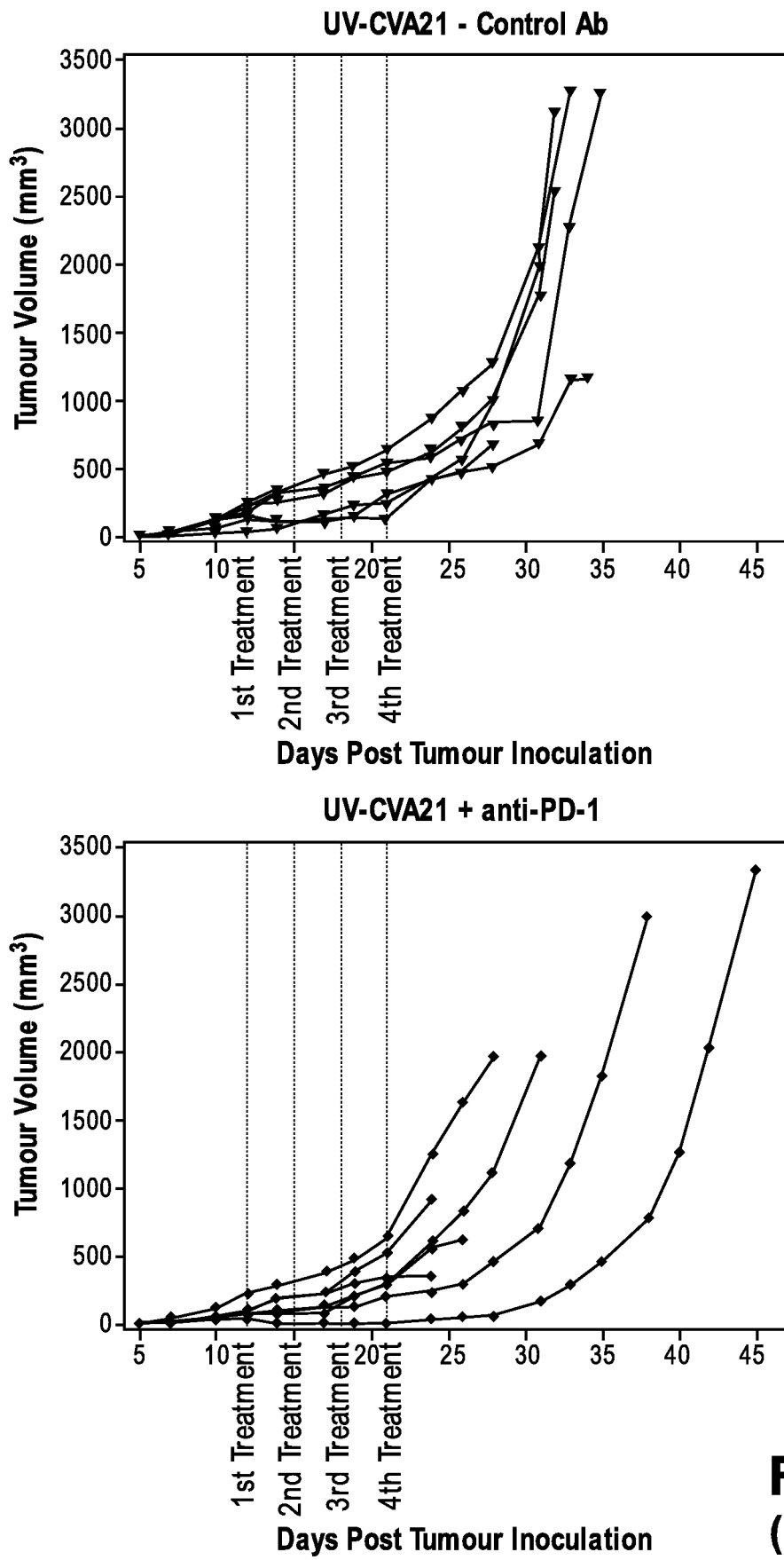
Figure 4:
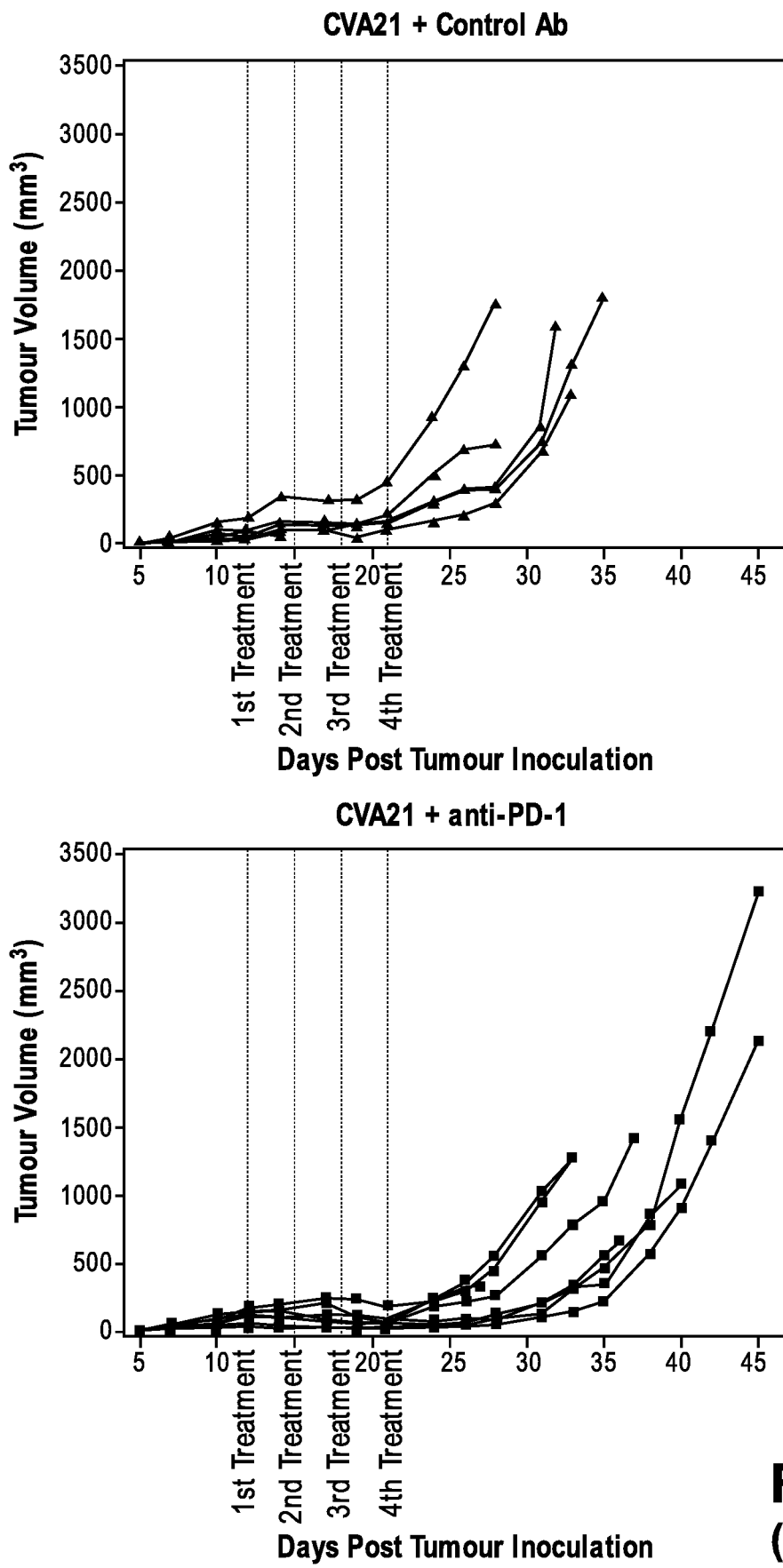
Figure 5A:
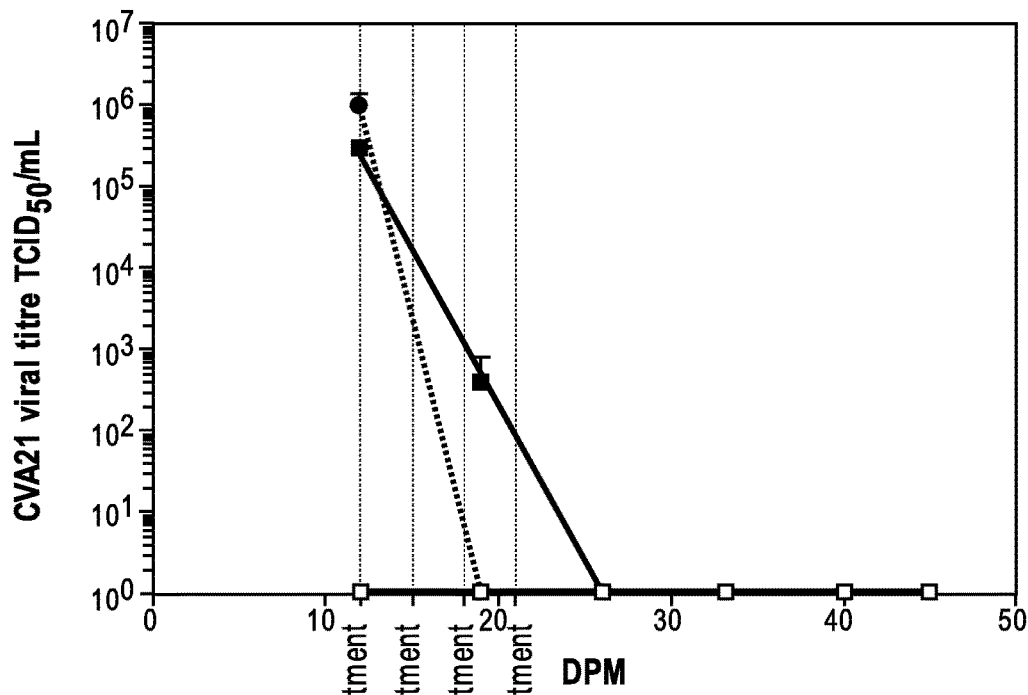
FIG. 5A-5B: Detection of A) viremia and B) anti-CVA21 neutralising antibodies following CVA21 oncolytic virotherapy in combination with anti-PD-1 immunotherapy. Graphs show mean+SEM (n=8 at the commencement of the study). The differences in neutralising antibody levels between the CVA21+anti-PD-1 antibody vs CVA21+control antibody were significant on day 33 (p=0.04 one-tailed t-test).
Figure 5B:
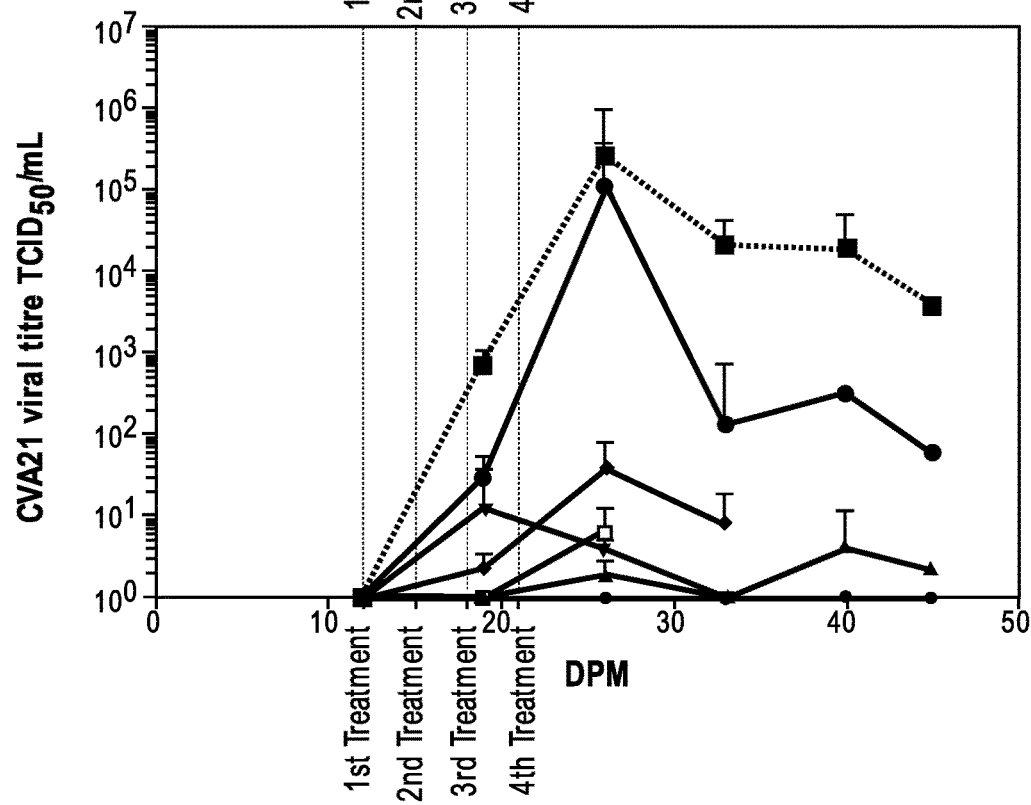
Figure 6:
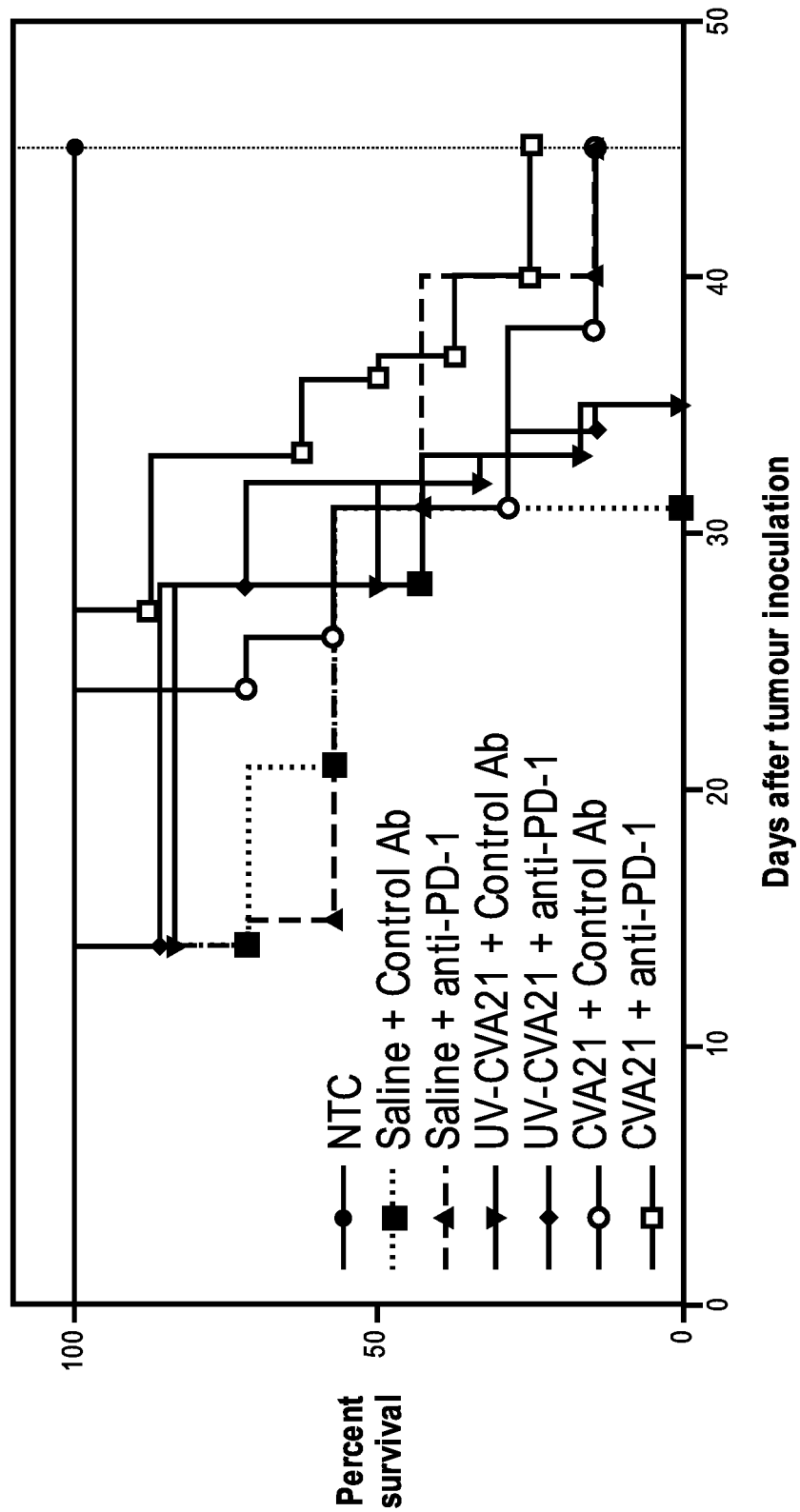
FIG. 6: Survival of C57BL/6 mice following treatment saline, UV-CVA21 or CVA21 in combination with the control antibody or anti-PD-1. The dotted line at day 45 indicates the end/termination of the experiment.

Tumour volumes were measured twice a week using electronic vernier calipers. By day 31, all saline+control antibody treated mice were euthanased due to progressive disease evidenced by tumour volume tumour ulceration. As shown in FIG. 4, little anti-tumour activity was observed in the UV-CVA21+control antibody treated tumours. By 35 days all tumour volumes had escalated reaching the maximal humane endpoint and required euthanasia. There was a high degree of variability in initial tumour starting volumes and the most appropriate control for active CVA21+anti-PD-1 was deemed the UV-CVA21+anti-PD-1 treated group rather than saline+anti-PD-1 (3 animals required euthanasia prior to completion of therapy). A comparison of tumour volumes at day 24 between UV-CVA21+anti-PD-1 and CVA21+anti-PD-1 treatments revealed that there was a significant difference using a two-tailed t-test ($p<0.0039$). The significant reduction in tumours between mice in the live CVA21+anti-PD-1 group compared to the UV-inactivated CVA21 was most notable during the active phase of treatment and eventually the tumours relapsed in most groups.

Viral Clearance from Immune-Competent Mice and Increased Levels of Anti-CVA21 Neutralising Antibodies Infectious CVA21 was detected in the serum of virus treated animals approximately 45 minutes post intratumoural injection of virus on day 12. The circulating virus in the blood was eliminated within the first week by day 19, despite additional treatments with CVA21 intratumourally. Animals that were treated with live CVA21 produced the highest levels of CVA21 neutralising antibodies, reaching a maximum at day 26. Given these mice have a functional immune system, the clearance of CVA21 from the blood stream was not unexpected. Surprisingly, the administration of the anti-PD-1 antibody appeared to enhance the anti-viral immune response, with these mice showing elevated levels of anti-CVA21 antibodies of greater than 1:228 neutralising units, lasting up until day 45. This may be a result of the action of the anti-PD-1 antibody allowing greater degree of viral replication and subsequent production of anti-viral antibodies. This finding raises the possibility that not only an enhanced level of anti-viral antibodies were produced but a higher level of specific anti-tumour antibodies were generated in this process, such anti-tumour antibodies may result in clinical benefit as a consequence of reducing tumour burden (antibody-dependent cellular cytotoxicity).

Enhanced Survival in Mice Treated with CVA21 in Combination with Anti-PD-1 Versus Saline and Anti-PD-1

Figure 7A:
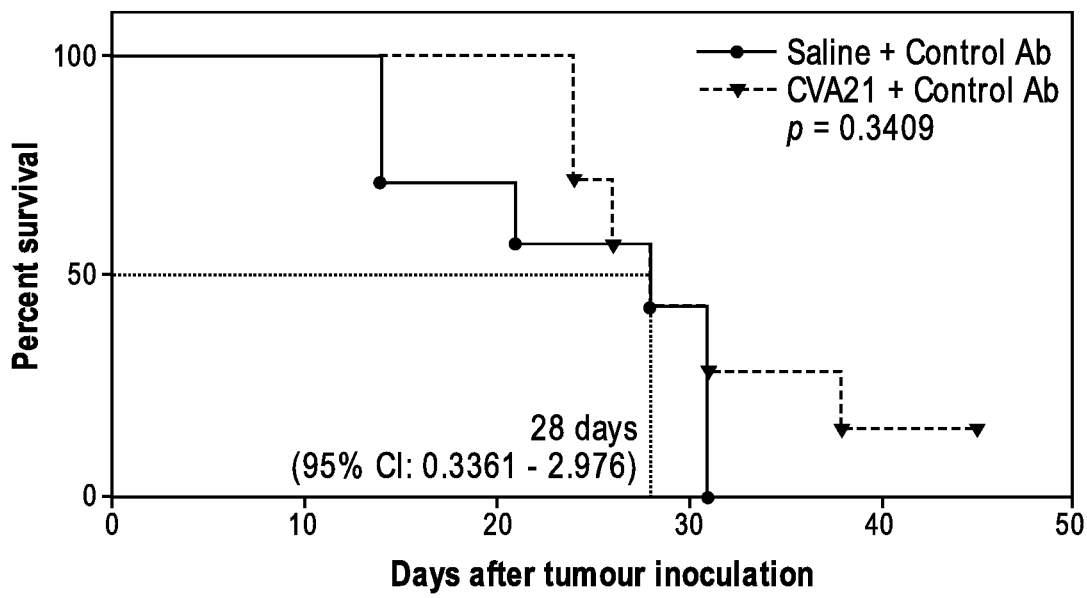
Figure 7B:
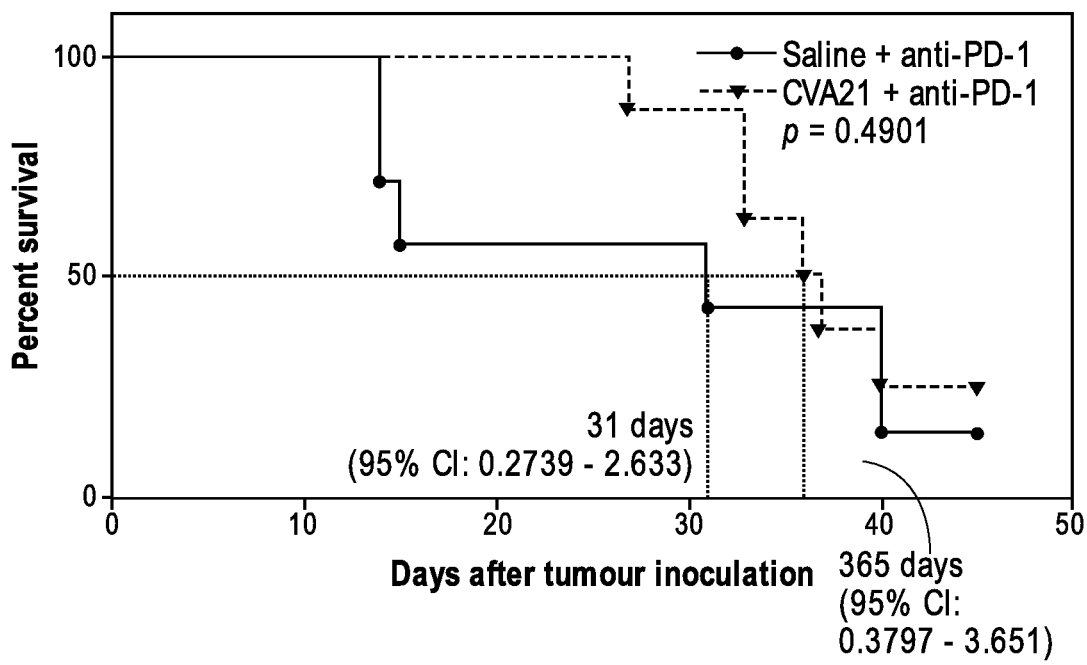
Figure 7C:
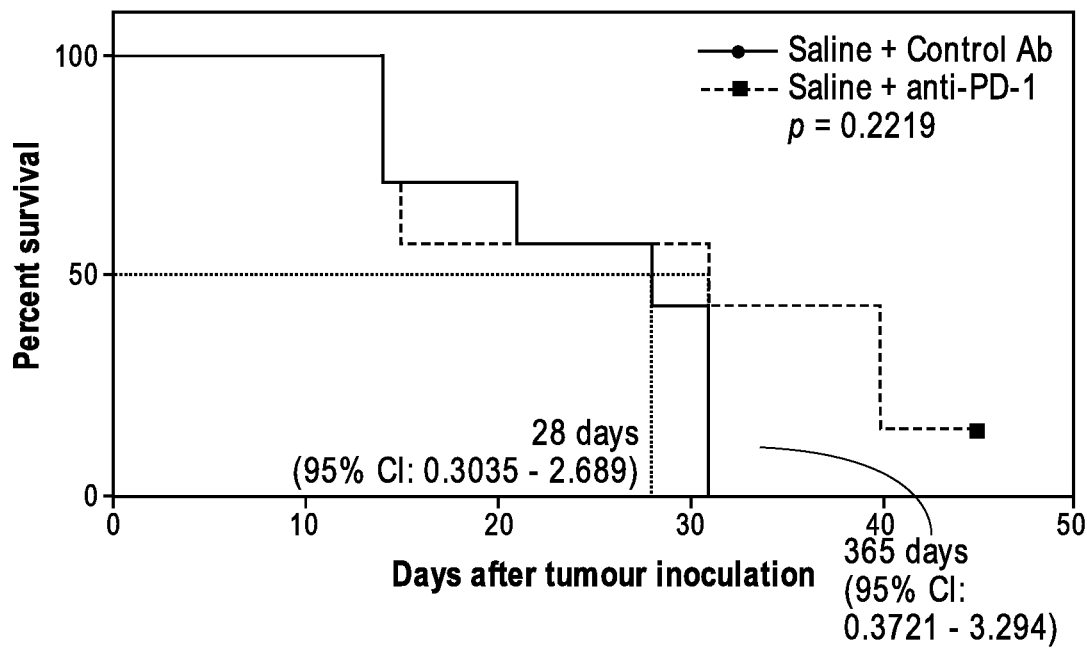
Figure 7D:
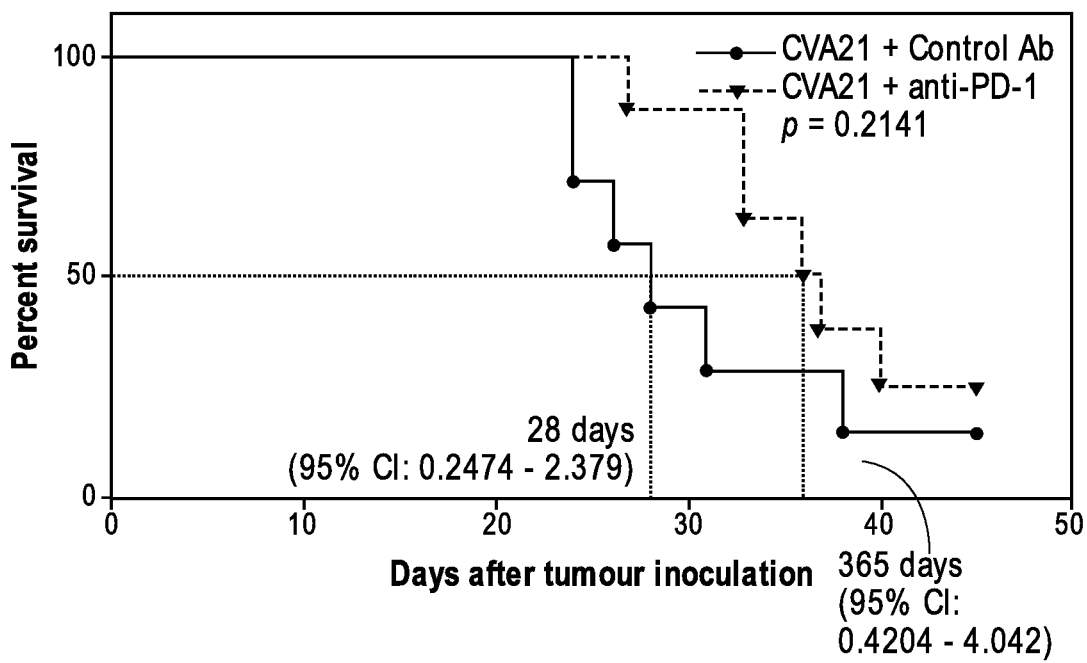
Figure 7E:
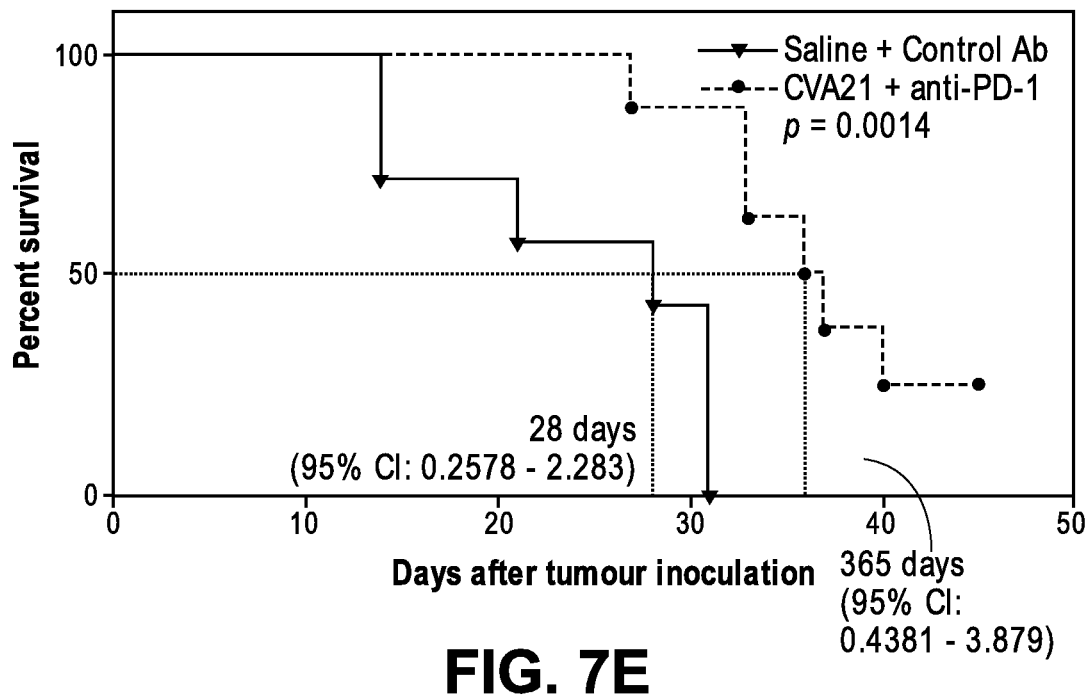
Figure 7F:
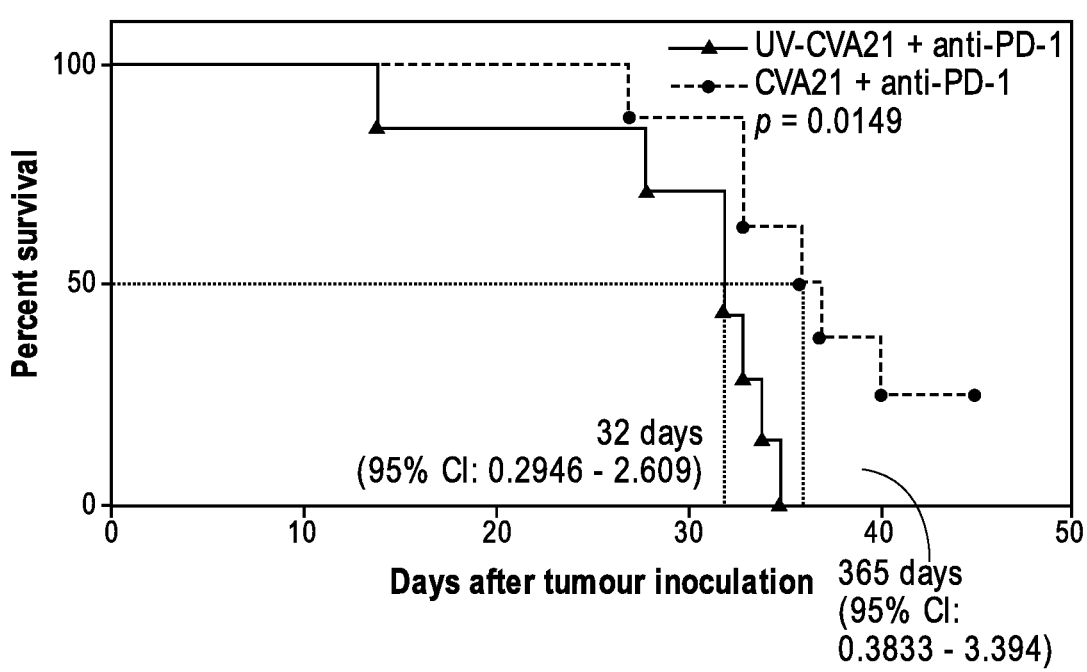

CVA21 in combination with the anti-PD-1 antibody demonstrated a statistically significant improvement in overall survival compared to the saline+Control antibody group (p=0.014 Log-rank [Mantel-Cox] test) (FIG. 7E). Comparing the saline+anti-PD-1 and saline+control antibody group, there was no statistically significant difference. This suggests that there was no difference between the control antibody and the anti-PD-1 antibody on survival. When the saline+anti-PD-1 survival curve was compared with the CVA21+anti-PD-1 treatment group there was no statistical difference (p=0.4901 Log-rank [Mantel-Cox] test) (FIG. 7B). This finding suggests that the main effect of survival was predominantly anti-PD-1 based, however somewhat unexpectedly the comparison between UV-inactivated CVA21 and active CVA21 groups together with anti-PD-1 revealed that live CVA21 gave an additional significant survival time advantage. Due to a high degree of starting tumour variability and early term sacrifice, stringent analysis of relative survival benefits were significantly challenged. However a notable survival benefit trend of live CVA21+anti-PD-1 treated group compared to the saline+anti-PD-1 group was observed during the active treatment period.

Discussion

The results indicated that the use of live CVA21 in combination with the anti-PD-1 antibody gave the best overall survival compared to the saline+control antibody treatment group. CVA21 in combination with the anti-PD-1 antibody demonstrated a statistically significant improvement in overall survival compared to the saline+control antibody group (p=0.014 Log-rank [Mantel-Cox] test) (FIG. 7E). Comparing the saline+anti-PD-1 and saline+control antibody group, there was no statistically significant difference. This suggests that there was no difference between the control antibody and the anti-PD-1 antibody on survival. When the saline+anti-PD-1 survival curve was compared with the CVA21+anti-PD-1 treatment group there was no statistical difference (p=0.4901 Log-rank [Mantel-Cox] test) (FIG. 7B). This finding suggests that the main effect of survival was predominantly anti-PD-1 based, however addition of CVA21 did not enhance it significantly compared to saline based on our limited group sizes. Interestingly the comparison between UV-inactivated CVA21 and active CVA21 groups together with anti-PD-1 showed that live CVA21 gave an a slightly longer survival time and was statistically significant. This fits our hypothesis that actively replicating CVA21 and the lysis of tumour cells may stimulate anti-tumoural immunity more effectively in the presence of immunostimulatory anti-PD-1 antibodies compared to inactivated viral particles. The survival of the UV-inactivated CVA21+anti-PD-1 antibody group was not statistically different to that of the UV-inactivated CVA21+control antibody, or the CVA21+control antibody group.

An important finding of this study was that tumour bearing mice treated CVA21+anti-PD-1 showed an overall survival benefit that related to retardation of tumour growth and reduction in tumour ulceration. During the active phase of treatment, animals treated with the CVA21+anti-PD-1 antibody showed a slowing of disease progression vs control groups.

Example 2: Oncolytic CVA21 Virotherapy in Combination with the Immunostimulatory Antibody Anti-PD-1: Tumor Rechallenge Study This study was an extension of the work documented in Example 1, investigating the effectiveness of Coxsackievirus A21 (CVA21) oncolytic virotherapy in combination with the immunostimulatory antibody anti-PD-1 in a B16-ICAM-1 murine model of malignant melanoma. A timeline representation of Example 2 is shown in FIG. 8. As different to Example 1, the overall timeline of Example 2 was 66 days and included a "tumor re-challenge" as described in more detail below. Materials and methods used in Example 2 were otherwise generally as described in Example 1, although the mice used for Example 2 were aged between four to six weeks.

Mice were implanted with B16-ICAM-1 tumors intradermally ($2\times10^5$ cells) on the right hind flank and allowed to establish for 6 days before commencement of therapy. Mice were treated with either saline or CVA21 ($1\times10^8$ TCID$_{50}$ [$5.56\times10^9$ TCID$_{50}$/kg]), in combination with either a murine anti-PD-1 antibody or a matched control antibody (12.5 mg/kg) on days 6, 9, 12 and 15. Saline or CVA21 treatments were administered intratumorally while the anti-PD-1 and control antibodies were administered intraperitoneally (n=12 per group). Additional top-up injections of saline or CVA21 ($1\times10^8$ TCID$_{50}$ [$5.56\times10^9$ TCID$_{50}$/kg]) were administered at weekly intervals thereafter for a period of four weeks. The primary B16-ICAM-1 melanoma tumors were monitored regularly every 2 to 3 days using digital calipers and tumor volumes calculated were based on the formula for a spheroid using the two longest perpendicular axes in the x/y plane of the tumor. Animals with tumors showing signs of ulceration, weight loss of >10% or tumor volumes greater than 2500 mm$^3$ were euthanized.

At day 31, the remaining animals were intradermally rechallenged with $1\times10^5$ B16 murine melanoma cells (that lacked the human-ICAM-1 receptor) to determine whether mice had developed a robust anti-tumoral immune response following CVA21 virotherapy in combination anti-PD-1 therapy. Of the 37 animals that were re-challenged, all animals eventually developed palpable tumors, however there was a trend indicating that the onset of B16 tumor growth was delayed by CVA21+anti-PD-1 therapy of existing B16-ICAM-1 tumors.

Animals treated with CVA21 in combination with the anti-PD-1 antibody showed a statistically significant extension in survival compared to animals in the saline+anti-PD-1 antibody and saline+control antibody group (median survival of 60 vs 45 vs 28 days respectively) suggesting that CVA21+anti-PD-1 may be beneficial in a clinical setting. The use of CVA21+anti-PD-1 was found to be well tolerated in this immunocompetent mouse model of melanoma with no adverse events relating to the agents tested.

Body Weights Following Treatment with Either Saline or CVA21 in Combination with Anti-PD-1 or Control Antibody.

Body weights of individual animals were collected and analysed as described in Example 1. No statistically significant differences in the mean body weight were observed between the treatment groups and NTC mice at any time points (results not shown; multiple t-tests corrected for multiple comparisons using the Holm-Sidak method) [Prism 6 for Mac OS X Version 6.0c, GraphPad Software, La Jolla Calif. USA, www.graphpad.com]. Animals appeared to tolerate the CVA21 and anti-PD-1 therapy well and there were no observable toxicities from the treatments. The decrease in weight was in the majority of cases linked to tumor ulceration and associated tumor burden.

Tumor Volumes of Primary B16-ICAM-1 Nodules.

Figures 9A, 9B:
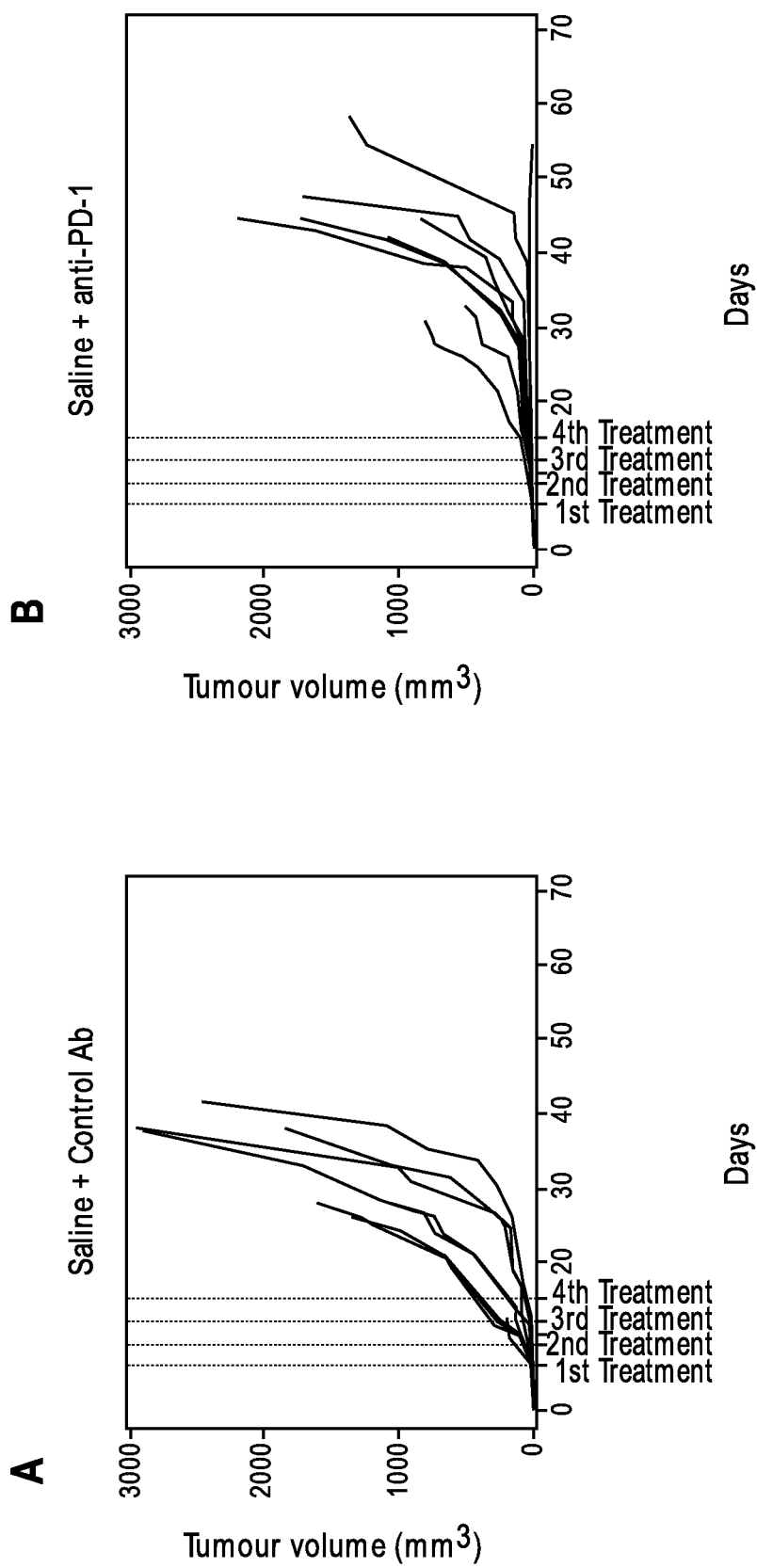
FIG. 9A-9D: Individual tumor volumes from each mouse following combination immunotherapy and CVA21 virotherapy on B16-ICAM-1 murine melanoma tumors (n=12 per group). A) Saline+Control Ab, B) Saline+anti-PD-1, C) CVA21+Control Ab, D) CVA21+anti-PD-1. C57BL/6 mice were injected with B16-ICAM-1 cells intradermally on the hind flank. On days 6, 9, 12 and 15 tumors were injected intratumorally with either saline or CVA21 ($1 \times 10^8$ $TCID_{50}$ [$5.56 \times 10^9$ $TCID_{50}$/kg]), in combination with the control or anti-PD-1 antibody (12.5 mg/kg respectively). Treatment days are indicated by the dotted lines. Additional intratumoral virus injections ($1 \times 10^8$ $TCID_{50}$ [$5.56 \times 10^9$ $TCID_{50}$/kg]) were administered at days 19, 26, 33 and 40. During the treatment period there was a noticeable trend of delayed tumor growth in the anti-PD-1 treated groups vs control antibody groups.
Figures 9C, 9D:
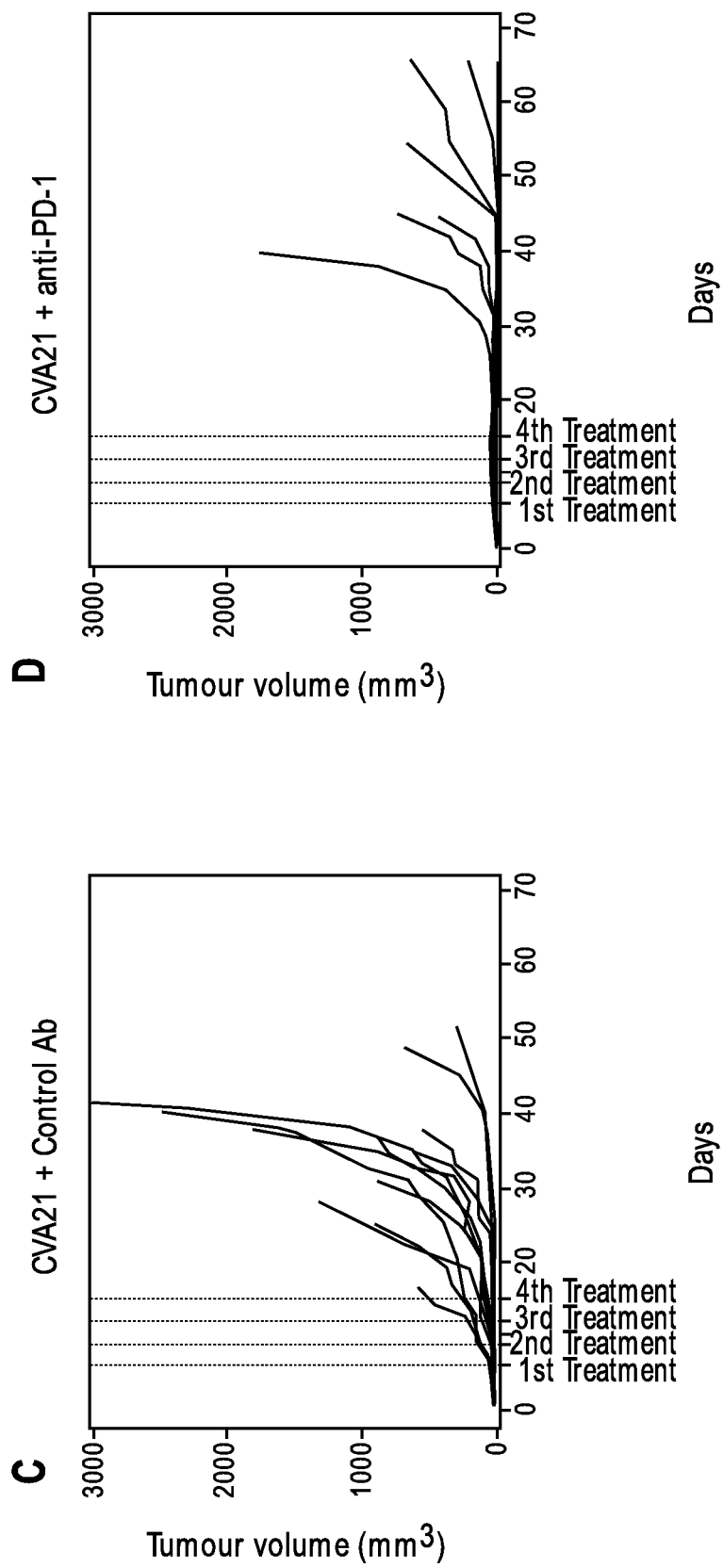

Tumor volumes were measured three times a week using electronic vernier calipers. By day 42, all saline+control antibody treated mice were euthanized due to progressive disease evidenced by tumor volume tumor ulceration. As shown in FIG. 9, little anti-tumor activity was observed in the saline+control antibody treated tumors. All tumor volumes had escalated reaching the maximal humane endpoint and required euthanasia. The CVA21+anti-PD-1 treatment group showed the best responses with a notable delay in tumor onset and only six animals showing signs of primary tumor growth towards the latter half of the study.

Tumor Volumes of Secondary B16 Nodules.

Figures 10A, 10B, 10C, 10D:
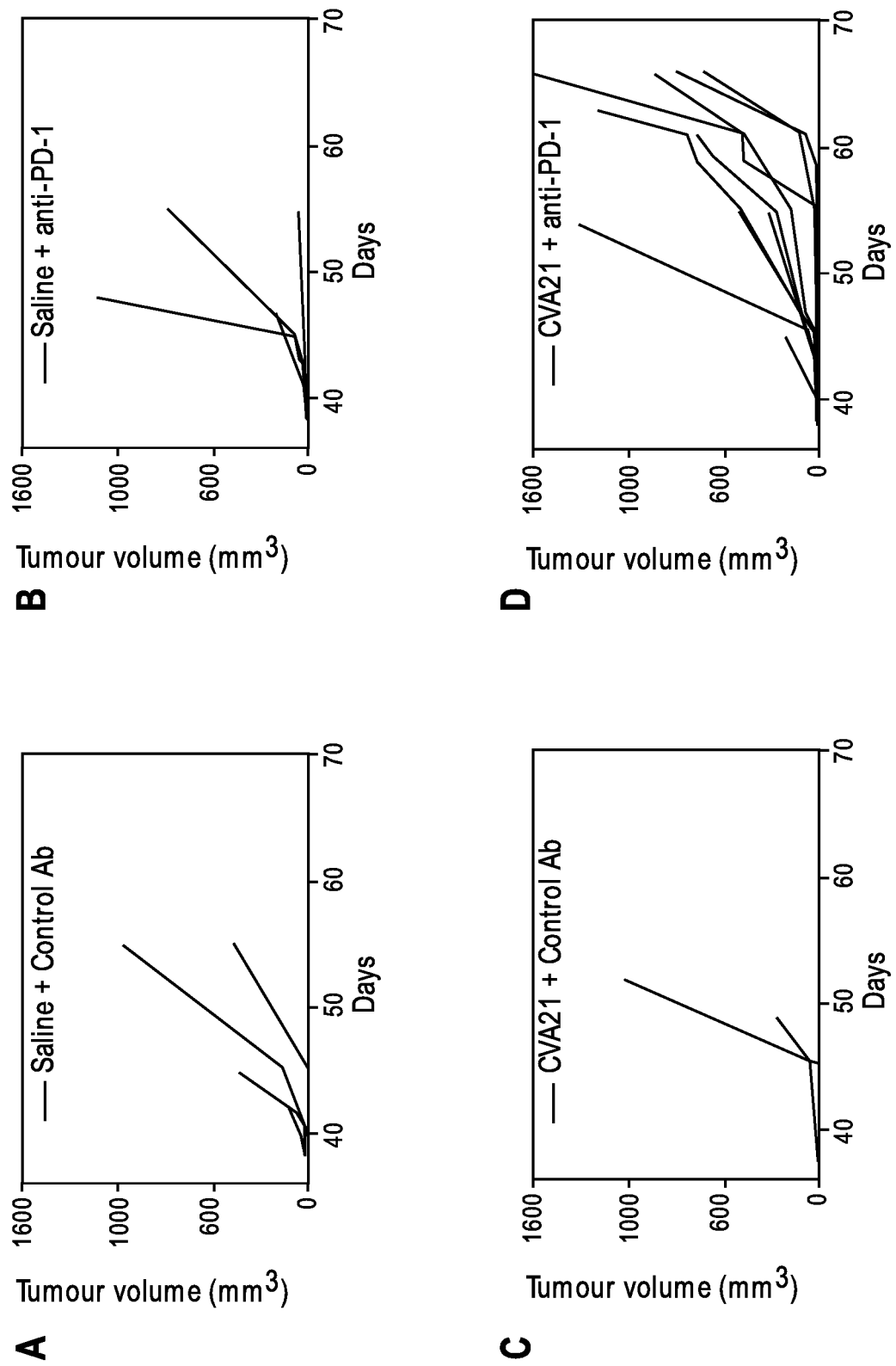
FIG. 10A-10D: Tumor volumes of secondary B16 tumor nodules. Individual tumor volumes from each mouse following rechallenge with B16 tumor cells ($1 \times 10^5$) on the right hind flank at day 31. A) Saline+Control Ab, B) Saline+anti-PD-1, C) CVA21+Control Ab, D) CVA21+anti-PD-1. All animals eventually developed palpable tumors, however, there was a trend indicating that the onset of B16 tumor growth was delayed by CVA21+anti-PD-1 therapy.

To establish whether a robust anti-tumoral immune response had developed following CVA21 therapy in combination with anti-PD-1 treatment, mice were rechallenged with B16 murine melanoma cells. B16 cells lack the human ICAM-1 receptor and are therefore resistant to CVA21 therapy. These cells are antigenically similar to the B16 cells used to generate the B16-ICAM-1 cell line and were used to identify the presence of anti-tumoral immune responses that may have resulted following oncolysis of the primary tumor. As seen in FIG. 10, B16 tumors eventually developed in all of the mice rechallenged with B16 cells, however at day 45 the average tumor volume of the saline+control antibody group was statistically larger than the saline+anti-PD-1, CVA21+control antibody and CVA21+anti-PD-1 antibody groups (Two-way ANOVA).

Enhanced Survival in Mice Treated with CVA21 in Combination with Anti-PD-1 Versus Saline and Anti-PD-1.

Figures 11A, 11B:
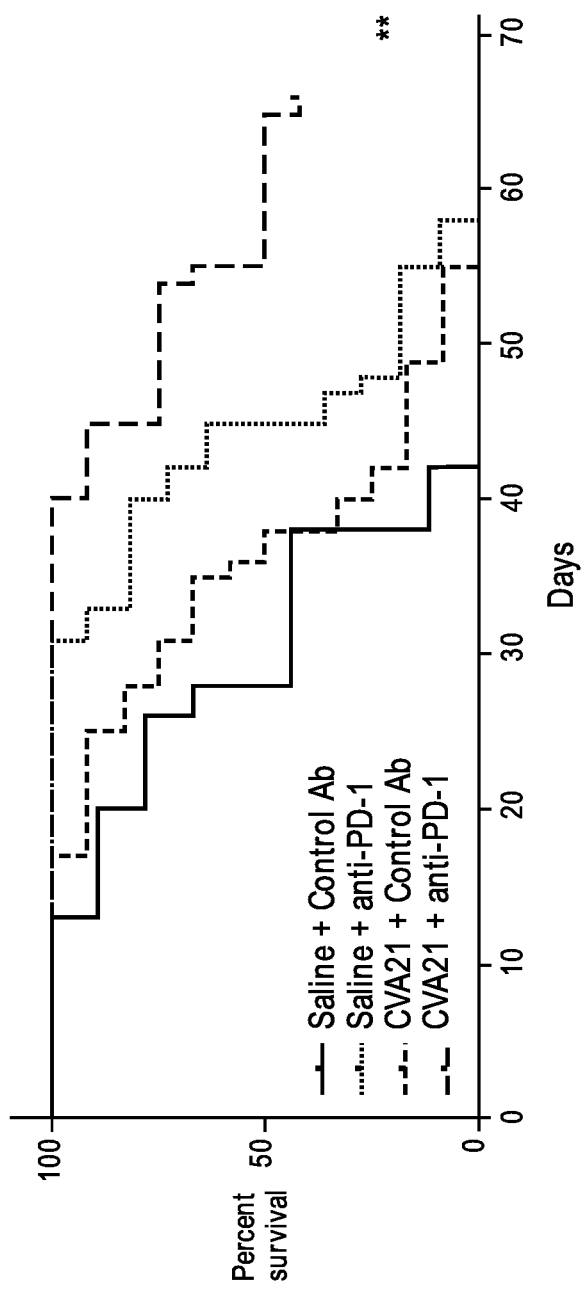
FIG. 11A-11B: Survival of C57BL/6 mice following treatment with saline or CVA21 in combination with the control antibody or anti-PD-1. A) When the saline+anti-PD-1 survival curve was compared with the CVA21+anti-PD-1 treatment group, there was a statistical difference (p=0.0026 Log-rank [Mantel-Cox] test). B) CVA21 used in combination with the anti-PD-1 antibody gave a significant survival advantage (median survival of 45 vs 60 days for saline+anti-PD-1 and CVA21+anti-PD-1 respectively). The study was terminated at day 66.

CVA21 in combination with the anti-PD-1 antibody demonstrated a statistically significant improvement in overall survival compared to the saline+Control antibody group (p<0.0001 Logrank [Mantel-Cox] test) (FIG. 11). Comparing the CVA21+control antibody and the saline+control antibody group, there was no statistically significant difference. When the saline+anti-PD-1 survival curve was compared with the CVA21+anti-PD-1 treatment group there was a statistical difference (p=0.0026 Log-rank [Mantel-Cox] test) (FIG. 11). This finding suggests that CVA21 used in combination with the anti-PD-1 antibody gave a significant survival advantage (median survival of 45 vs 60 days for saline+anti-PD-1 and CVA21+anti-PD-1 respectively).

Discussion

The Example 2 results indicated that the use of CVA21 in combination with the anti-PD-1 antibody improved the overall survival of tumor bearing mice compared to animals receiving the saline+anti-PD-1 antibody treatment group. CVA21 in combination with the anti-PD-1 antibody demonstrated a statistically significant improvement in overall survival compared to the saline+control antibody group (p<0.0001 Log-rank [Mantel-Cox] test) (FIG. 11). The treatment regime of CVA21 in combination with the anti-PD-1 was well tolerated with no adverse events attributed to the test articles. The main finding of this study was that tumor bearing mice treated CVA21+anti-PD-1 showed an overall survival benefit that related to retardation of tumor growth. Animals treated with the CVA21+anti-PD-1 antibody showed a slowing of disease progression vs control groups and were more resistant to rechallenge with a secondary B16 tumor.

Example 3: Oncolytic CVA21 Virotherapy in Combination with the Immunostimulatory Antibody Anti-CTLA-4: Tumor Rechallenge Study This study investigates the effectiveness of Coxsackievirus A21 (CVA21) oncolytic virotherapy in combination with the immunostimulatory antibody anti-CTLA-4 in a B16-ICAM-1 murine model of malignant melanoma.

Mice were implanted with B16-ICAM-1 tumors intradermally ($2\times10^5$ cells) on the right hind flank and allowed to establish for seven days before commencement of therapy. Mice were treated with either saline or CVA21 ($1\times10^8$ $TCID_{50}$ [$5.56\times10^9$ $TCID_{50}$/kg assuming a 18 g mouse]), in combination with either a murine anti-CTLA-4 antibody or a matched control antibody (12.5 mg/kg) on days 7, 10, 13 and 16. Saline or CVA21 treatments were administered intratumorally while the anti-CTLA-4 and control antibodies were administered intraperitoneally (n=12 per group). The primary B16-ICAM-1 melanoma tumors were monitored regularly every 2 to 3 days using digital calipers and tumor volumes calculated based on the formula for a spheroid using the two longest perpendicular axes in the x/y plane of the tumor. Animals with tumors showing signs of ulceration, weight loss of >10% or tumor volumes greater than 2500 mm$^3$ were euthanased. CVA21+anti-CTLA-4 therapy in B16-ICAM-1 tumor bearing mice resulted in durable tumor regression compared to all other treatment groups.

At day 37, the remaining animals were intradermally rechallenged with $2\times10^5$ B16 murine melanoma cells (that lacked the human-ICAM-1 receptor) to determine whether mice had developed a robust anti-tumoral immune response following CVA21 virotherapy in combination with anti-CTLA-4 therapy. Of the 34 animals that were rechallenged, all but six animals eventually developed palpable tumors (two saline+anti-CTLA-4 and four CVA21+anti-CTLA-4 mice remained tumor free).

Animals treated with CVA21 in combination with the anti-CTLA-4 antibody showed a statistically significant extension in survival compared to animals in the saline+control antibody group (median survival of 72 vs 39 days) as did single agent CVA21 and anti-CTLA-4 antibody alone. While there was no significant difference between CVA21+anti-CTLA-4 vs single agent anti-CTLA-4, combination CVA21+anti-CTLA-4 gave improved survival vs CVA21 alone (median survival of 72 vs 56.5 days) suggesting that this combination may be beneficial in a clinical setting. The use of CVA21+anti-CTLA-4 was found to be well tolerated in this immunocompetent mouse model of melanoma with no adverse events relating to the agents tested.

Body Weights Following Treatment with Either Saline or CVA21 in Combination with Anti-CTLA-4 or Control Antibody.

Body weights of individual animals were collected and analysed as described in Example 1. No statistically significant differences in the mean body weight were observed between the treatment groups and NTC mice at any time points (results not shown; multiple t-tests corrected for multiple comparisons using the Holm-Sidak method) [Prism 6 for Mac OS X Version 6.0c, GraphPad Software, La Jolla Calif. USA, www.graphpad.com]. Animals appeared to tolerate the CVA21 and anti-CTLA-4 therapy well and there were no observable toxicities from the treatments. The decrease in weight was in the majority of cases linked to tumor ulceration and associated tumor burden.

Tumor Volumes of Primary B16-ICAM-1 Nodules.

Figure 13A:
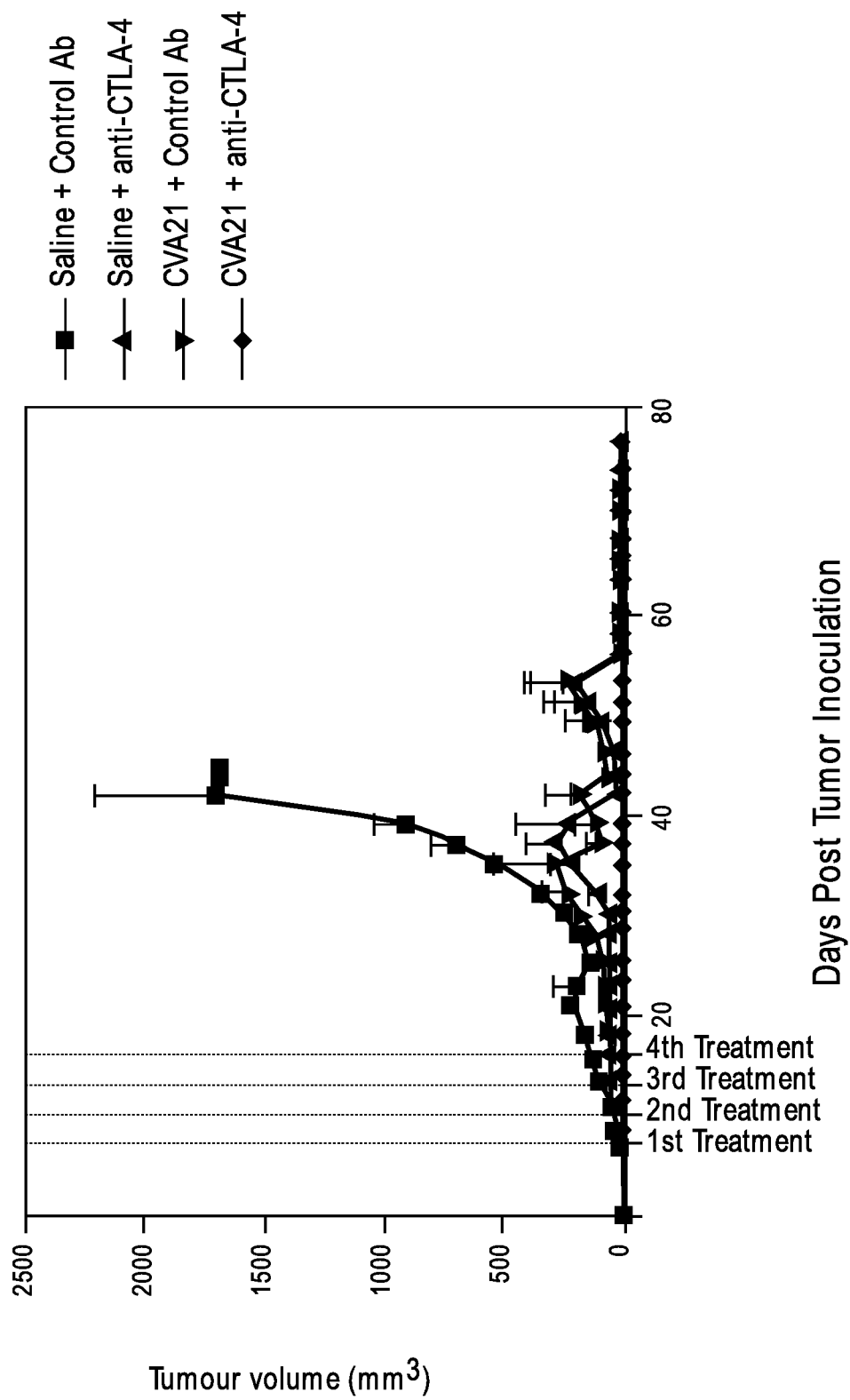
FIG. 13A-13C: Tumor volumes following combination immunotherapy and CVA21 virotherapy on B16-ICAM-1 murine melanoma tumors. (A) Average tumor volumes (mm3)±S.E.M. following treatment with either saline+control antibody, saline+anti-CTLA-4, CVA21+control antibody or CVA21+anti-CTLA-4. (B & C) Individual tumor volumes from each mouse following combination immunotherapy and CVA21 virotherapy on B16-ICAM-1 murine melanoma tumors. C57BL/6 mice were injected with B16-ICAM-1 cells intradermally on the hind flank. On days 7, 10, 13 and 16 tumors were injected intratumorally with either saline or CVA21 ($1 \times 10^8$ $TCID_{50}$ [$5.56 \times 10^9$ $TCID_{50}$/kg]), in combination with the control or anti-CTLA-4 antibody (12.5 mg/kg respectively). Treatment days are indicated by the dotted lines.
Figures 13B, 13C:
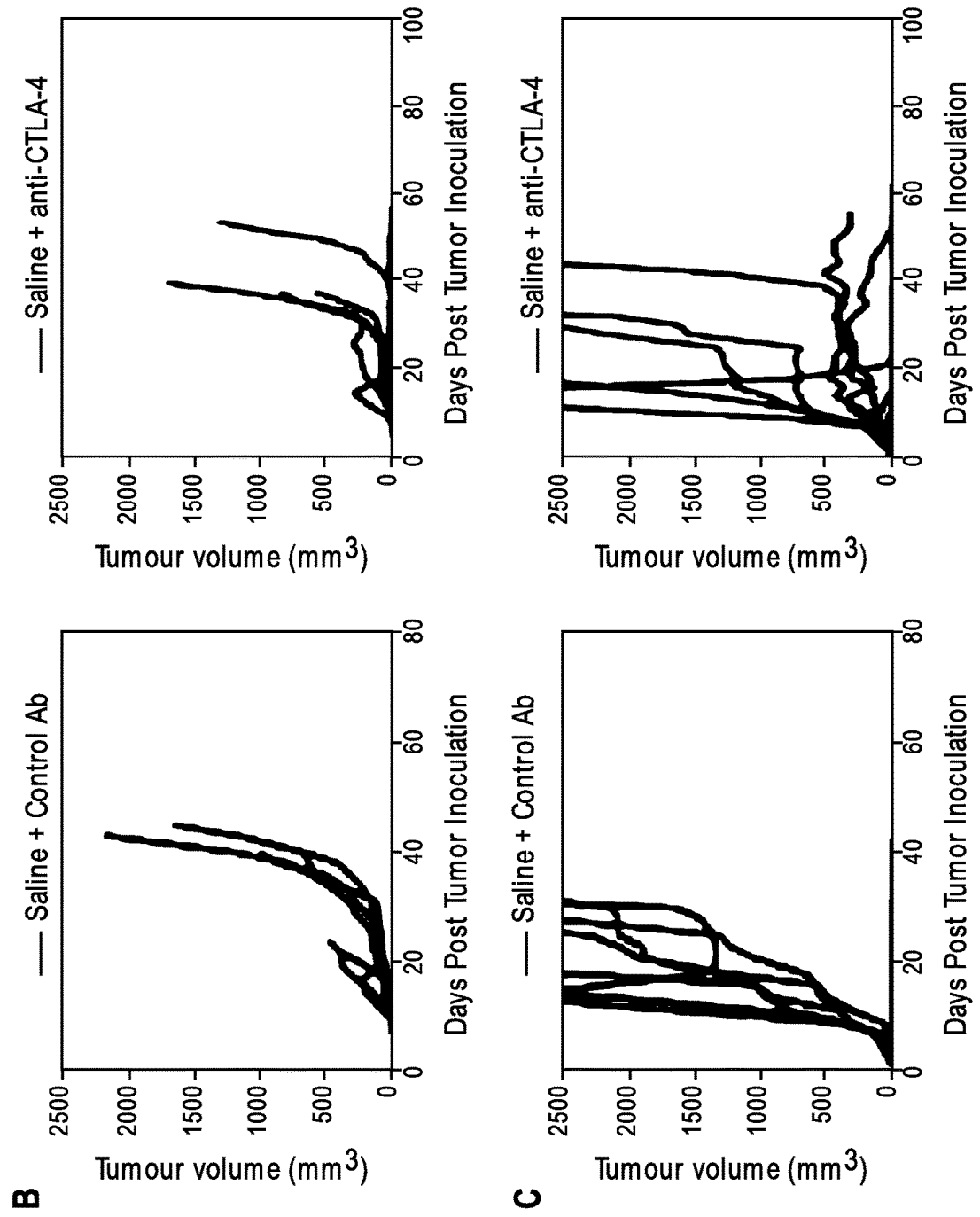
Figures 13B, 13C:
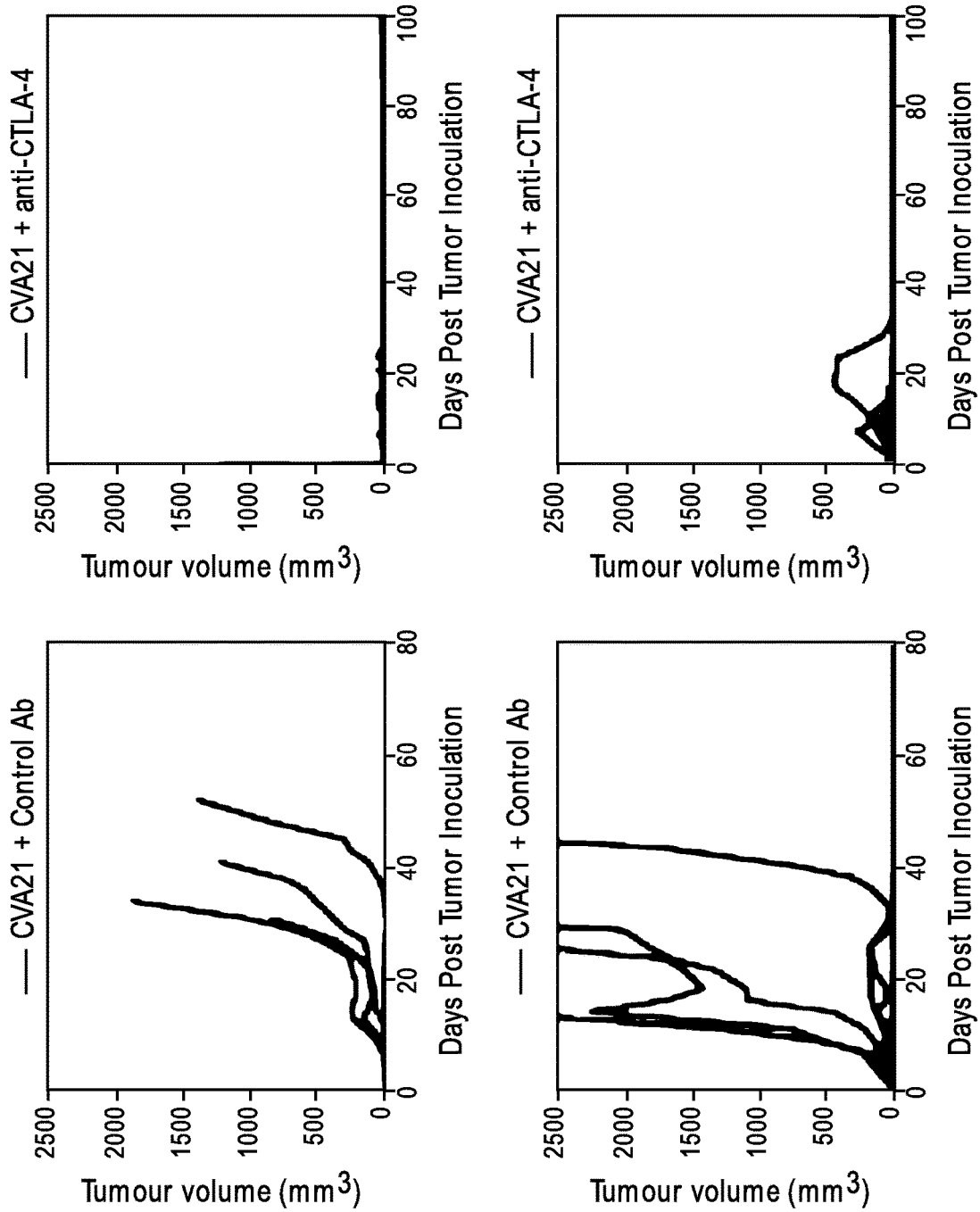

Tumor volumes were measured twice a week using electronic vernier calipers. By day 45, all saline+control antibody treated mice were euthanased due to progressive disease evidenced by tumor volume and tumor ulceration. As shown in FIG. 13, little anti-tumor activity was observed in the saline+control antibody treated tumors. All tumor volumes had escalated reaching the maximal humane endpoint and required euthanasia. The CVA21+anti-CTLA-4 treatment group showed the best responses with a notable delay in tumor onset and no animals showing signs of primary tumor growth during the latter half of the study. Complete tumor regression followed by a durable response was observed in 60% of animals treated with either monotherapies. More interestingly, all animals treated with CVA21+anti-CTLA-4 combination therapy demonstrated complete rejection against the primary tumor.

Tumor Volumes of Secondary B16 Nodules.

Figures 14A, 14B:
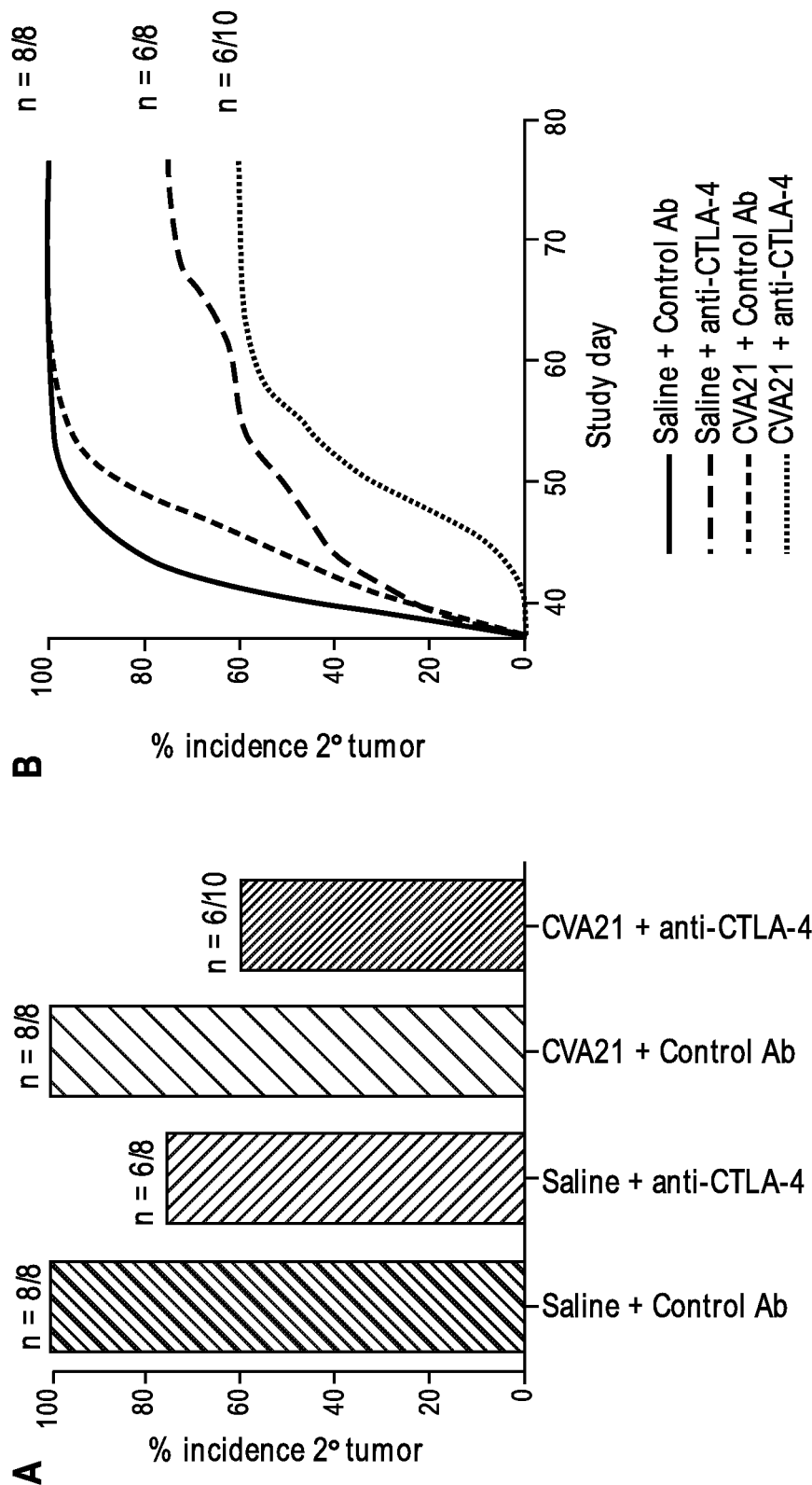
FIG. 14A-14C: Tumor volumes of secondary B16 tumor nodules. (A) Percentage incidence of secondary tumor development in saline+control antibody, saline+anti-CTLA-4, CVA21+control antibody, and CVA21+anti-CTLA-4 treated mice at the conclusion of the study (day 77). (B) Graph of tumor incidence vs days. Mice were rechallenged with B16 tumor cells on the hind flank at day 37 and tumors monitored up until day 77. (C) Individual tumor volumes from each mouse following rechallenge with B16 tumor cells ($2 \times 10^5$) on the right hind flank.
Figure 14C:
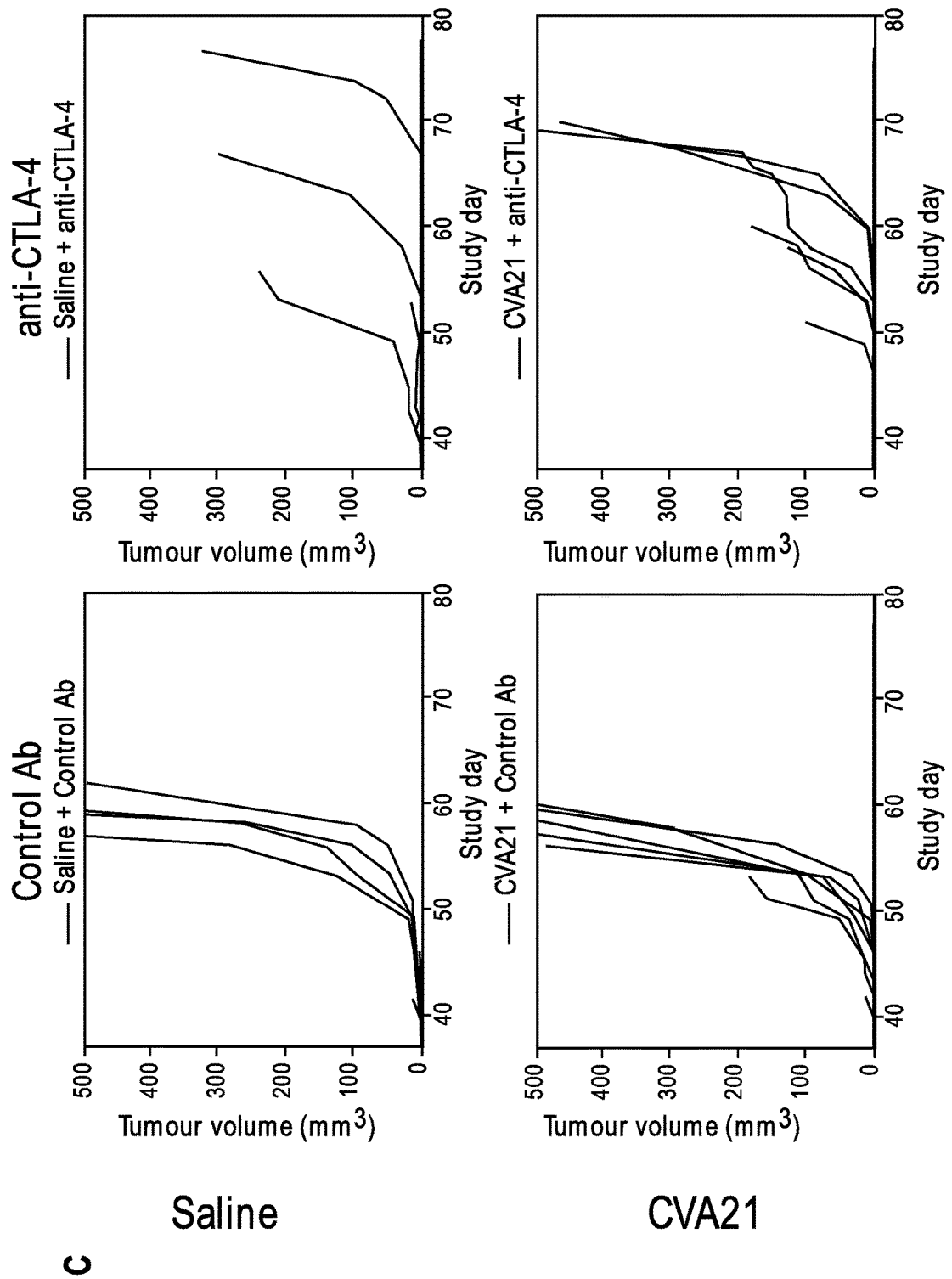

To establish whether a robust anti-tumoral immune response had developed following CVA21 therapy in combination with anti-CTLA-4 treatment, mice were rechallenged with B16 murine melanoma cells. B16 cells lack the human ICAM-1 receptor and are therefore resistant to CVA21 therapy. These cells are antigenically similar to the B16 cells used to generate the B16-ICAM-1 cell line and were used to identify the presence of anti-tumoral immune responses that may have resulted following oncolysis of the primary tumor. At day 77, animals treated with the anti-CTLA-4+CVA21 combination therapy demonstrated 40% protection against tumor rechallenge compared with 25% protection in the animals treated with single agent anti-CTLA-4 antibody (FIG. 14).

Enhanced Survival in Mice Treated with CVA21 in Combination with Anti-CTLA-4 Versus Saline and Anti-CTLA-4.

Figures 15A, 15B:
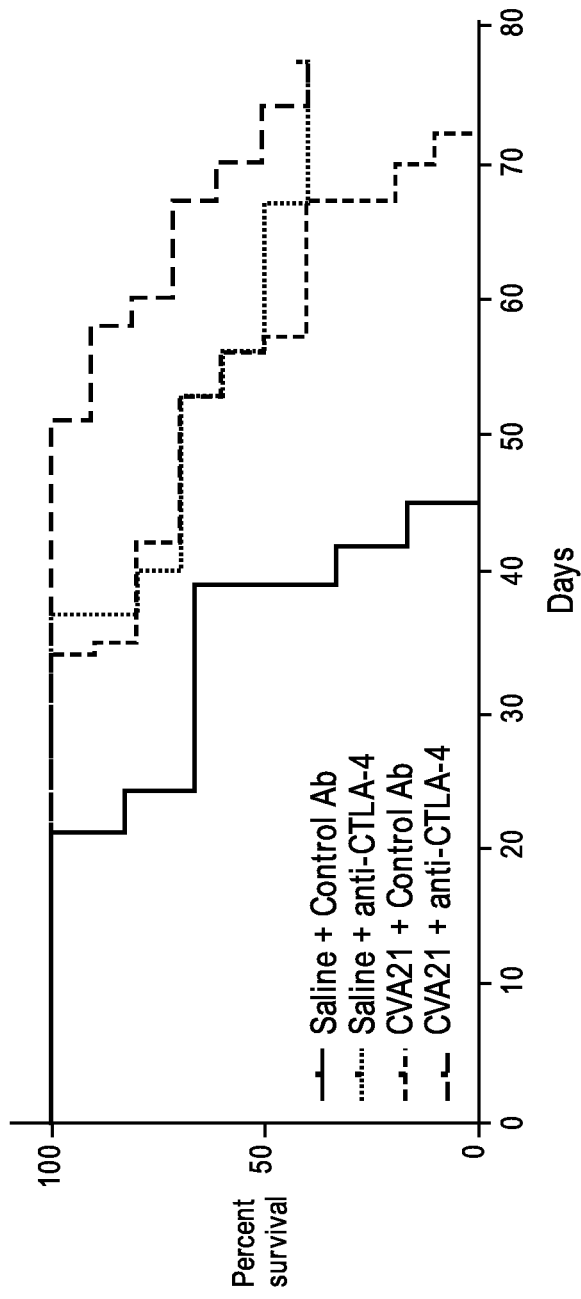
FIG. 15A-15B: Survival of C57BL/6 mice following treatment saline or CVA21 in combination with the control antibody or anti-CTLA-4. (A) Survival of C57BL/6 mice following treatment with saline or CVA21 in combination with the control antibody or anti-CTLA-4. The end/termination of the experiment was day 77. (B) Table showing median survival of mice from each treatment group.

Overall survival of animals on study. When compared against saline treated animals, all treatment groups significantly extend the overall survival of the animals. Single agent anti-CTLA-4 (p=0.0068), single agent CVA21 (p=0.0067) and CVA21+anti-CTLA-4+CVA21 (p=<0.0001). CVA21 in combination with the anti-CTLA-4 antibody demonstrated a statistically significant improvement in overall survival compared to the saline+Control antibody group (p<0.0001 Log-rank [Mantel-Cox] test) (FIG. 15). Comparing the CVA21+control antibody and the saline+control antibody group, there was no statistically significant difference. When the saline+anti-CTLA-4 survival curve was compared with the CVA21+anti-CTLA-4 treatment group there was a statistical difference (p=0.0026 Log-rank [Mantel-Cox] test) (FIG. 15). This finding suggests that CVA21 used in combination with the anti-CTLA-4 antibody gave a significant survival advantage (median survival of 45 vs 60 days for saline+anti-CTLA-4 and CVA21+anti-CTLA-4 respectively). Median survival of animals on study is shown in FIG. 15(B). Animals receiving the combination therapy of CVA21+anti-CTLA-4 had the longest median survival (72 days).

Discussion

The Example 3 results indicated that the use of CVA21 in combination with the anti-CTLA-4 antibody improved the overall survival of tumor bearing mice compared to animals receiving the CVA21+control antibody treatment group. All CVA21+anti-CTLA-4 treated B16-ICAM-1 tumors had regressed by day 77. CVA21 in combination with the anti-CTLA-4 antibody demonstrated a statistically significant improvement in overall survival compared to the saline+control antibody group (p<0.0001 Log-rank [Mantel-Cox] test) (FIG. 15). By day 45 all saline+control antibody treated mice were euthanased due to tumor progression and/or ulceration. The treatment regime of CVA21 in combination with the anti-CTLA-4 was well tolerated with no obvious adverse events attributed to the test articles.

The main finding of this study presented in Example 3 was that tumor bearing mice treated CVA21+anti-CTLA-4 showed an overall survival benefit that related to retardation of B16-ICAM-1 tumor growth. Animals treated with the CVA21+anti-CTLA-4 antibody showed an inhibition of disease progression vs control groups and were more resistant to rechallenge with a secondary B16 tumor compared to single agent treated groups.

Example 4: Intravenous Oncolytic CVA21 Virotherapy in Combination with the Immunostimulatory Antibody Anti-PD-1, Anti-CTLA-4 and Anti-PD-1+Anti CTLA-4 Tumor Study This study investigates the effectiveness of Coxsackievirus A21 (CVA21) oncolytic virotherapy in combination with the immunostimulatory antibodies anti-PD-1, anti-CTLA-4 and anti-PD-1+anti CTLA-4 in a B16-ICAM-1 murine model of malignant melanoma.

Mice were implanted with B16-ICAM-1 tumors intradermally ($2\times10^5$ cells) on the right hind flank and allowed to establish for seven days before commencement of therapy. Mice were treated with either intravenous saline or intravenous CVA21 ($1\times10^8$ $TCID_{50}$ [$5.56\times10^9$ $TCID_{50}$/kg assuming a 18 g mouse]), in combination with either a murine anti-PD-1 or anti-CTLA-4 or anti-PD-1+anti-CTLA-4 antibodies or a matched control antibody (12.5 mg/kg) on days 7, 10, 13 and 16. Saline or CVA21 treatments were administered intravenously while the anti-CTLA-4 and control antibodies were administered intraperitoneally (n=12-14 per group). The primary B16-ICAM-1 melanoma tumors were monitored regularly every 2 to 3 days using digital calipers and tumor volumes calculated based on the formula for a spheroid using the two longest perpendicular axes in the x/y plane of the tumor. Animals with tumors showing signs of ulceration, weight loss of >10% or tumor volumes greater than 2500 $mm^3$ were euthanased.

Tumor Volumes of Primary B16-ICAM-1 Nodules.

Figure 16A:
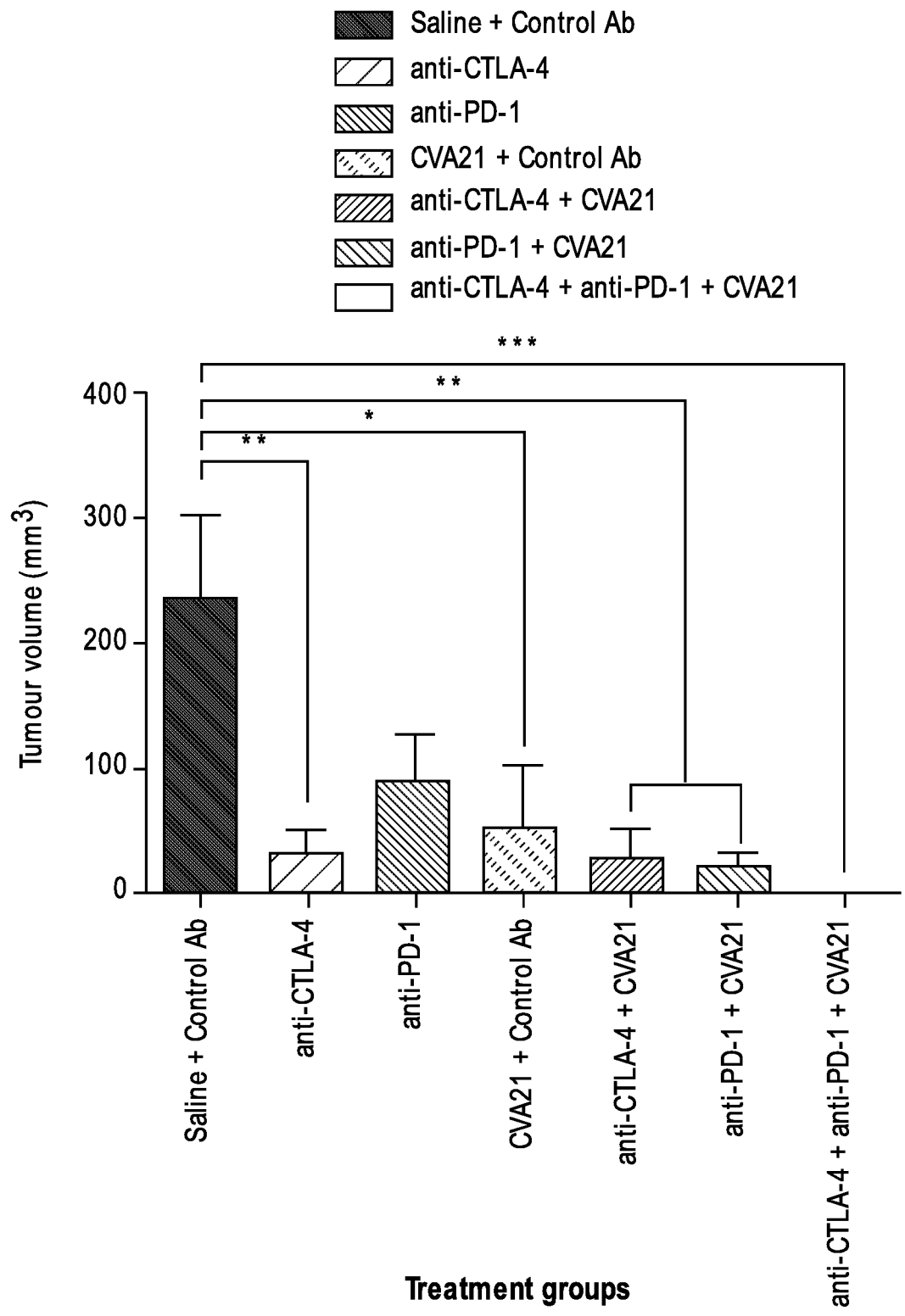
FIG. 16A-16C: Tumor volumes following combination immunotherapy and CVA21 virotherapy on B16-ICAM-1 murine melanoma tumors. (A) Average tumor volumes (mm3)±S.E.M. on study days 27 from mice treated with saline+control antibody, saline+anti-CTLA-4, saline+anti-PD-1, CVA21+control antibody, CVA21+anti-CTLA-4, CVA21+anti-PD-1 or CVA21+anti-CTLA-4+anti-PD-1. (B) Average tumor volumes (mm3)±S.E.M. following treatment with either saline+control antibody, saline+anti-CTLA-4, saline+anti-PD-1, CVA21+control antibody, CVA21+anti-CTLA-4, CVA21+anti-PD-1 or, CVA21+anti-CTLA-4+anti-PD-1. (C) Individual tumor volumes from each mouse following combination immunotherapy and CVA21 virotherapy on B16-ICAM-1 murine melanoma tumors. C57BL/6 mice were injected with B16-ICAM-1 cells intradermally on the hind flank. On days 7, 10, 13 and 16 mice were injected intravenously with either saline or CVA21 ($1\times10^8$ $TCID_{50}$ [$5.56\times10^9$ $TCID_{50}$/kg]), in combination with the control, anti-PD-1, anti-CTLA-4 or anti-CTLA-4+anti-PD-1 antibody (12.5 mg/kg respectively). Treatment days are indicated by the dotted lines.
Figure 16B:
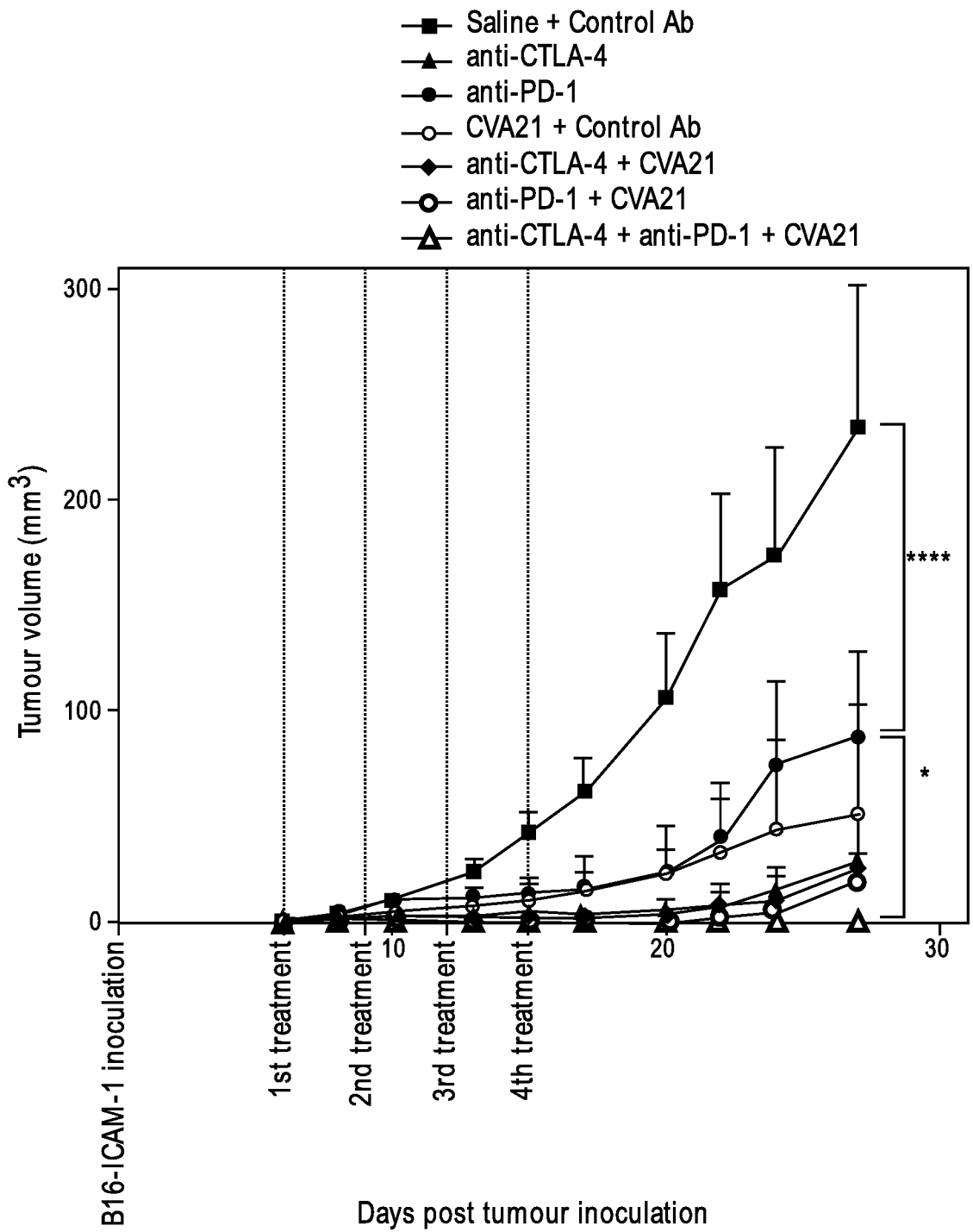
Figure 16C:
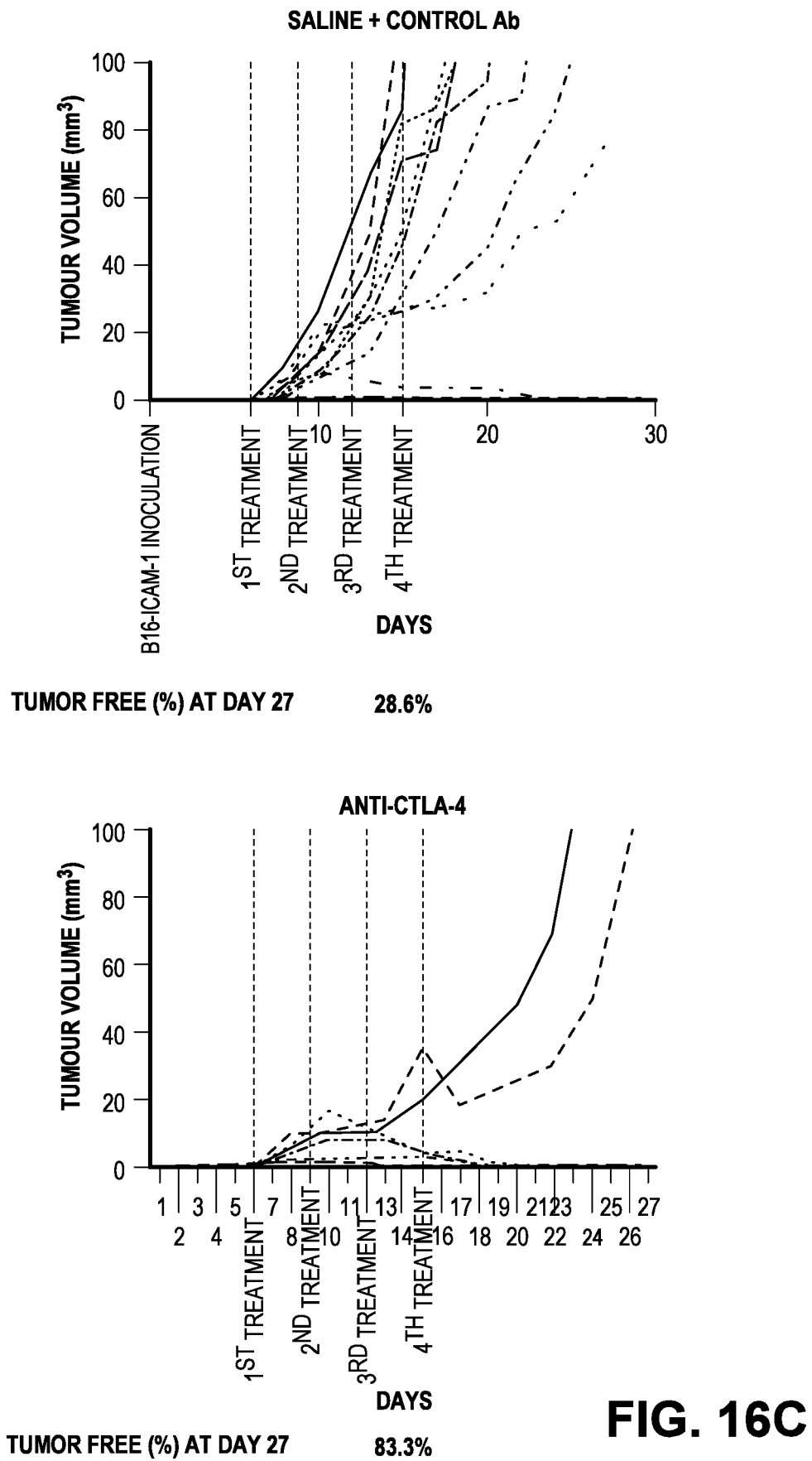
Figure 16C:
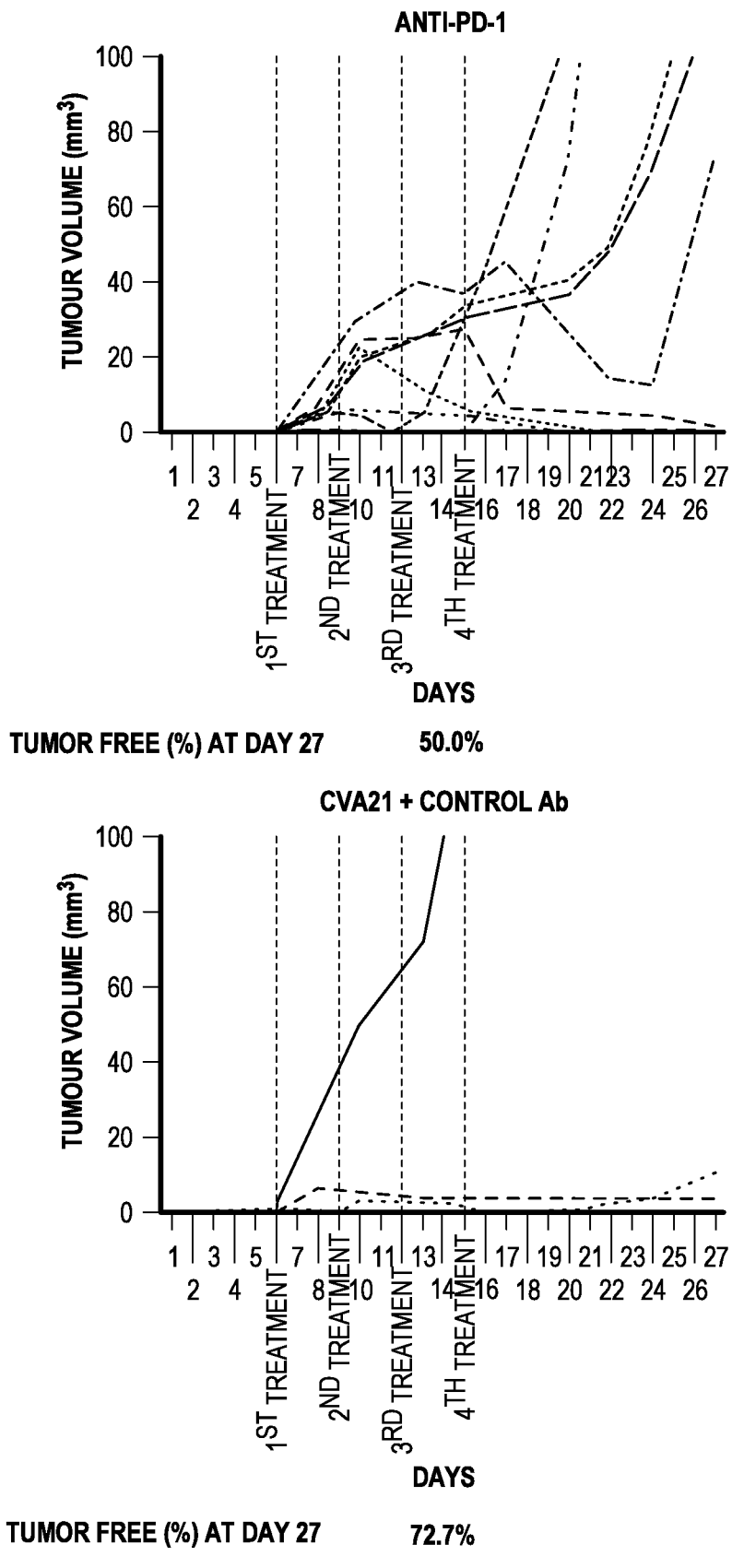
Figure 16C:
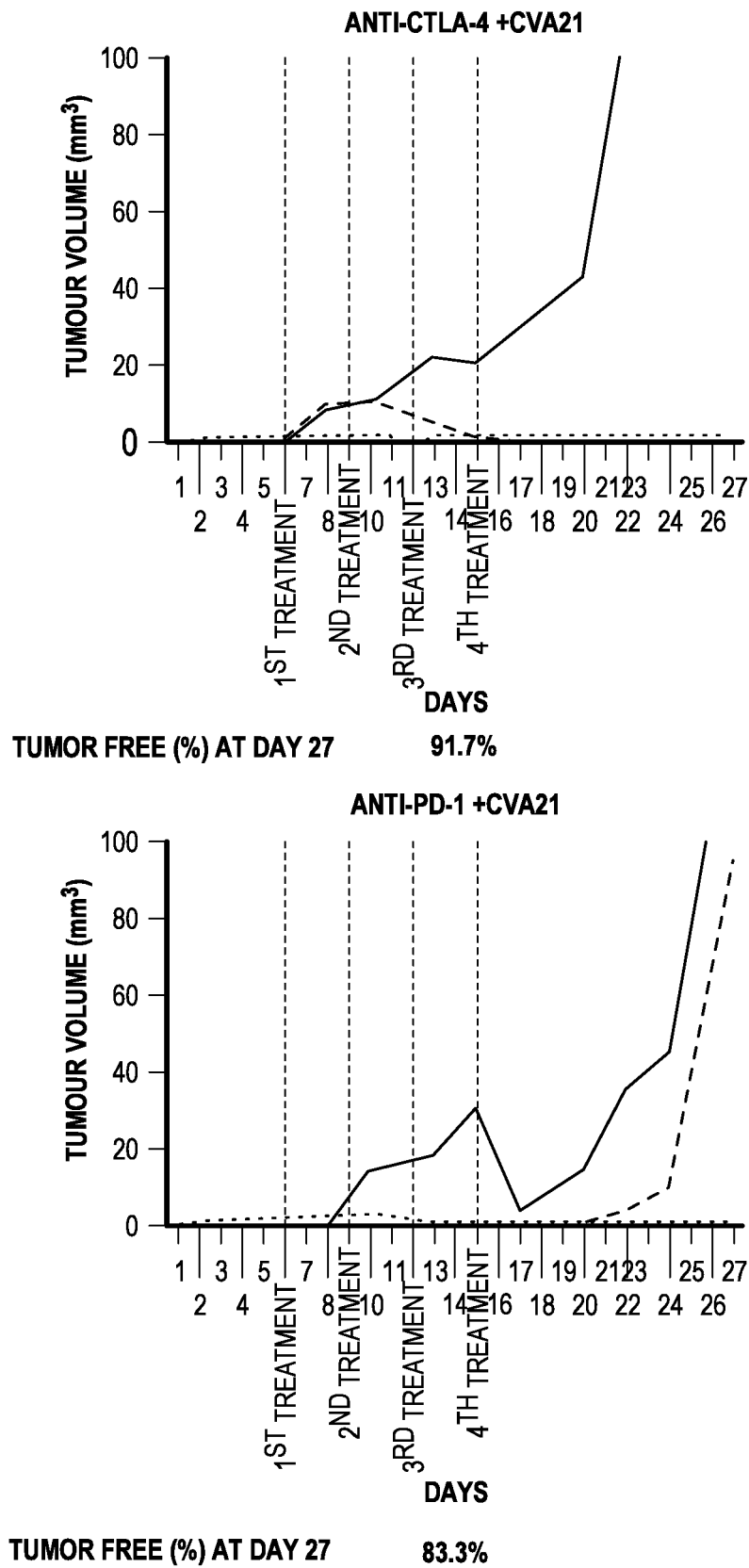
Figure 16C:
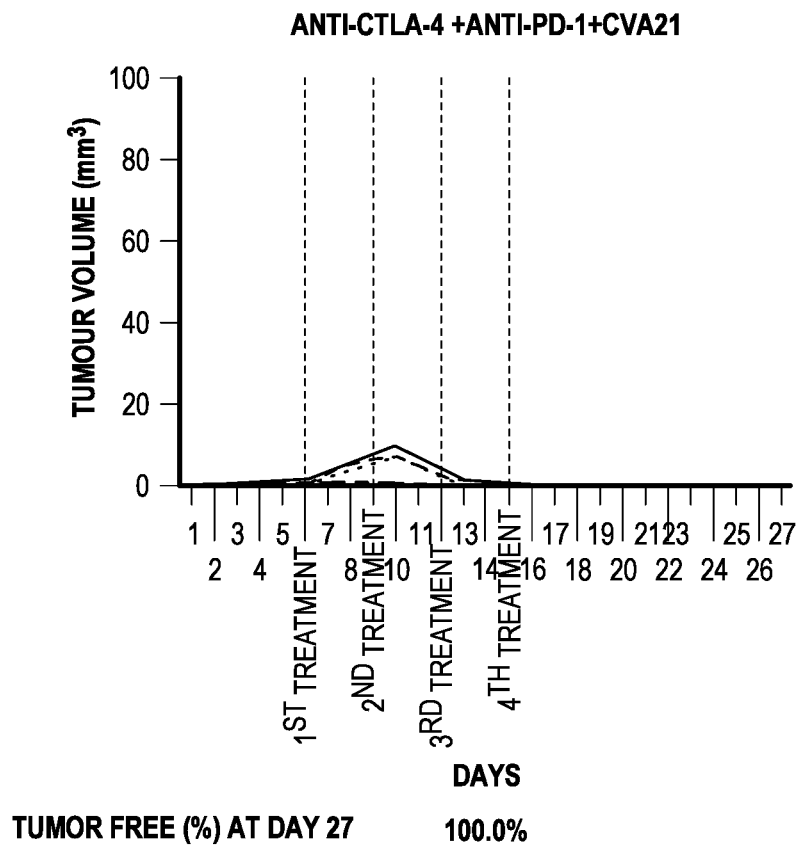

Tumor volumes were measured twice a week using electronic vernier calipers. As shown in FIG. 16A, at study day 27 little anti-tumor activity was observed in the saline+control antibody treated tumors. All single agent groups (CVA21, anti-PD-1 and anti-CTLA-4) displayed significant tumor reductions compared to the saline group. All combination treatment groups exhibited tumor reductions compared to the saline group but in general with greater significance levels with respect to the single agent treatments. In FIG. 16B analysis of mean tumor volumes throughout the entire study time course again indicated significant tumor reductions in both single agent and combination groups compared to the saline control animals. A notable trend was identified with the combination of anti-PD-1 and CVA21 displayed reduced tumor development kinetics compared to single agent CVA21 or anti-PD-1 treatment alone. Individual spider plots of tumor development are displayed in FIG. 16C. The data indicate significant reduction in the incidence of papable tumor development in all treatment groups compared to the saline control group. Of particular note is the reduction of tumor incidence in both anti-PD-1 and anti-CTLA-4 when combined with intravenous CVA21 administration compared to the presence of detectable tumors in the single agent anti-PD-1 or anti-CTLA-4 treated animals. More surprising, is the observation that all animals treated with CVA21+anti-PD-1+anti-CTLA-4 combination therapy demonstrated complete rejection against the primary tumor development at study day 27.

Example 5: Systemic Effect of CVA21 Intra-Tumoral Injection on Distant Tumours

Figure 17:
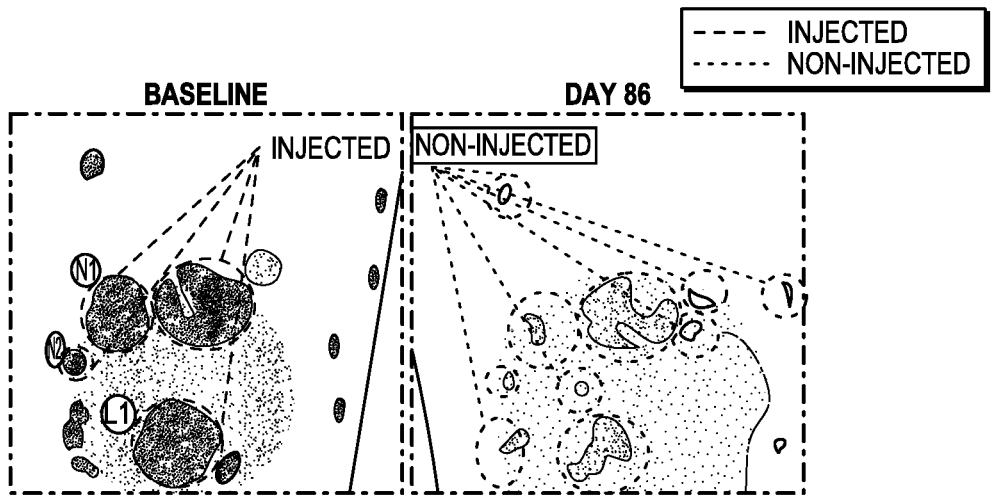
FIG. 17: Pt 12-002: Intra-tumoral CVA21 injection of metastatic melanoma lesions on the leg of a male patient showing the effect on injected and non-injected lesions at day 85. Pt 03-032: Male with metastatic melanoma to left neck and lungs, showing non-injected distant visceral response at day 86. Injection of CVA21 intratumorally in the left neck only.
Figure 17:
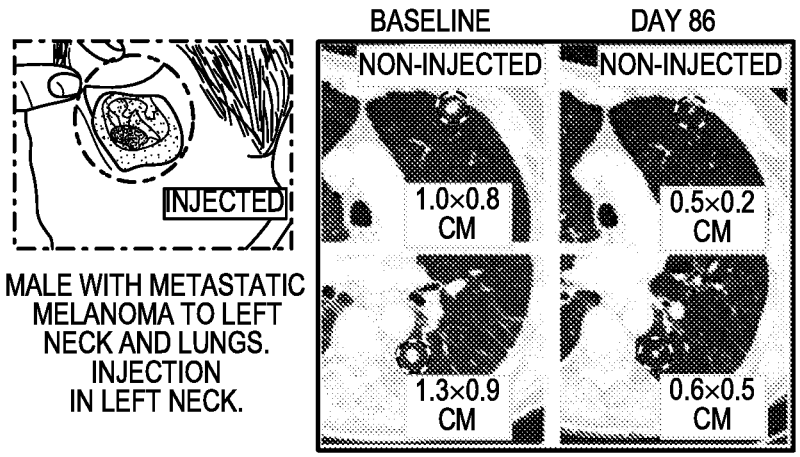

Following intratumoural (i.t) injection, CVA21 preferentially infects ICAM-1 expressing tumour cells, resulting in tumour cell lysis and a systemic immune-mediated anti-tumour response. A Phase II trial of i.t delivered CVA21 in advanced melanoma patients has highlighted antitumour activity in both injected and distant non-injected lesions (FIG. 17).

The CALM study (CAVATAK™ in Late stage Melanoma) investigated the efficacy and safety of intratumoral administration of CVA21 in 57 patients with treated or untreated unresectable Stage IIIC-IVM1c melanoma. Each patient received CVA21 up to a total dose of $3 \times 10^{8.0}$) $TCID_{50}$ (about $4.5 \times 10^6$ $TCID_{50}$/kg for a 70 kg patient) in a maximum volume of 4.0 mL by i.t. administration on Days 1, 3, 5, 8, 22, 43, 64 and at further 3-weekly intervals (up to a maximum of 10 sets of injections) until confirmed disease progression or development of excessive toxicity. At each scheduled injection visit, if possible, multiple lesions were injected in a dose hyper-fraction pattern, starting with the largest lesion(s) (2.0 mL of CVA21 injected into tumors>2.5 cm, 1.0 mL of CVA21 into 1.5 to 2.5 cm; 0.5 mL of CVA21 into 0.5 to 1.5 cm) to a 4.0 mL maximum, using ultrasound guidance if necessary. The length of each tumor to be injected is measured and the volume of CVA21 to be injected into each tumor determined. The sum of these volumes is the total volume of CVA21 required for the administration. The maximum volume of CVA21 to be administered is 4.0 mL. Following initial injection with CVA21, any injected lesion that reduces in diameter to <0.5 cm was injected with 0.1 mL of CVA21 as per the stated treatment schedule until the lesion completely resolved. Patients displaying immune-related progression-free survival (irPFS) or better at 6 months were eligible for 9 additional series of injections. Key eligibility criteria were ≥18 rs old, ECOG 0-1, and at least 1 injectable cutaneous, sc, or nodal tumor>1.0 cm The primary endpoint was to achieve>9 of 54 evaluable patients with irPFS at 6 months following treatment: secondary endpoints included 1-year survival and objective response rates. A 2-stage Simon's minimax design was employed. Thirty-five patients were treated in Stage 1 with a futility clause requiring the observation of 3 or more objective responses (complete or partial; CR or PR, respectively) assessed by modified Response Evaluation Criteria in Solid Tumours (RECIST 1.1; Eisenhauer, et al., 2009) criteria in these patients to progress to Stage 2. A further 22 patients were enrolled in Stage 2.

The primary endpoint of the study was achieved with 21 of 57 (38.6%) evaluable patients displaying irPFS at 6 months with a median irPFS of 4.2 mos. The overall response rate (irRECIST) was 28.1% (16 of 57 evaluable patients) with a ≥6 months durable response rate of 19.3% (11 of 57 patients). The median time to response was 2.8 months, and the 1-year survival rate 75.4% (43 of 57 patients). After a median follow-up of ~16.5 months, median duration of response in responders and median overall survival (OS) for all patients was not reached. The most common adverse events (AE's) were Grade 1 fatigue, chills, local injection site reactions and fever. No Grade 3 or 4 product-related AE's were observed.

Antitumour activity in both injected and distant non-injected lesions was evident in patients (FIG. 17), the latter observation in particular being consistent with a systemic immune-mediated anti-tumour response. CVA21 mediated non-injected distant metatastic lesion activity was linked to a possible novel serum cytokine signature of elevated levels of serum IL-8 and g-IFN indicating the generation of a potential active systemic anti-tumor immune response.

Blockade of programmed death 1 (PD-1) and CTLA-4 in patients with metastatic melanoma has resulted in substantial tumour responses via a mechanism involving reversal of tumour induced T cell suppression. As demonstrated herein, the combination of CVA21 and PD-1 or CTLA-4 blockade enhances antitumour responses, thereby offering improved clinical activity.

Example 6: Intravenous Administered CVA21 Induces Tumor Cell Gene Expression Changes Balb-C SCID mice were implanted on the left flank with SK Mel 28 cells (day 0). Mice were administered either CVA21 or saline intravenously by injection into the tail vein (Day 14). Mice were sacrificed at 3 h, 6 h, 24 h and 72 h post-treatment and the tumors excised for viral and cellular gene profiling. Upregulation of interferon-g inducible protein 10 (IP-10) and PD-L1 was observed in tumour cells from mice treated with CVA21 (FIG. 19).

Cells, culture conditions, and virus were generally as described in Example 1. Female SCID-BALB/c mice of 6-8 weeks of age were obtained from the ARC (Perth, Australia) and were housed under SPF conditions within the university animal holding facility. SK-Mel-28 cells were grown in DMEM containing 10% FCS. Cells were harvested and washed twice in sterile PBS. Cell viability was assessed by trypan blue staining as cellular viability>95% was required for xenotransplantation. Cells were resuspended in sterile PBS and kept on ice to maintain viability. Prior to xenotransplantation, mice were anaesthetised via isoflurane inhalation (4 L/min, maintained at 2%). Mice were given a sub-cutaneous injection of $2 \times 10^6$ SK-Mel-28 cells into the hind flank. Mice were visually monitored daily and weighed every 3 to 4 days. Tumour development was monitored every 3 to 4 days by palpation. Tumours were measured using electronic callipers and estimates of tumour volume were as described above (Example 1).

Once tumours were palpable (volume≈50 mm³), mice were anaesthetised with isoflurane (4 L/min, maintained at 2%) and administered $1 \times 10^7$ $TCID_{50}$ CVA21 or sterile PBS (total volume 100 μL) via the retro-orbital route. Four mice from each tumour model, two of which had been treated with PBS and two of which had been treated with CVA21 were subsequently sacrificed via $CO_2$ asphyxiation at 3, 6, 24 and 72 h post-treatment. Blood was taken via cardiac puncture. Tumours were excised and stored in RNALater (QIAGEN) for RNA stabilisation at 4° C. Serum (at a starting dilution of 1:10-1:100) was assayed for the presence of infectious virus via the endpoint viral infectivity assay in triplicate, as follows.

To determine the titre of CVA21 in infected samples, SK-Mel-28 cells were seeded in 96-well plates and grown to 50-80% confluency in DMEM containing 2% FCS. Cell monolayers were inoculated with 10-fold serial dilutions of purified CVA21 in triplicate or quadruplicate in DMEM containing 2% FCS and incubated at 37° C. in a 5% $CO_2$ environment for 72 h. Wells that exhibited CPE upon microscopic examination were scored as positive. Fifty percent infectious endpoint titres were calculated using the Karber method (Dougherty, 1964). Total RNA was extracted from xenograft tissue using an RNEasy Mini Kit (QIAGEN)

according to the manufacturer's protocol. Viral RNA was extracted from serum using the Viral RNA Mini Kit (QIAGEN) according to the manufacturer's protocol.

RNA extracted from tumour and serum samples was analysed to determine the levels of CVA21 RNA present using real-time quantitative RT-PCR. One step RT-PCR was carried out using the SuperScript III Platinum One-Step qRT-PCR Kit (Invitrogen). The primers and probe were specific for the VP3 region of the CVA21 (Kuykendall) genome and were designed using Primer Express 1.5 Software (Applied Biosystems, Foster City, Calif.). The sequence for the forward primer (KKVP3fwd) was 5'-GAGCTAAACCACCAACCAATCG-3' (SEQ. ID. NO.: 1) and the reverse primer (KKVP3rev) was 5'-CGGTGCAACCATGGAACAA-3' (SEQ. ID. NO.: 2). The FAM labelled probe (KKVP3) used was 6FAM CACACACATCATCTGGGA-MGB (SEQ. ID. NO.: 3). In a volume of 25 µL, the reaction mixture comprised 1× SuperScript reaction mix, 500 nM forward primer, 500 nM reverse primer, 250 nM probe, 500 nM ROX, 0.5 µL SuperScript III RT/Platinum Taq Mix and 5 µL extracted RNA. RT-PCR reactions were carried out using the ABI Prism 7000 Sequence Detection System (Applied Biosystems). Cycling conditions were 30 min at 60° C., followed by 5 min at 95° C. and then 50 cycles of 15 sec at 95° C. and 1 min at 60° C. Samples were quantitated against pre-validated CVA21 RNA standards of known concentration and results reported as equivalent TCID50/mL for serum RNA or TCID50/mg for xenograft tissue RNA cRNA was amplified and a biotin-dUTP label incorporated. Biotinylated cRNA samples obtained from SK-Mel-28 xenografts were hybridised to HumanRef-8 v2 Expression BeadChips (Illumina), representing>22 000 transcripts, according to the manufacturer's protocol. Beadchip arrays were scanned using the BeadStation 500 System (Illumina). Microarray data were analysed using GeneSpring 7.0 software (Silicon Genetics, USA). Data sets were transformed by setting measurements<0.01 to 0.01 and then further normalised per chip to a 50th percentile and per gene to a median. Within each xenograft model, data sets from each pair of mice obtained for each treatment (PBS and CVA21) and time point (3, 6, 24 and 72 h) were analysed as replicate-samples. Genes were filtered based on positive gene expression (signal intensity) in at least one of the replicate-samples.

Intracellular viral replication is an attractive process to initiate a targeted disruption of the delicate balance of host immune system activities. In FIG. 19, systemic delivery of CVA21 to a human melanoma xenograft in a mouse model induced significant targeted viral replication as evidence by the increasing levels of CVA21 specific RNA within the tumor tissue throughout the duration of the study, starting in particular at 24 h post-systemic administration via the retro-orbital route. Gene expression analysis at 3, 6, 24 and 72 hrs post-CVA21 revealed significant up-regulation of interferon responses gene within the tumor microenvironment, in particular the interferon inducible protein-10 (IP-10), a chemokine secreted from cells exposed to IFN-g and which plays an important role in recruiting activated T-cells into sites of tissue inflammation. As IFN-g provided by activated T-cells is known to up-regulate immune checkpoint molecules, expression levels of the PD-L1 gene were monitored. As illustrated in FIG. 19, as CVA21 replication peaked at 24-72 hrs post systemic administration, in parallel an accompanying increase IP-10 and PD-L1 expression, indicating IFN-g activity. Based on the immune agitation induced by targeted CVA21 replication in the melanoma tumor tissue, the inventors anticipate that this immune stimulating event may increase the anti-tumor activity of immune-checkpoint blockade when both agents are used in combination.

REFERENCES

Hodi F S, O'Day S J, McDermott D F, Weber R W, Sosman J A, Haanen J B, et al. Improved survival with ipilimumab in patients with metastatic melanoma. N Engl J Med. 2010 August; 363(8):711-23.

Keir M E, Butte M J, Freeman G J, Sharpe A H. PD-1 and its ligands in tolerance and immunity. Annu Rev Immunol. 2008; 26:677-704.

Brahmer J R, Tykodi S S, Chow L Q M, Hwu W J, Topalian S L, Hwu P, et al. Safety and activity of anti-PD-L1 antibody in patients with advanced cancer. N Engl J Med. 2012 June; 366(26):2455-65.

Topalian S L, Hodi F S, Brahmer J R, Gettinger S N, Smith D C, McDermott D F, et al. Safety, activity, and immune correlates of anti-PD-1 antibody in cancer. N Engl J Med. 2012 June; 366(26):2443-54.

Curran M A, Montalvo W, Yagita H, Allison J P. PD-1 and CTLA-4 combination blockade expands infiltrating T cells and reduces regulatory T and myeloid cells within B16 melanoma tumors. Proc Natl Acad Sci USA. 2010 March; 107(9):4275-80.

Merelli B, Massi D, Cattaneo L, Mandala M. Targeting the PD1/PD-L1 axis in melanoma: biological rationale, clinical challenges and opportunities. Crit Rev Oncol Hematol. 2014 January; 89(1):140-65.

Ott P A, Hodi F S, Robert C. CTLA-4 and PD-1/PD-L1 blockade: new immunotherapeutic modalities with durable clinical benefit in melanoma patients. Clin Cancer Res. 2013 October; 19(19):5300-9.

Shafren D R, Au G G, Nguyen T, Newcombe N G, Haley E S, Beagley L, et al. Systemic therapy of malignant human melanoma tumors by a common cold-producing enterovirus, coxsackievirus a21. Clin Cancer Res. 2004 January; 10(1 Pt 1):53-60.

Au G G, Lindberg A M, Barry R D, Shafren D R. Oncolysis of vascular malignant human melanoma tumors by Coxsackievirus A21. Int J Oncol. 2005 June; 26(6):1471-6.

Blanchard T, Srivastava P K, Duan F. Vaccines against advanced melanoma. Clin Dermatol. 2013; 31(2):179-90.

Garbe C, Eigentler T K, Keilholz U, Hauschild A, Kirkwood J M. Systematic review of medical treatment in melanoma: current status and future prospects. Oncologist. 2011; 16(1):5-24.

Dougherty R M. Animal virus titration techniques. Techniques in experimental virology. 1964; 178.

Robert C, Thomas L, Bondarenko I, O'Day S, M D J W, Garbe C, et al. Ipilimumab plus dacarbazine for previously untreated metastatic melanoma. N Engl J Med. 2011 June; 364(26):2517-26.

E. A. Eisenhauera, P. Therasseb, J. Bogaertsc, L. H. Schwartzd, D. Sargente, R. Fordf, J. Danceyg, S. Arbuckh, S. Gwytheri, M. Mooneyg, L. Rubinsteing, L. Shankarg, L. Doddg, R. Kaplanj, D. Lacombec, J. Verweijk New response evaluation criteria in solid tumours: Revised RECIST guideline (version 1.1). European Journal of Cancer 45 (2009) 228-247.

Dougherty, R. M. 1964. Animal virus titration techniques, p. 169-223. In R. J. C. Harris (ed.), Techniques in experimental virology. Academic Press, New York.)

The invention claimed is:

1. A method for the treatment of cancer in a subject comprising (i) intratumorally administering to the subject a therapeutically effective amount of Coxsackievirus CVA21 up to a total dose of $3 \times 10^8$ $TCID_{50}$ per injection day and (ii) systemically co-administering a therapeutically effective amount of an anti-PD-1 monoclonal antibody to the subject.

2. The method of claim 1, wherein an increase in PD-L1 expression occurs in tumor cells of the subject following administration of the Coxsackievirus CVA21.

3. The method of claim 2, wherein the administration of said Coxsackievirus CVA21 is prior to administration of the antibody.

4. The method of claim 2, wherein the anti-PD-1 antibody is Lambrolizumab.

5. The method of claim 2, wherein the cancer is an intercellular adhesion molecule-1 (ICAM-1) expressing cancer.

6. The method of claim 1, wherein said antibody is administered via intravenous infusion to the subject.

7. The method of claim 6, wherein the administration of said Coxsackievirus CVA21 is prior to administration of the antibody.

8. The method of claim 6, wherein the cancer is an intercellular adhesion molecule-1 (ICAM-1) expressing cancer.

9. The method of claim 1, wherein the cancer is bladder cancer.

10. The method of claim 9, wherein the administration of said Coxsackievirus CVA21 is prior to the administration of the antibody.

11. The method of claim 1, wherein the method further comprises administering a therapeutically effective amount of an anti-CTLA-4 antibody.

12. The method of claim 1, wherein the anti-PD-1 antibody is Lambrolizumab.

13. The method of claim 3 or 12, wherein the cancer is an intercellular adhesion molecule-1 (ICAM-1) expressing cancer.

14. The method of claim 1, wherein the cancer is an intercellular adhesion molecule-1 (ICAM-1) expressing cancer.

15. The method of claim 12, wherein the cancer is ovarian cancer.

16. The method of claim 12, wherein the cancer is colorectal cancer.

17. The method of claim 12, wherein the cancer is renal cancer.

18. The method of claim 12, wherein the cancer is pancreatic cancer.

19. The method of claim 12, wherein the cancer is prostate cancer.

20. The method of claim 12, wherein the cancer is thyroid cancer, adrenal cancer, lymphoid cancer, or leukemia.

21. The method of any one of claims 1-7, wherein the subject is a human patient and wherein the Coxsackievirus CVA21 is intratumorally administered at a total dose of $3\times10^8$ TCID$_{50}$ per injection day.

22. The method of claim 21, wherein the Coxsackievirus CVA21 is intratumorally administered on days 1, 3, 5, 8, 22, 43 and 64, and then administered at further 3-week intervals.

23. The method of any one of claims 1-7, 8, 12, or 14, wherein the treatment provides increased survival time for the subject compared to the survival time for a subject administered the therapeutically effective amount of the Coxsackievirus CVA21 alone.

24. The method of any one of claims 1-7, 8, 12, or 14, wherein the treatment provides increased survival time for the subject compared to the survival time for a subject administered the therapeutically effective amount of the anti-PD-1 monoclonal antibody alone.

25. A method for the treatment of an ICAM-1 expressing cancer in a human patient comprising (i) intratumorally administering to the human patient a therapeutically effective amount of Coxsackievirus CVA21 up to a total dose of $3\times10^8$ TCID$_{50}$ per injection day and (ii) systemically co-administering a therapeutically effective amount of anti-PD-1 monoclonal antibody Lambrolizumab to the human patient.

26. The method of claim 25, wherein the administration of said Coxsackievirus CVA21 is prior to administration of the antibody.

27. A method for the treatment of an ICAM-1 expressing cancer in a human patient comprising (i) intratumorally administering to the human patient a therapeutically effective amount of Coxsackievirus CVA21 up to a total dose of $3\times10^8$ TCID$_{50}$ per injection day, wherein the injection days are on days 1, 3, 5, 8, 22, 43 and 64, and then at further 3-week intervals and (ii) systemically co-administering a therapeutically effective amount of anti-PD-1 monoclonal antibody Lambrolizumab to the human patient.

28. A method for the treatment of melanoma in a human patient comprising (i) intratumorally administering to the human patient a therapeutically effective amount of Coxsackievirus CVA21 up to a total dose of $3\times10^8$ TCID$_{50}$ per injection day and (ii) systemically co-administering a therapeutically effective amount of anti-PD-1 monoclonal antibody Lambrolizumab to the human patient.

29. The method of claim 28, wherein the administration of said Coxsackievirus CVA21 is prior to administration of the antibody.

30. A method for the treatment of melanoma in a human patient comprising (i) intratumorally administering to the human patient a therapeutically effective amount of Coxsackievirus CVA21 up to a total dose of $3\times10^8$ TCID$_{50}$ per injection day, wherein the injection days are on days 1, 3, 5, 8, 22, 43 and 64, and then at further 3-week intervals and (ii) systemically co-administering a therapeutically effective amount of anti-PD-1 monoclonal antibody Lambrolizumab to the human patient.

31. A method for the treatment of melanoma in a human patient comprising (i) intratumorally administering to the human patient a therapeutically effective amount of Coxsackievirus CVA21 up to a total dose of $3\times10^8$ TCID$_{50}$ per injection day and (ii) systemically co-administering a therapeutically effective amount of anti-PD-1 monoclonal antibody Lambrolizumab to the human patient, and (iii) further comprising the step of tumor resection following (i) and (ii).

32. A method for the treatment of bladder cancer in a human patient comprising (i) intravesicularly administering to the human patient a therapeutically effective amount of Coxsackievirus CVA21 up to a total dose of $3\times10^8$ TCID$_{50}$ per injection day and (ii) systemically co-administering a therapeutically effective amount of anti-PD-1 monoclonal antibody Lambrolizumab to the human patient.

33. The method of claim 32, wherein the administration of said Coxsackievirus CVA21 is at about the same time as administration of the antibody.

34. A method for the treatment of breast cancer in a human patient comprising (i) intratumorally administering to the human patient a therapeutically effective amount of Coxsackievirus CVA21 up to a total dose of $3\times10^8$ TCID$_{50}$ per injection day and (ii) systemically co-administering a therapeutically effective amount of anti-PD-1 monoclonal antibody Lambrolizumab to the human patient.

35. The method of claim 34, wherein the administration of said Coxsackievirus CVA21 is prior to administration of the antibody.

36. The method of claim 34, wherein the treatment comprises (i) intratumorally administering to the human patient a therapeutically effective amount of Coxsackievirus CVA21 up to a total dose of $3\times10^8$ TCID$_{50}$ per injection day, wherein the injection days are on days 1, 3, 5, 8, 22, 43 and 64, and then at further 3-week intervals and (ii) systemically co-administering a therapeutically effective amount of anti-PD-1 monoclonal antibody Lambrolizumab to the human patient.

37. A method for the treatment of liver cancer in a human patient comprising (i) intratumorally administering to the human patient a therapeutically effective amount of Coxsackievirus CVA21 up to a total dose of $3\times10^8$ TCID$_{50}$ per injection day and (ii) systemically co-administering a therapeutically effective amount of anti-PD-1 monoclonal antibody Lambrolizumab to the human patient.

38. The method of claim 37, wherein the administration of said Coxsackievirus CVA21 is prior to administration of the antibody.

39. A method for the treatment of stomach cancer in a human patient comprising (i) intratumorally administering to the human patient a therapeutically effective amount of Coxsackievirus CVA21 up to a total dose of $3\times10^8$ TCID$_{50}$ per injection day and (ii) systemically co-administering a therapeutically effective amount of anti-PD-1 monoclonal antibody Lambrolizumab to the human patient.

40. The method of claim 39, wherein the administration of said Coxsackievirus CVA21 is prior to administration of the antibody.

41. A method for the treatment of non-small cell lung cancer in a human patient comprising (i) intratumorally administering to the human patient a therapeutically effective amount of Coxsackievirus CVA21 up to a total dose of $3\times10^8$ TCID$_{50}$ per injection day and (ii) systemically co-administering a therapeutically effective amount of anti-PD-1 monoclonal antibody Lambrolizumab to the human patient.

42. The method of claim 41, wherein the administration of said Coxsackievirus CVA21 is prior to administration of the antibody.

* * * * *

SEQUENCE LISTING

```
<160> NUMBER OF SEQ ID NOS: 3

<210> SEQ ID NO 1
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Forward Primer - KKVP3fwd

<400> SEQUENCE: 1
gagctaaacc accaaccaat cg                                        22

<210> SEQ ID NO 2
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Reverse Primer - KKVP3rev

<400> SEQUENCE: 2
cggtgcaacc atggaacaa                                            19

<210> SEQ ID NO 3
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: FAM labelled probe (KKVP3)

<400> SEQUENCE: 3
cacacacatc atctggga                                             18
```